US009775903B2

(12) United States Patent
Posner et al.

(10) Patent No.: US 9,775,903 B2
(45) Date of Patent: Oct. 3, 2017

(54) 1-DEOXY ANALOGS OF 1,25-DIHYDROXYVITAMIN D3 COMPOUNDS

(75) Inventors: Gary H. Posner, Baltimore, MD (US); Lindsey C. Hess, Pflugerville, TX (US); Alvin S. Kalinda, Bloomington, IN (US); Rachel D. Slack, Baltimore, MD (US); Uttam Saha, Thornhill (CA); P. Martin Petkovich, Kingston (CA)

(73) Assignees: JOHNS HOPKINS UNIVERSITY, Baltimore, MD (US); OPKO IRELAND GLOBAL HOLDINGS, LTD., Grand Cayman (KY)

( * ) Notice: Subject to any disclaimer, the term of this patent is extended or adjusted under 35 U.S.C. 154(b) by 0 days.

(21) Appl. No.: 13/521,980

(22) PCT Filed: Jan. 13, 2011

(86) PCT No.: PCT/US2011/021129
§ 371 (c)(1),
(2), (4) Date: Mar. 5, 2013

(87) PCT Pub. No.: WO2011/088209
PCT Pub. Date: Jul. 21, 2011

(65) Prior Publication Data
US 2013/0157987 A1 Jun. 20, 2013

Related U.S. Application Data

(60) Provisional application No. 61/294,741, filed on Jan. 13, 2010.

(51) Int. Cl.
*A61K 45/06* (2006.01)
*C07C 401/00* (2006.01)
*A61K 31/593* (2006.01)

(52) U.S. Cl.
CPC ............ *A61K 45/06* (2013.01); *A61K 31/593* (2013.01); *C07C 401/00* (2013.01); *C07C 2601/14* (2017.05); *C07C 2602/24* (2017.05)

(58) Field of Classification Search
None
See application file for complete search history.

(56) References Cited

U.S. PATENT DOCUMENTS

| 6,982,258 | B2 | 1/2006 | Posner et al. | |
| 7,101,865 | B2 | 9/2006 | Posner et al. | |
| 7,973,024 | B2 * | 7/2011 | Posner et al. | 514/167 |
| 2004/0224930 | A1 | 11/2004 | Posner et al. | |

FOREIGN PATENT DOCUMENTS

WO   WO-03/106411 A1   12/2003

OTHER PUBLICATIONS

Hsu et al. (Cancer Research 61, 2852-2856, Apr. 1, 2001).*
Cancer Drug Design and Discovery Neidle, Stephen, ed. (Elsevier/Academic Press, 2008) pp. 427-431.*
Fukuoka et al., Tacalcitol, an active vitamin D3, induces nerve growth factor production in human epidermal keratinocytes, Skin Pharmacol. Appl. Physiol., 14(4):226-33 (2001). [Abstract Only].
Adachi et al., A novel lyn-binding peptide inhibitor blocks eosinophil differentiation, survival, and airway eosinophilic inflammation, J. Immunol., 163:939 (1999).
Bouillon et al., Structure-function relationships in the vitamin D endocrine system, Endocr. Rev., 16(2):200-57 (1995).
Carlberg, Molecular basis of the selective activity of vitamin D analogues, J. Cell Biochem., 88(2):274-81 (2003).
Enk, T-cell receptor mimic peptides and their potential application in T-cell mediated disease, Int. Archives Allergy Immunology, 123:275-81 (2000).
Grzywacz et al., Methyl substitution of the 25-hydroxy group on 2-methylene-19-nor-1alpha.25-dihydroxyvitamin D3 (2MD) reduces potency but allows bone selectivity, Arch. Biochem. Biophys., 260(2):274-84 (2007).
Helvig et al., Dysregulation of renal vitamin D metabolism in the uremic rat, Kidney Int., 78(5):463-72 (2010).
International Search Report and Written Opinion for corresponding International application No. PCT/US2011/021129, dated Jun. 9, 2011.
Kahraman et al., Potent, selective and low-calcemic inhibitors of CYP24 hydroxylase: 24-sulfoxime analogues of the hormone 1 alpha,25-D-hidroxyvitamin D3, J. Med. Chem., 42:6854-63 (2004).
Kasyapa et al., Regulation of IL-15-stimulated TNF-alpha production by rolipram, J. Immunol., 163:2836-43 (1999).
Kidney Disease Outcomes Quality Inititiative (K/DOQI) Clinical Practice Guidelines for Bone Metabolism and Disease in Chronic Kidney Disease, Am. J. Kidney Dis., 42:S1-S202 (2003).
Kutner et al., Synthesis of retiferol RAD1 and RAD2, the lead representatives of a new class of des-CD analogs of cholecalciferol, Bioorg. Chem., 23:22-32 (1995).
Mathieu et al., The coming of age of 1,25-dihydroxyvitamin D(3) analogs as immunomodulatory agents, Trends Mol. Med., 8(4):174-9 (2002).
Nagpal et al., Vitamin D analogs: mechanism of action and therapeutic applications, Curr. Med. Chem., 8(13):1661-79 (2001).
National Institutes of Health, Office of Dietary Supplements, Dietary Supplement Fact Sheet: Vitamin D (2005).
Perez-Sestelo et al., A short, flexible approach to vitamin D3 analogues with modified side chains, Tetrahedron Lett., 35(2):275-8 (1994).
Perlman et al., Novel synthesis of 19-nor-vitamin D compounds, Tetrahedron Lett., 32(52):7663-6 (1991).
Pinette et al., Vitamin D receptor as a drug discovery target, Mini Rev. Med. Chem., 3(3):193-204 (2003).

(Continued)

*Primary Examiner* — Kortney L Klinkel
*Assistant Examiner* — William Lee
(74) *Attorney, Agent, or Firm* — Marshall, Gerstein & Borun LLP

(57) ABSTRACT

This present disclosure is directed to novel prodrugs of activated vitamin D3 compounds. The prodrugs can be designed to have one or more beneficial properties, such as selective inhibition of the enzyme CYP24, low calcemic activity, and anti-proliferative activity. Specifically, these prodrugs are 1-deoxy prohormones of active Vitamin D analogs, e.g. analogs of calcitriol. This disclosure is also directed to pharmaceutical and diagnostic compositions containing the prodrugs of the invention, and to their medical use, particularly as prodrugs in the treatment and/or prevention of diseases.

17 Claims, 18 Drawing Sheets

(56) References Cited

OTHER PUBLICATIONS

Posner et al., Conceptually new sulfone analogues of the hormone 1 alpha, 25-dihydroxyvitamin D(3): synthesis and preliminary biological evaluation, J. Med. Chem., 42(18):3425-35 (1999).

Posner et al., Potent, low-calcemic, selective inhibitors of CYP24 hydroxylase: 24-sulfone analogs of the hormone 1 alpha,25-dihydroxyvitamin D3, J. Steroid Biochem. Mol. Biol., 89-90: 5-12 (2004).

Ruckert, Inhibition of keratinocyte apoptosis by IL-15: a new parameter in the pathegenosis of psoriasis, J. Immunol., 165:2240-50 (2000).

Stein et al., An update on the therapeutic potential of vitamin D analogues, Expert Opin. Investig. Drugs, 12(5):825-40 (2003).

Toh et al., Studies on a convergent route to side-chain analogues of vitamin D: 25-hydroxy-23-oxavitamin $D_3$, J. Org. Chem., 48:1414-17 (1983).

Vieth, What is the optimal vitamin D status for health?, Prog. Biophys. Mol. Biol., 92(1):26-32 (2006).

Beer et al., High-dose calcitriol and carboplatin in metastatic androgen-independent prostate cancer, Am. J. Clin. Oncol., 27(5):535-41 (2004).

Beer et al., Weekly high-dose calcitriol and docetaxel in metastatic androgen-independent prostate cancer, J. Clin. Oncol., 21(1):123-8 (2003).

Colston et al., Vitamin D receptors and anti-proliferative effects of vitamin D derivatives in human pancreatic carcinoma cells in vivo and in vitro, Br. J. Can., 76(8)1017-20 (1997).

Fujioka et al., Inhibition of tumor growth and angiogenesis by vitamin D3 agents in murine renal cell carcinoma, J. Urol., 160(1):247-51 (1998).

Huerta et al., 1alpha,25-(OH)(2)-D(3) and its synthetic analogue decrease tumor load in the Apc(min) Mouse, Cancer Res., 62:741-746 (2002).

Iseki et al., Inhibition of angiogenesis as a mechanism for inhibition by 1alpha-hydroxyvitamin D3 and 1,25-dihydroxyvitamin D3 of colon carcinogenesis induced by azoxymethane in Wistar rats, Int. J. Can., 81:730-3 (1999).

Jones et al., Hepatic activation and inactivation of clinically-relevant vitamin D analogs and prodrugs, Antican. Res., 26:2589-96 (2006).

Jones et al., Current understanding of the molecular actions of vitamin D, Physiol. Rev., 78:1193-231 (1998).

Kusudo et al., Metabolism of 20-epimer of 1 alpha,25-dihydroxyvitamin D3 by CYP24: species-based difference between humans and rats, Biochem. Biophys. Res. Comm., 309:885-92 (2003).

Kusudo et al., Metabolism of A-ring diastereomers of 1 alpha,25-dihydroxyvitamin D3 by CYP24A1, Biochem. Biophys. Res. Comm., 321:774-82 (2004).

Masood et al., Kaposi sarcoma is a therapeutic target for vitamin D(3) receptor agonist, Blood, 96(9):3188-94 (2000).

Morris et al., High-dose calcitriol, zoledronate, and dexamethasone for the treatment of progressive prostate carcinoma, Cancer, 100(9)1868-75 (2004).

Parise et al., CYP24, the enzyme that catabolizes the antiproliferative agent vitamin D, is increased lung cancer, Int. J. Cancer., 119:1819-28 (2006).

Rao et al., Vitamin D receptor and p21/WAF1 are targets of genistein and 1, 25-dihydroxyvitamin D3 in human prostate cancer cells, Can. Res., 64:2143-7 (2004).

Sakaki et al., Metabolism of 26,26,26,27,27,27-F6-1alpha,25-dihydroxyvitamin D3 by CYP24: species-based difference between humans and rats, Biochem. Pharmacol., 65:1957-65 (2003).

Shankar et al., In vitro metabolism of 19-nor-1alpha, 25-(OH)2D2 in cultured cell lines: inducible synthesis of lipid- and water-soluble metabolites, Arch. Biochem. Biophy., 387(2):297-306 (2001).

Shevde et al., A potent analog of 1alpha,25-dihydroxyvitamin D3 selectively induces bone formation, Proc. Natl. Acad. Sci. USA, 99:13487-91 (2002).

Sicinski et al., New 1alpha,25-dihydroxy-19-norvitamin D3 compounds of high biological activity: synthesis and biological evaluation of 2-hydroxymethyl, 2-methyl, and 2-methylene analogues, J. Med. Chem. 41:4662-74 (1998).

Trump et al., Phase II trial of high-dose, intermittent calcitriol (1,25 dihydroxyvitamin D3) and dexamethasone in androgen-independent prostate cancer, Can., 106(10):2136-212 (2006).

Trydal et al., 1,25-Dihydroxyvitamin D3 receptor measurement in primary renal cell carcinomas and autologous normal kidney tissue, Can. Res., 48:2458-61 (1988).

Zhou et al., Vitamin D is associated with improved survival in early-stage non-small cell lung cancer patients, Cancer Epidemiol Biomarkers Prev., 14(10):2303-9 (2005).

* cited by examiner

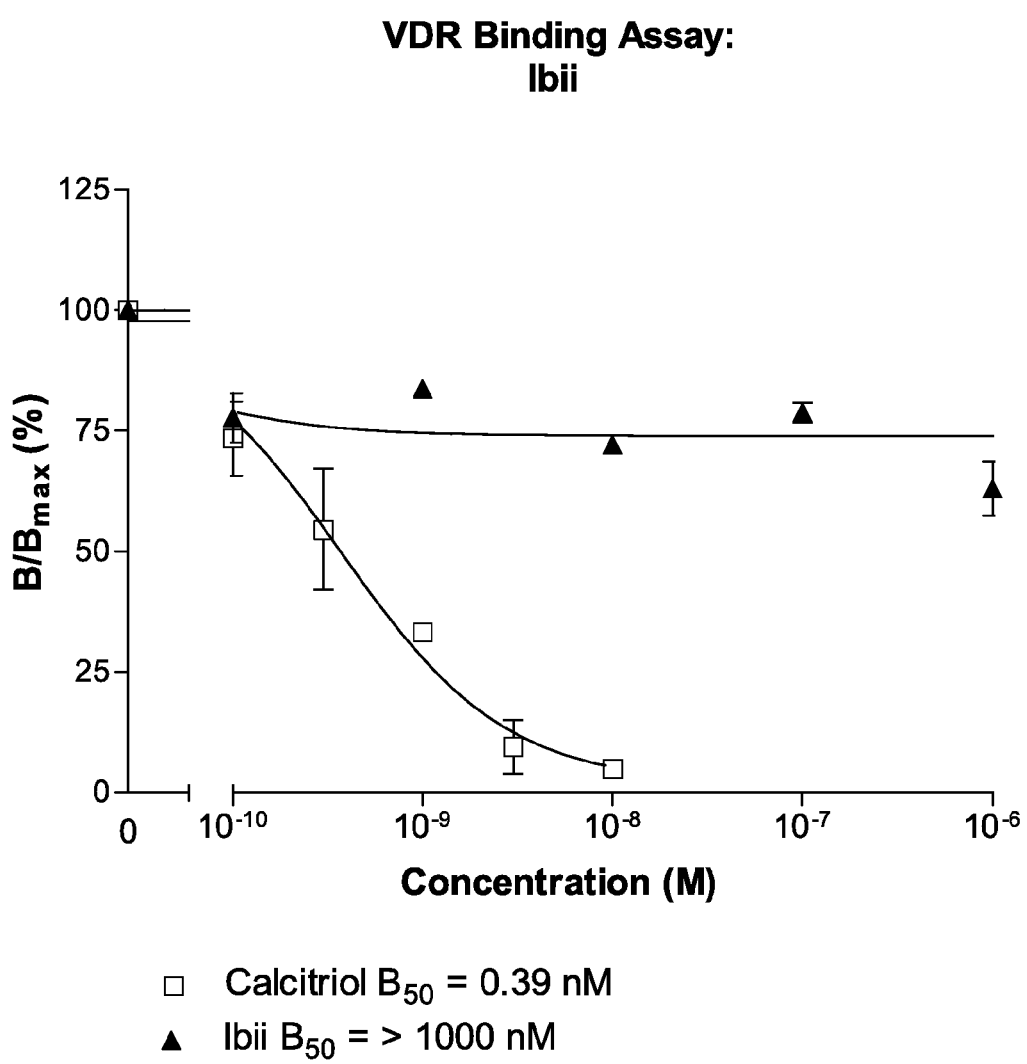

1-DEOXY ANALOGS OF 1,25-DIHYDROXYVITAMIN D3 COMPOUNDS

CROSS-REFERENCE TO RELATED APPLICATIONS

The benefit under 35 U.S.C. §119(e) of U.S. Provisional Patent Application Ser. No. 61/294,741 filed on Jan. 13, 2010 is hereby claimed.

STATEMENT OF U.S. GOVERNMENT INTEREST

This invention was made in part with U.S. government support under the National Institutes of Health Grant No. CA 93547. The government has certain rights in this invention.

BACKGROUND

Field of the Disclosure

This disclosure relates generally to novel prodrugs of vitamin D-related compounds. In particular, the disclosure includes 1-deoxy prohormones of active Vitamin D hormones, e.g. analogs of calcitriol, and 1-deoxy analogs of CYP24 inhibitors, pharmaceutical and diagnostic compositions containing them, and to their medical use, particularly as prodrugs in the treatment and/or prevention of diseases.

Brief Description of Related Technology

"Vitamin D" is a term that refers broadly to the organic substances named Vitamin $D_2$, Vitamin $D_3$, Vitamin $D_4$, etc., and to their metabolites and hormonal forms that influence calcium and phosphorus homeostasis.

The most widely recognized forms of Vitamin D are Vitamin $D_2$ (ergocalciferol) and Vitamin $D_3$ (cholecalciferol). Vitamin $D_2$ is produced in plants from ergosterol during sunlight exposure and is present, to a limited extent, in the human diet. Vitamin $D_3$ is generated from 7-dehydrocholesterol in human skin during exposure to sunlight and also is found, to a greater extent than Vitamin $D_2$, in the human diet, principally in dairy products (milk and butter), certain fish and fish oils, and egg yolk. Vitamin D supplements for human use consist of either Vitamin $D_2$ or Vitamin $D_3$.

Both Vitamin $D_2$ and Vitamin $D_3$ are metabolized into prohormones by one or more enzymes located in the liver. The involved enzymes are mitochondrial and microsomal cytochrome P450 (CYP) isoforms, including CYP27A1, CYP2R1, CYP3A4, CYP2J3 and possibly others. These enzymes metabolize Vitamin $D_2$ into two prohormones known as 25-hydroxyvitamin $D_2$ and 24(S)-hydroxyvitamin $D_2$, and Vitamin $D_3$ into a prohormone known as 25-hydroxyvitamin $D_3$. The two 25-hydroxylated prohormones are more prominent in the blood, and can be collectively referred to as "25-hydroxyvitamin D." Vitamin $D_2$ and Vitamin $D_3$ can be metabolized into their respective prohormones outside of the liver in certain epithelial cells, such as enterocytes, which contain the same (or similar) enzymes, but extrahepatic prohormone production probably contributes little to blood levels of 25-hydroxyvitamin D.

The rates of hepatic and extrahepatic production of the Vitamin D prohormones are not tightly regulated, and they vary mainly with intracellular concentrations of the precursors (Vitamin $D_2$ and Vitamin $D_3$). Higher concentrations of either precursor increase prohormone production, while lower concentrations decrease production. Hepatic production of prohormones is inhibited by high levels of 25-hydroxyvitamin D via a poorly understood mechanism apparently directed to prevention of excessive blood prohormone levels.

The Vitamin D prohormones are further metabolized in the kidneys into potent hormones by an enzyme known as CYP27B1 (or 25-hydroxyvitamin $D_3$-1α-hydroxylase) located in the proximal kidney tubule. The prohormones 25-hydroxyvitamin $D_2$ and 24(S)-hydroxyvitamin $D_2$ are metabolized into hormones known as 1α,25-dihydroxyvitamin $D_2$ and 1α,24(S)-dihydroxyvitamin $D_2$. Likewise, 25-hydroxyvitamin $D_3$ is metabolized into a hormone known as 1α,25-dihydroxyvitamin $D_3$ (or calcitriol). These hormones are released by the kidneys into the blood for systemic delivery. The two 1α,25-dihydroxylated hormones, usually far more prominent in the blood than 1α,24(S)-dihydroxyvitamin $D_2$, can be collectively referred to as "1,25-dihydroxyvitamin D." Vitamin D prohormones can be metabolized into hormones outside of the kidneys in keratinocytes, lung epithelial cells, enterocytes, cells of the immune system (e.g., macrophages) and certain other cells containing CYP27B1 or similar enzymes, but such extrarenal hormone production is incapable of sustaining normal blood levels of 1,25-dihydroxyvitamin D in advanced chronic kidney disease (CKD).

Blood levels of 1,25-dihydroxyvitamin D are precisely regulated by a feedback mechanism which involves parathyroid hormone (PTH). The renal 1α-hydroxylase (or CYP27B1) is stimulated by PTH and inhibited by 1,25-dihydroxyvitamin D. When blood levels of 1,25-dihydroxyvitamin D fall, the parathyroid glands sense this change via intracellular Vitamin D receptors (VDR) and secrete PTH. The secreted PTH stimulates expression of renal CYP27B1 and, thereby, increases production of Vitamin D hormones. As blood concentrations of 1,25-dihydroxyvitamin D rise again, the parathyroid glands attenuate further PTH secretion. As blood PTH levels fall, renal production of Vitamin D hormones decreases. Rising blood levels of 1,25-dihydroxyvitamin D also directly inhibit further Vitamin D hormone production by CYP27B1.

PTH secretion can be abnormally suppressed in situations in which blood 1,25-dihydroxyvitamin D concentrations become excessively elevated, as can occur in certain disorders such as sarcoidosis or as a result of bolus doses of Vitamin D hormone replacement therapies. Oversuppression of PTH secretion can cause or exacerbate disturbances in calcium homeostasis. The parathyroid glands and the renal CYP27B1 are exquisitely sensitive to changes in blood concentrations of Vitamin D hormones so that serum 1,25-dihydroxyvitamin D is tightly controlled, fluctuating up or down by less than 20% during any 24-hour period. In contrast to renal production of Vitamin D hormones, extrarenal production is not under precise feedback control.

Blood levels of 1,25-dihydroxyvitamin D and substrate 25-hydroxyvitamin D prohormone, and regulation thereof, can also be affected by vitamin D hormone analogs, such as 19-nor-1,25 dihydroxyvitamin $D_2$ and 22-oxacalcitriol, the prodrugs 1α-hydroxyvitamin $D_2$ and 1α-hydroxyvitamin $D_2$, 24-sulfoximine vitamin $D_3$ compounds, oxime analogs of 1α,25-dihydroxyvitamin $D_3$, and 25-$SO_2$ substituted analogs of 1α,25-dihydroxyvitamin $D_3$, as disclosed in U.S. Pat. No. 7,101,865, U.S. Pat. No. 6,982,258, and U.S. Patent Application No. 2004/0224930, respectively, which are hereby incorporated by reference.

The Vitamin D hormones have essential roles in human health which are mediated by the intracellular VDR. In particular, the Vitamin D hormones regulate blood calcium levels by controlling intestinal absorption of dietary calcium and reabsorption of calcium by the kidneys. Excessive hormone levels can lead to abnormally elevated urine calcium (hypercalciuria), blood calcium (hypercalcemia) and blood phosphorus (hyperphosphatemia). Vitamin D deficiency, on the other hand, is associated with secondary hyperparathyroidism, parathyroid gland hyperplasia, hypocalcemia, CKD, and metabolic bone diseases such as osteitis fibrosa cystica, osteomalacia, rickets, osteoporosis, and extraskeletal calcification. Further, Vitamin D hormones are required for the normal functioning of the musculoskeletal, immune and renin-angiotensin systems. Numerous other roles for Vitamin D hormones are being postulated and elucidated, based on the documented presence of intracellular VDR in nearly every human tissue. For example, vitamin D has been postulated to play a role in cellular differentiation and cancer, in regulation of the immune system (immune enhancing or immune suppressing effects, depending on the situation), atherosclerosis, growth and normal bone formation and metabolism. Vitamin D deficiency increases the risk of many common cancers, multiple sclerosis, rheumatoid arthritis, hypertension, cardiovascular heart disease, blood pressure, antifibrosis, red blood cell formation, hair growth, and type I diabetes.

The actions of Vitamin D hormones on specific tissues depend on the degree to which they bind to (or occupy) the intracellular VDR in those tissues. VDR binding increases as the intracellular concentrations of the hormones rise, and decreases as the intracellular concentrations fall. In all cells, intracellular concentrations of the Vitamin D hormones change in direct proportion to changes in blood hormone concentrations. In cells containing CYP27B1 (or similar enzymes), intracellular concentrations of the Vitamin D hormones also change in direct proportion to changes in blood and/or intracellular prohormone concentrations, as discussed above.

Vitamin $D_2$, Vitamin $D_3$ and their prohormonal forms have affinities for the VDR which are estimated to be at least 100-fold lower than those of the active Vitamin D hormones and do not effectively activate the receptor. As a consequence, physiological concentrations of these hormone precursors exert little, if any, biological actions without prior metabolism to active Vitamin D hormones. However, supraphysiological levels of these hormone precursors, especially the prohormones, in the range of 10 to 1,000 fold higher than normal, can sufficiently occupy the VDR and exert actions like the Vitamin D hormones.

Blood levels of Vitamin $D_2$ and Vitamin $D_3$ are normally present at stable concentrations in human blood, given a sustained, adequate supply of Vitamin D from sunlight exposure and an unsupplemented diet. Slight, if any, increases in blood Vitamin D levels occur after meals since unsupplemented diets have low Vitamin D content, even those containing foods fortified with Vitamin D. The Vitamin D content of the human diet is so low that the National Institutes of Health (NIH) cautions "it can be difficult to obtain enough Vitamin D from natural food sources" [NIH, Office of Dietary Supplements, Dietary Supplement Fact Sheet: Vitamin D (2005)]. Almost all human Vitamin D supply comes from fortified foods, exposure to sunlight or from dietary supplements, with the last source becoming increasingly important. Blood Vitamin D levels rise only gradually, if at all, after sunlight exposure since cutaneous 7-dehydrocholesterol is modified by UV radiation to pre-Vitamin $D_3$ which undergoes thermal conversion in the skin to Vitamin $D_3$ over a period of several days before circulating in the blood.

Blood Vitamin D hormone concentrations also remain generally constant through the day in healthy individuals, but can vary significantly over longer periods of time in response to seasonal changes in sunlight exposure or sustained alterations in Vitamin D intake. Marked differences in normal Vitamin D hormone levels are commonly observed between healthy individuals, with some individuals having stable concentrations as low as approximately 20 pg/mL and others as high as approximately 70 pg/mL. Due to this wide normal range, medical professionals have difficulty interpreting isolated laboratory determinations of serum total 1,25-dihydroxyvitamin D; a value of 25 pg/mL may represent a normal value for one individual or a relative deficiency in another.

Transiently low blood levels of 1,25-dihydroxyvitamin D stimulate the parathyroid glands to secrete PTH for brief periods ending when normal blood Vitamin D hormone levels are restored. In contrast, chronically low blood levels of 1,25-dihydroxyvitamin D continuously stimulate the parathyroid glands to secrete PTH, resulting in a disorder known as secondary hyperparathyroidism. Chronically low hormone levels also decrease intestinal calcium absorption, leading to reduced blood calcium concentrations (hypocalcemia) which further stimulate PTH secretion. Continuously stimulated parathyroid glands become increasingly hyperplastic and eventually develop resistance to regulation by vitamin D hormones. Without early detection and treatment, secondary hyperparathyroidism progressively increases in severity, causing debilitating metabolic bone diseases, including osteoporosis and renal osteodystrophy.

Chronically low blood levels of 1,25-dihydroxyvitamin D can develop when there is insufficient renal CYP27B1 to produce the required supply of Vitamin D hormones, a situation which can arise in late stage CKD. The activity of renal CYP27B1 declines as the Glomerular Filtration Rate (GFR) falls below approximately 60 ml/min/1.73 $m^2$ due to the loss of functioning nephrons. In end-stage renal disease (ESRD), when the kidneys fail completely and hemodialysis is required for survival, renal CYP27B1 often becomes altogether absent. Any remaining CYP27B1 is greatly inhibited by elevated serum phosphorous (hyperphosphatemia) caused by inadequate renal excretion of dietary phosphorous. Recently, however, it has been demonstrated that in earlier stages of CKD, blood levels of 1,25-dihydroxyvitamin D can be low, even when CYP27B1 expression is normal. Without intending to be bound by any particular theory, it is possible that disease related expression of CYP24A1 in kidney may be responsible for the decreased vitamin D status in such patients. We have therefore developed compounds which can take advantage of the residual CYP27B to generate sufficient vitamin D hormone to control the symptoms of CKD.

Chronically low blood levels of 1,25-dihydroxyvitamin D also develop because of a deficiency of Vitamin D prohormones, since renal hormone production cannot proceed without the required precursors. Prohormone production declines markedly when cholecalciferol and ergocalciferol are in short supply, a condition often described by terms such as "Vitamin D insufficiency," "Vitamin D deficiency," or "hypovitaminosis D." Therefore, measurement of 25-hydroxyvitamin D levels in blood has become the accepted method among healthcare professionals to monitor Vitamin D status. Recent studies have documented that the great majority of CKD patients have low blood levels of 25-hydroxyvitamin D, and that the prevalence of Vitamin D insufficiency and deficiency increases as CKD progresses.

The National Kidney Foundation (NKF) has recently focused the medical community's attention on the need for early detection and treatment of secondary hyperparathyroidism by publishing Kidney Disease Outcomes Quality Initiative (K/DOQI) Clinical Practice Guidelines for Bone Metabolism and Disease in Chronic Kidney Disease [*Am. J. Kidney Dis.* 42:S1-S202, 2003)]. The K/DOQI Guidelines identified the primary etiology of secondary hyperparathyroidism as chronically low blood levels of 1,25-dihydroxyvitamin D and recommended regular screening in CKD Stages 3 through 5 for elevated blood PTH levels relative to Stage-specific PTH target ranges. CKD Stage 3 was defined as moderately decreased kidney function (GFR of 30-59 mL/min/1.73 m$^2$) with an intact PTH (iPTH) target range of 35-70 pg/mL; Stage 4 was defined as severely decreased kidney function (GFR of 15-29 mL/min/1.73 m$^2$), with an iPTH target range of 70-110 pg/mL; and Stage 5 was defined as kidney failure (GFR of <15 mL/min/1.73 m$^2$ or dialysis) with an iPTH target range of 150-300 pg/mL. In the event that screening revealed an iPTH value to be above the ranges targeted for CKD Stages 3 and 4, the Guidelines recommended a follow-up evaluation of serum total 25-hydroxyvitamin D to detect possible Vitamin D insufficiency or deficiency. If 25-hydroxyvitamin D levels below 30 ng/mL was observed, the recommended intervention was Vitamin D repletion therapy using orally administered ergocalciferol. If 25-hydroxyvitamin D levels above 30 ng/mL was observed, the recommended intervention was Vitamin D hormone replacement therapy using known oral or intravenous Vitamin D hormones or analogs.

The NKF K/DOQI Guidelines defined Vitamin D sufficiency as serum 25-hydroxyvitamin D levels ≥30 ng/mL. Recommended Vitamin D repletion therapy for patients with "Vitamin D insufficiency," defined as serum 25-hydroxyvitamin D of 16-30 ng/mL, was 50,000 IU per month of oral Vitamin D$_2$ for 6 months, given either in single monthly doses or in divided doses of approximately 1,600 IU per day. Recommended repletion therapy for patients with "Vitamin D deficiency" was more aggressive: for "mild" deficiency, defined as serum 25-hydroxyvitamin D of 5-15 ng/mL, the Guidelines recommended 50,000 IU per week of oral Vitamin D$_2$ for 4 weeks, followed by 50,000 IU per month for another 5 months; for "severe" deficiency, defined as serum 25-hydroxyvitamin D below 5 ng/mL, the Guidelines recommended 50,000 IU/week of oral Vitamin D$_2$ for 12 weeks, followed by 50,000 IU/month for another 3 months. Doses of 50,000 IU per week are approximately equivalent to 7,000 IU per day.

As previously described, Vitamin D hormone replacement therapy is used to treat or prevent vitamin D insufficiency or deficiency in patients. Activated Vitamin D, particularly 1α,25-dihydroxyvitamin D$_3$ (calcitriol), is especially perceived as a valuable therapeutic agent to treat vitamin D insufficiency or deficiency, as well as for a wide range of maladies such as metabolic bone disease, osteoporosis, psoriasis, psoriatic arthritis, colon, prostate and breast cancer, and HIV infection.

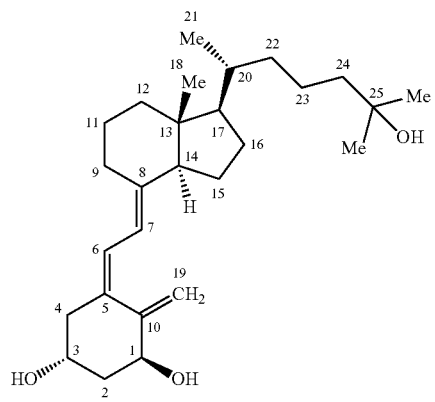 [SMILES: C=C1/C(=C\C=C2/CCC[C@]3(C)[C@@H]([C@H](C)CCCC(C)(C)O)CC[C@@H]23)C[C@@H](O)C[C@@H]1O]

1α,25-Dihydroxyvitamin D$_3$ (Calcitriol)

However, administration of 1α,25-dihydroxyvitamin D$_3$ often results in the development of hypercalcemia as a side effect, often before the desired therapeutic effect is obtained, and thus prevents sustained systemic administration.

Analogs of 1α,25-dihydroxyvitamin D$_3$ have been developed that selectively exhibit desirable pharmacological activities but do not exhibit hypercalcemic and other undesirable effects to the same extent. These sulfoximine, oxime, and sulfone analogs of 1α,25-dihydroxyvitamin D$_3$ are low calcemic and anti-proliferative, and some also show selective inhibition of the cytochrome P450 enzyme CYP24, as disclosed in U.S. Pat. No. 7,101,865, U.S. Pat. No. 6,982,258, and U.S. Patent Application No. 2004/0224930.

CYP24 catalyzes the first step in the catabolism of various vitamin D compounds. In particular, for example, CYP24 carries out the conversion of 25-hydroxyvitamin D$_3$ to 24,25-dihydroxyvitamin D$_3$ and the conversion of 1,25-dihydroxyvitamin D$_3$ (calcitriol) to 1,24,25-trihydroxyvitamin D$_3$ eventually giving rise to calcitroic acid. CYP24 can also hydroxylate at the 23 position, resulting in the production of the terminal metabolite 1,25-dihydroxyvitamin D$_3$-26,23-lactone. Further processing by Phase II catabolic enzymes ultimately leads to clearance of vitamin D compounds from the body. Inhibiting catabolism by CYP24 is expected to lengthen the biological lifetime of the Vitamin D hormones and thus to allow smaller amounts of them to be used. Further, inhibition of catabolism by CYP24 increases the endogenous levels of vitamin D hormones, which provides beneficial therapeutic effects.

SUMMARY

This present disclosure is directed to novel prodrugs of vitamin D-related compounds. In various optional embodiments, the prodrugs can have one or more additional benefits, including selective inhibition of the enzyme CYP24, low calcemic profile, and anti-proliferative. This disclosure is also directed to pharmaceutical and diagnostic compositions containing the prodrugs of the invention, and to their medical use, particularly as prodrugs in the treatment and/or prevention of diseases.

In one aspect, the invention provides a compound of Formula I, or a pharmaceutically acceptable salt, solvate, or hydrate thereof:

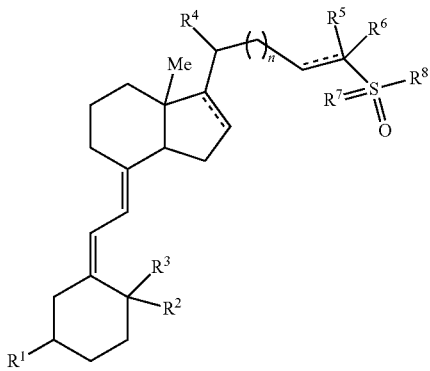

Formula I wherein each --- independently is a single bond or a double bond;
n is 0, 1 or 2;
$R^1$ is selected from the group consisting of OH, $OC_{1-6}$alkyl, and halo;
$R^2$ and $R^3$ are each independently H or halo, or together form $=CH_2$;
$R^4$ is $C_{1-6}$alkyl;
$R^5$ and $R^6$ are each independently H, halo, $C_{1-4}$alkyl, or can be taken, together with the carbon atom to which they are bound, to form a $C_{3-6}$cycloalkyl ring, with the proviso that when --- between carbon-23 and carbon-24 is a double bond, then $R^5$ is absent;
$R^7$ is selected from the group consisting of O, NH, N($C_{1-6}$alkyl), and NC(O)$R^9$;
$R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo, OH, $OCF_3$, SH, $SC_{1-4}$alkyl, $NH_2$, $NHC_{1-4}$alkyl, $N(C_{1-4}$alkyl)($C_{1-4}$alkyl), and CN; and
$R^9$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo.

In another aspect, the invention provides a compound of Formula II, or a pharmaceutically acceptable salt, solvate, or hydrate thereof:

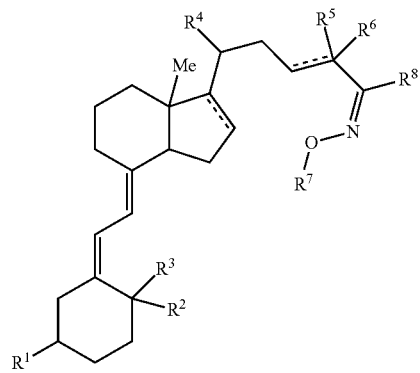

Formula II wherein each --- independently is a single bond or a double bond;

$R^1$ is selected from the group consisting of OH, $OC_{1-6}$alkyl, and halo;
$R^2$ and $R^3$ are each independently H or halo, or together form $=CH_2$;
$R^4$ is $C_{1-6}$alkyl;
$R^5$ and $R^6$ are each independently H, halo, $C_{1-4}$alkyl, or can be taken, together with the carbon atom to which they are bound, to form a $C_{3-6}$cycloalkyl ring, with the proviso that when --- between carbon-23 and carbon-24 is a double bond, then $R^5$ is absent;
$R^7$ is selected from the group consisting of H, $C_{1-6}$alkyl, $C_{2-6}$alkenyl, aryl and heteroaryl, with $C_{1-6}$alkyl and $C_{2-6}$alkenyl being unsubstituted or substituted with 1 to 4 groups independently selected from $C_{1-4}$alkyl, $C_{2-4}$alkenyl, $OC_{1-4}$alkyl, $OC_{2-4}$alkenyl, OH, halo, $NH_2$, $NHC_{1-4}$alkyl, $NHC_{2-4}$alkenyl, $N(C_{1-4}$alkyl)($C_{1-4}$alkyl), $N(C_{2-4}$alkenyl)($C_{1-4}$alkyl), and with aryl and heteroaryl being unsubstituted or substituted with 1 to 5 groups independently selected from $C_{1-4}$alkyl, $C_{2-4}$alkenyl, $OC_{1-4}$alkyl, $OC_{2-4}$alkenyl, OH, $CF_3$, $OCF_3$, halo, SH, $SC_{1-4}$alkyl, $SC_{2-4}$alkenyl $NH_2$, $NHC_{1-4}$alkyl, $NHC_{2-4}$alkenyl, $N(C_{1-4}$alkyl)($C_{1-4}$alkyl), $N(C_{2-4}$alkenyl)($C_{1-4}$alkyl)CN, C(O)OH, $C(O)OC_{1-4}$alkyl, $C(O)OC_{2-4}$alkenyl, $C(O)NHC_{1-4}$alkyl, $C(O)NHC_{2-4}$alkenyl, $NHC(O)C_{1-4}$alkyl, $NHC(O)C_{2-4}$alkenyl, $OC(O)C_{1-4}$alkyl, $OC(O)C_{2-4}$alkenyl, $SOC_{1-4}$alkyl, $SOC_{2-4}$alkenyl, $SO_2C_{1-4}$alkyl, $SO_2C_{2-4}$alkenyl, $SO_2NHC_{1-4}$alkyl, $SO_2NHC_{2-4}$alkenyl and $SO_2NH_2$; and
$R^8$ is selected from the group consisting of $C_{1-6}$alkyl, $C_{2-6}$alkenyl, cyclo($C_3$-$C_6$)alkyl, cyclo($C_5$-$C_6$)alkenyl, aryl, heteroaryl, aryl-$C_{1-6}$alkyl, aryl-$C_{2-6}$alkenyl, heteroaryl-$C_{1-6}$alkyl, and heteroaryl-$C_{2-6}$alkenyl with $C_{1-6}$alkyl and $C_{2-6}$alkenyl being unsubstituted or substituted with 1-4 groups independently selected from $C_{1-4}$alkyl, $C_{2-4}$alkenyl, $OC_{1-4}$alkyl, $OC_{2-4}$alkenyl, OH, halo, $NH_2$, $NHC_{1-4}$alkyl, $NHC_{2-4}$alkenyl, $N(C_{1-4}$alkyl)($C_{1-4}$alkyl), and $N(C_{2-4}$alkenyl)($C_{1-4}$alkyl), and with cyclo($C_3$-$C_6$)alkyl, cyclo($C_5$-$C_6$) alkenyl aryl, heteroaryl, aryl-$C_{1-6}$alkyl, aryl-$C_{2-6}$alkenyl, heteroaryl-$C_{1-6}$alkyl, heteroaryl-$C_{2-6}$alkenyl being unsubstituted or substituted with 1-5 groups independently selected from $C_{1-4}$alkyl, $C_{2-4}$alkenyl, $OC_{1-4}$alkyl, $OC_{2-4}$alkenyl, OH, $CF_3$, $OCF_3$, halo, SH, $SC_{1-4}$alkyl, $SC_{2-4}$alkenyl, $NH_2$, $NHC_{1-4}$alkyl, $NHC_{2-4}$alkenyl, $N(C_{1-4}$alkyl)($C_{1-4}$alkyl), $N(C_{2-4}$alkenyl)($C_{1-4}$alkyl), CN, C(O)OH, $C(O)OC_{1-4}$alkyl, $C(O)OC_{2-4}$alkenyl, $C(O)NHC_{1-4}$alkyl, $C(O)NHC_{2-4}$alkenyl, $NHC(O)C_{1-4}$alkyl, $NHC(O)C_{2-4}$alkenyl, $OC(O)C_{1-4}$alkyl, $OC(O)C_{2-4}$alkenyl, $SOC_{1-4}$alkyl, $SOC_{2-4}$alkenyl $SO_2C_{1-4}$alkyl, $SO_2C_{2-4}$alkenyl, $SO_2NHC_{1-4}$alkyl, $SO_2NHC_{2-4}$alkenyl and $SO_2NH_2$.

In another aspect, the invention provides a compound of Formula III, or a pharmaceutically acceptable salt, solvate, or hydrate thereof:

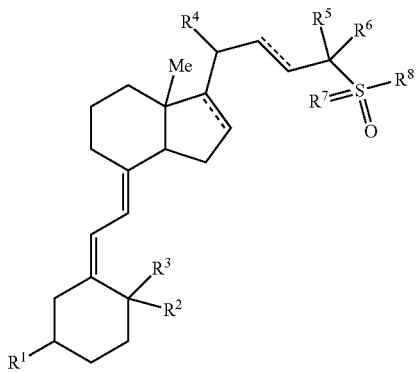

Formula III wherein each --- independently is a single bond or a double bond;

$R^1$ is selected from the group consisting of OH, $OC_{1-6}$alkyl, and halo;

$R^2$ and $R^3$ are each independently H or halo, or together form $=CH_2$;

$R^4$ is $C_{1-6}$alkyl;

$R^5$ and $R^6$ are each independently H, halo, $C_{1-4}$alkyl, or can be taken, together with the carbon atom to which they are bound, to form a $C_{3-6}$cycloalkyl ring;

$R^7$ is selected from the group consisting of O, NH, $N(C_{1-6}$alkyl$)$, and $NC(O)R^9$;

$R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo, OH, $OCF_3$, SH, $SC_{1-4}$alkyl, $NH_2$, $NHC_{1-4}$alkyl, $N(C_{1-4}$alkyl$)(C_{1-4}$alkyl$)$, and CN; and, $R^9$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo.

According to another aspect of the invention, there is provided a pharmaceutical composition comprising a prodrug of the invention in an admixture with a pharmaceutically-acceptable excipient, e.g. a diluent or carrier.

According to another aspect of the invention, there is provided a method for treating diseases which benefit from a modulation of the levels of 1α,25-dihydroxyvitamin $D_3$ comprising administering an effective amount of a compound of Formula I or II to a cell or animal in need thereof. The invention also includes the use of a compound of Formula I or II to modulate the levels of 1α,25-dihydroxyvitamin $D_3$.

According to another aspect of the invention, there is provided a method for treating diseases which benefit from inhibiting the catabolism of CYP24 substrates (e.g., 1α,25-dihydroxyvitamin $D_3$) comprising administering an effective amount of a CYP-24 inhibiting prodrug described herein (e.g., a compound of Formula I or II) to a cell or animal in need thereof. The invention also includes the use of such compounds to inhibit the catabolism of CYP24 substrates (e.g., 1α,25-dihydroxyvitamin $D_3$).

According to another aspect of the invention, there is provided a method of inhibiting the proliferation of a cancer cell comprising administering an effective amount of a vitamin D receptor agonist prodrug described herein (e.g., a compound of Formula I or II) to a cell or animal in need thereof. The invention also includes a use of such compounds to inhibit cancer cell proliferation.

According to another aspect of the invention, there is provided a method of modulating CYP24 activity in a cell or animal by administering an effective amount of a CYP-24 inhibiting prodrug described herein (e.g., a compound of Formula I or II). In a further aspect, the invention provides a method of modulating CYP24 activity, preferably inhibiting CYP24 activity by administering an effective amount of a compound of a CYP-24 inhibiting prodrug described herein (e.g., a compound of Formula I or II) to a cell or animal in need thereof. The present invention also provides a use of such compounds to modulate, preferably to inhibit, CYP24 activity.

According to another aspect of the invention, there is provided a method of increasing the efficacy of a vitamin D receptor agonist, preferably 1α,25-dihydroxyvitamin $D_3$ (calcitriol), comprising co-administering an effective amount of a CYP24 inhibitor prodrug described herein (e.g. a compound of Formula I or II) and an effective amount of the vitamin D receptor agonist, preferably 1α,25-dihydroxyvitamin $D_3$ (calcitriol).

For the composition and methods described herein, preferred steps, preferred components, preferred compositional ranges thereof, and preferred combinations of the foregoing, can be selected from the various examples provided herein.

Further aspects and advantages will be apparent to those of ordinary skill in the art from a review of the following detailed description, taken in conjunction with the drawings. While the compositions and methods are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

FIG. 1 is a graph showing the binding of Prodrug Ibii to the VDR compared to 1,25-dihydroxyvitamin $D_3$. Prodrug Ibii does not substantially bind to the VDR in vitro ($B_{50}$>1000 nM), while 1,25-dihydroxyvitamin $D_3$ has $B_{50}$=0.39 nM.

FIG. 2a shows the relative CYP24 expression in HPK1aRas cells treated with Prodrug Ibii compared to calcitriol at 100 nM. FIG. 2b shows the relative CYP24 expression in HPK1aRas cells treated with Prodrug Ibii compared to vehicle treated cells. FIG. 2c shows the relative CYP24 transcription in HPK1aRas cells treated with Prodrug Ibii compared to calcitriol, 25-hydroxyvitamin $D_3$, and the 1-hydroxy active form of Prodrug Ibii. FIG. 2d shows the relative CYP24 transcription in HPK1aRas cells treated with Prodrug Ibii compared to 25-hydroxyvitamin $D_3$ and the 1-hydroxy active form of Prodrug Ibii.

DETAILED DESCRIPTION

Figure 2A:
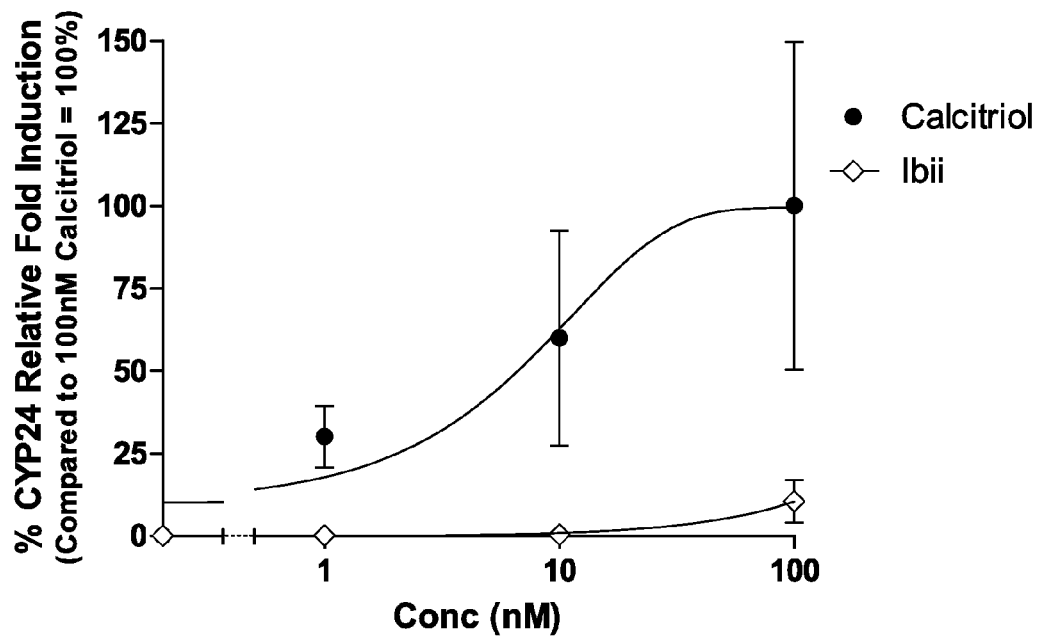
FIGS. 2a-2d are graphs showing the induction of transcription of CYP24 in HPK1aRas cells by Prodrug Ibii.
Figure 2B:
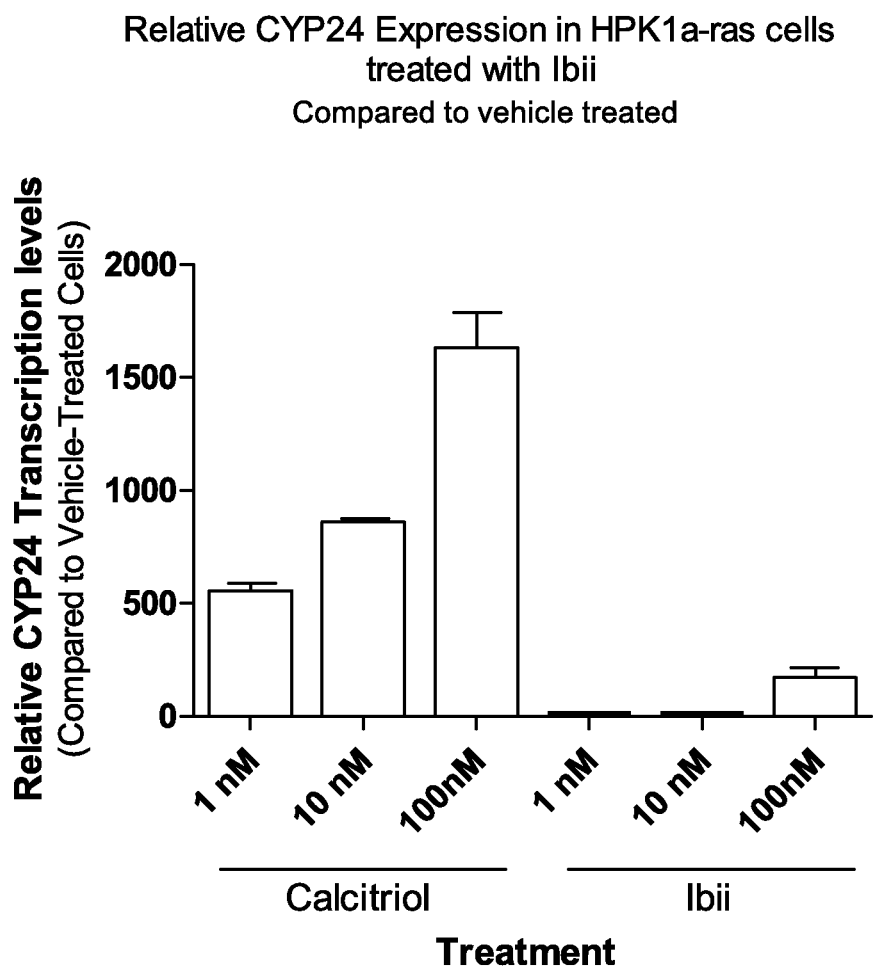
Figure 2C:
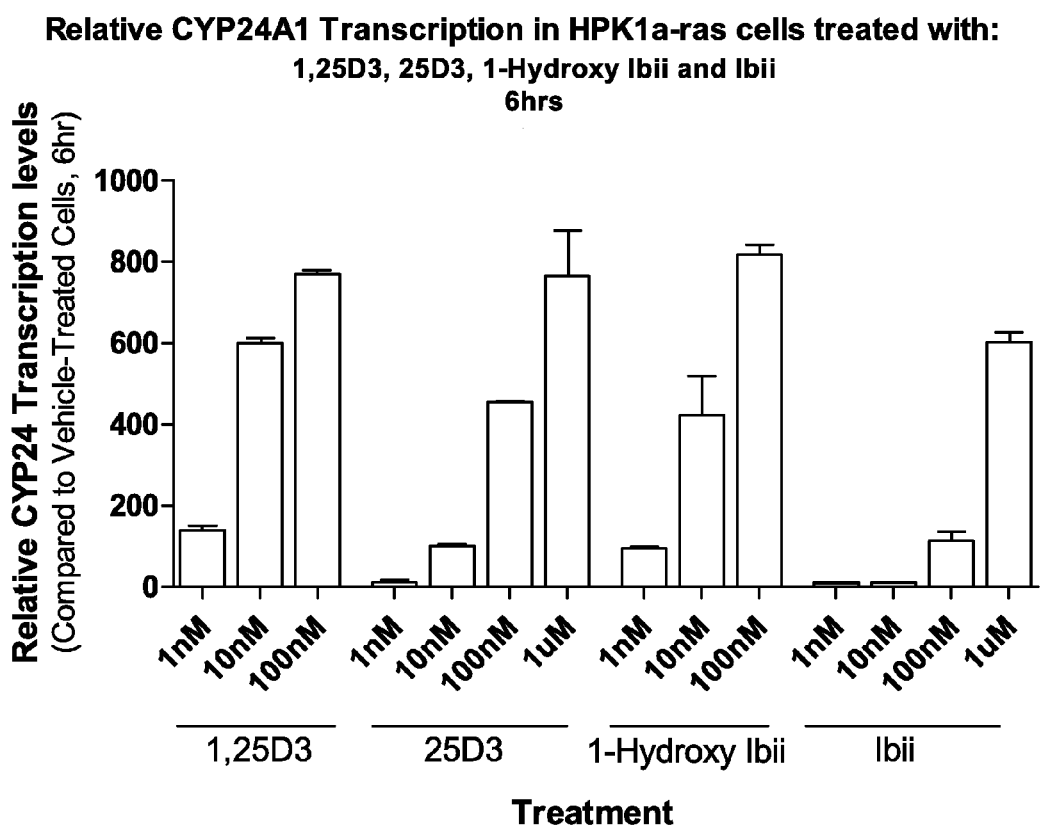
Figure 2D:
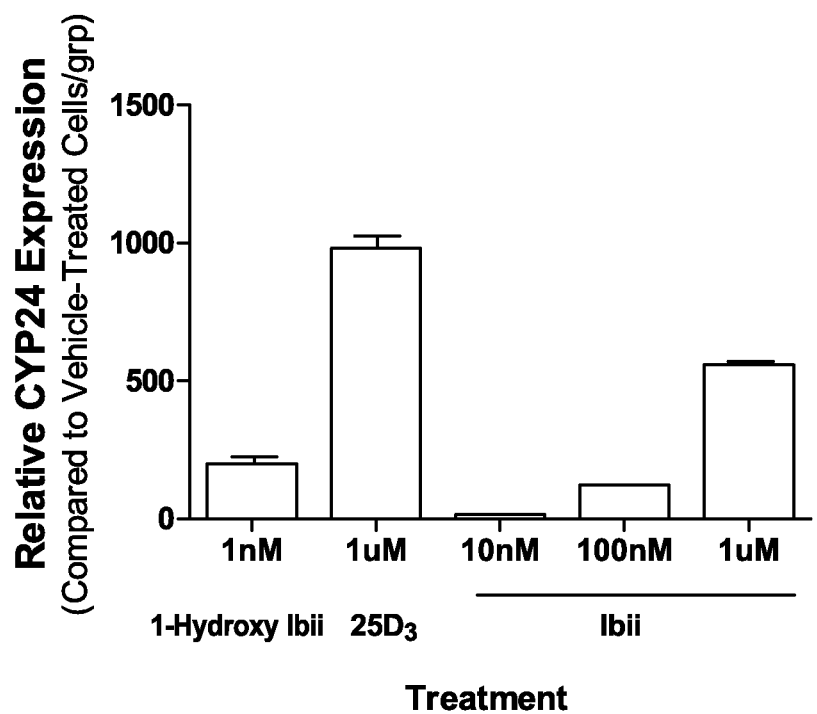

Although analogs of 1α,25-dihydroxyvitamin $D_3$, such as sulfoximine, oxime, and sulfone analogs of 1α,25-dihydroxyvitamin $D_3$, can have beneficial therapeutic effects, some can also cause an unphysiologically rapid increase in the blood level of both calcium and activated vitamin D hormone analog, followed by an almost as rapid decrease in the blood level of activated vitamin D hormone analog. Such rapid peaks and valleys of either the blood calcium or the activated vitamin D hormone analog are undesirable and can be harmful. Thus, it is desirable to provide prodrugs that would allow the slow or "on-demand" release analogs of 1α,25-dihydroxyvitamin $D_3$, for example low calcemic, anti-proliferative, selective CYP24 inhibitor analogs of 1α,25-dihydroxyvitamin $D_3$, to the body.

This present disclosure is directed to novel prodrugs of vitamin D-related compounds, and preferably those that show selective inhibition of the enzyme CYP24, and which are low calcemic and anti-proliferative. This disclosure is also directed to pharmaceutical and diagnostic compositions containing the prodrugs of the invention, and to their medical use, particularly as prodrugs in the treatment and/or prevention of diseases.

The compounds described herein can be described as synthetic prohormones, and can be activated by CYP27B1, for example by CYP27B1 expressed in the kidney, or by extrarenal CYP27B1.

The progressive decline in kidney function and concomitant loss of renal 1α-hydroxylase (CYP27B1) in chronic kidney disease (CKD) are associated with a gradual loss of circulating 25-hydroxyvitamin $D_3$ and 1α,25-dihydroxyvitamin $D_3$. However, only the decrease in 1α,25-dihydroxyvitamin $D_3$ can be explained by the decline of CYP27B1, suggesting that insufficiency of both metabolites may reflect their accelerated degradation by the key catabolic enzyme 24-hydroxylase (CYP24). To determine whether CYP24 is involved in causing vitamin D insufficiency and/or resistance to vitamin D therapy in CKD, the regulation of CYP24 and CYP27B1 was determined in normal rats and rats treated with adenine to induce CKD. Helvig et al. Kidney International 78, 463-472 (September 2010). As expected, CYP24 decreased whereas CYP27B1 increased when normal animals were rendered vitamin D deficient. Unexpectedly, renal CYP24 mRNA and protein expression were markedly elevated, irrespective of the vitamin D status of the rats. A significant decrease in serum 1α,25-dihydroxyvitamin $D_3$ levels was found in uremic rats; however, surprisingly there was not a coincident decline in CYP27B1 in uremic rats. Analysis in human kidney biopsies confirmed the association of elevated CYP24 with kidney disease.

Thus, because CYP27B1 is expressed in uremic kidneys, the use of compounds described herein can be used as prodrugs even in CKD patients. Furthermore, because some of the active 1α,25-dihydroxyvitamin $D_3$ analogs produced by the prodrugs described herein are more potent than 1α,25-dihydroxyvitamin $D_3$, the prodrugs can find utility in cases of End Stage Renal Disease where there is, in fact, very little renal CYP27B1 expression, but sufficient remaining renal CYP27B1 expression combined with extrarenal CYP27B1 expression to yield potent 1α,25-dihydroxyvitamin $D_3$ analogs.

As another example, in stage 5 renal disease, extrarenal CYP27B may be sufficient to activate a prodrug described herein in target tissues. For example, activation could occur in the parathyroid gland which contains CYP27B. This activation would present active hormone to the parathyroid VDR thereby reducing PTH gene transcription Furthermore, since active Vitamin D analogs downregulate CYP27B1 activity via a feedback mechanism, the production of active 1α,25-dihydroxyvitamin $D_3$ analogs via the prodrugs described herein is self-regulating, which leads to increased safety (e.g., avoiding oversuppression of PTH and hypercalcemia). Through a negative feedback loop, CYP27B in kidney is down-regulated as hormone levels rise. Therefore, any excess prodrug administered is not converted to active hormone—this provides a safe means to lower PTH without risk of PTH-oversuppression and hypercalcemia. Accordingly, compounds described herein, such as prodrug Iaii, can be administered at high doses without oversuppressing iPTH or causing hypercalcemia and its associated morbidities.

In the alternative, certain of the 1-deoxy compounds described herein will be 1-alpha hydroxylated by CYP27B1 to result in active compounds which are selective CYP24 inhibitors having little or no vitamin D agonist activity. Such compounds can have utility, for example, by selective suppression of CYP24 activity in cells in which they are activated. For example, in certain tumor cells (e.g., prostate cancer), CYP27B1 is overexpressed and CYP24 is overexpressed. Therefore, a CYP24 inhibitor prodrug as described herein would be more selectively activated in the tumor cell via overexpressed CYP27B1, and the activated form would selectively inhibit CYP24 activity in such cells.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "comprising" indicates the potential inclusion of other agents, elements, steps, or features, in addition to those specified.

As used herein, the term "Vitamin D toxicity" is meant to refer to the side effects suffered from excessively elevated Vitamin D blood levels, including one or more of nausea, vomiting, polyuria, hypercalciuria, hypercalcemia and hyperphosphatemia.

"Vitamin D insufficiency and deficiency" is generally defined as having serum 25-hydroxyvitamin D levels below 30 ng/mL (see National Kidney Foundation guidelines, NKF, Am. J. Kidney Dis. 42:S1-S202 (2003), incorporated herein by reference).

As used herein the term "hypercalcemia" refers to condition in a patient wherein the patient has corrected serum levels of calcium above 10.2 mg/dL. Normal corrected serum levels of calcium for a human are between about 8.6 to 10.2 mg/dL.

As used herein the term "hyperphosphatemia" refers to a condition in a patient having normal kidney function, or Stage 3-4 CKD, wherein the patient has serum phosphorous levels above 4.6 mg/dL. In a patient who has Stage 5 CKD, hyperphosphatemia occurs when the patient has serum levels above 5.5 mg/dL. Normal values for serum phosphorous in a human are 2.5-4.5 mg/dL.

As used herein the term "over suppression of plasma iPTH" refers to a condition in a patient having normal kidney function, or Stage 1-3 CKD, wherein the patient has levels of plasma iPTH below 15 pg/mL. In a patient having Stage 4 CKD, over suppression of plasma iPTH occurs when the patient has levels of plasma iPTH below 30 pg/mL. In a patient having Stage 5 CKD, over suppression of plasma iPTH occurs when the patient has levels of plasma iPTH below 100 pg/mL.

As used herein, the term "Vitamin D hormone replacement therapy" refers to the administration to a patient of an effective amount of an active vitamin D hormone such as 1,25-dihydroxyvitamin $D_3$ and/or 1,25-dihydroxyvitamin $D_2$, optionally together with or other metabolites and analogs of Vitamin D which can substantially occupy the intracellular VDR.

"Supraphysiologic" in reference to intraluminal, intracellular and blood levels of Vitamin D refers to a total concentration of the vitamin D compound markedly greater than the generally stable levels observed in a Vitamin D-replete subject, animal or human patient over the course of any 24-hour period by laboratory measurement when Vitamin D supplementation has been withheld for at least 30 days. "Adverse supraphysiologic surge" refers to a local or serum concentration of a vitamin D compound that elicits an adverse effect, such as excessive extrarenal hormone production, leading to a local adverse effect, for example on calcium or phosphorus metabolism, inhibition of hepatic 25-hydroxylation of vitamin D, increased catabolism of both Vitamin D and 25-hydroxyvitamin D, hypercalciuria, hypercalcemia and/or hyperphosphatemia, with possible cardiovascular sequelae.

The term "therapeutically effective amount" depends on the patient's condition and is an amount effective to achieve a desired clinical effect, e.g. to maintain a laboratory test value within the normal range or the recommended range for that patient's condition, or an amount effective to reduce the occurrence or severity of a clinical sign or symptom of disease. In preferred embodiments, a therapeutically effective amount is an amount effective on average to achieve at least a 15%, 20%, 25% or 30% reduction in serum parathyroid hormone levels (iPTH) from baseline levels without treatment. In yet other embodiments, a therapeutically effective amount is an amount effective on average to reach CKD Stage-specific iPTH target ranges, which for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1).

As used herein, the term "hyperparathyroidism" refers to primary hyperparathyroidism, secondary hyperparathyroidism and hyperparathyroidism secondary to chronic kidney disease (Stage 3, 4 or 5).

The term "subject" as used herein generally includes humans, mammals (e.g., dogs, cats, rodents, sheep, horses, cows, goats), veterinary animals and zoo animals.

As used herein, the term "pharmaceutically acceptable salt" refers to an acid addition salt or a basic addition salt which is suitable for or compatible with the treatment of patients.

As used herein, the term "hydrate" refers to a salt of a compound of the invention, wherein molecules of water are incorporated in the crystal lattice.

As used herein, the term "solvate" refers to a compound of the invention wherein molecules of a suitable solvent are incorporated in the crystal lattice. A suitable solvent is physiologically tolerable at the dosage administered. An example of a suitable solvent is ethanol.

As used herein, the term "ester derivatives of the prodrug compounds" refers to esters that are formed with one or more available hydroxyl groups of the prodrug compounds described herein. Contemplated esters include phenyl esters, aliphatic (C8-C24) esters, acyloxymethyl esters, carbamates, and amino acid esters. For example, when $R^1$ is OH in a prodrug compound described herein, it may be acylated using a carboxylic acid or an activated form of a carboxylic acid in the presence of a base, and optionally, in an inert solvent (e.g. an acid chloride in pyridine).

As used herein, the term "alkyl" refers to straight chained and branched saturated hydrocarbon groups, nonlimiting examples of which include methyl, ethyl, and straight chain and branched propyl and butyl groups. $C_{1-6}$alkyl refers to alkyl groups that can have, for example, from 1 to 6 carbon atoms encompassing the entire range (i.e., 1 to 6 carbon atoms), as well as all subgroups (e.g., 1-5, 2-6, 1-4, 3-6, 1, 2, 3, 4, 5, and 6 carbon atoms). $C_{1-4}$alkyl refers to alky groups that can have, for example, from 1 to 4 carbon atoms encompassing the entire range (i.e., 1 to 4 carbon atoms), as well as all subgroups (e.g., 1-3, 2-4, 2-3, 3-4, 1, 2, 3, and 4 carbon atoms). $C_{1-2}$alkyl refers to alky groups that can have 1 or 2 carbon atoms). Unless otherwise indicated, $C_{1-6}$alkyl and $C_{1-4}$alkyl can be unsubstituted or substituted with 1 to 5 substituents independently selected from the group consisting of $C_{1-4}$alkyl, $C_{2-4}$alkenyl, $OC_{1-4}$alkyl, $OC_{2-4}$alkenyl, $CF_3$, $NO_2$, halo, OH, $OCF_3$, SH, $SC_{1-4}$alkyl, $NH_2$, $NHC_{1-4}$alkyl, $NHC_{2-4}$alkenyl, $N(C_{1-4}$alkyl)($C_{1-4}$alkyl), $N(C_{2-4}$alkenyl)($C_{1-4}$alkyl) and CN.

As used herein, the term "alkenyl" refers to straight and/or branched chain unsaturated alkenyl radicals. $C_{2-6}$alkenyl refers to alkenyl groups that can have, for example, from 2 to 6 carbon atoms encompassing the entire range (i.e., 2 to 6 carbon atoms), as well as all subgroups (e.g., 2-5, 3-6, 2-4, 4-6, 2, 3, 4, 5, and 6 carbon atoms). $C_{2-4}$alkenyl refers to alkeny groups that can have, for example, from 2 to 4 carbon atoms encompassing the entire range (i.e., 2 to 4 carbon atoms), as well as all subgroups (e.g., 2-3, 3-4, 2, 3, and 4 carbon atoms). Unless otherwise indicated, $C_{2-6}$alkenyl and $C_{2-4}$alkenyl can be unsubstituted or substituted with 1 to 5 substituents independently selected from the group consisting of $C_{1-4}$alkyl, $C_{2-4}$alkenyl, $OC_{1-4}$alkyl, $OC_{2-4}$alkenyl, $CF_3$, $NO_2$, halo, OH, $OCF_3$, SH, $SC_{1-4}$alkyl, $NH_2$, $NHC_{1-4}$alkyl, $NHC_{2-4}$alkenyl, $N(C_{1-4}$alkyl$)(C_{1-4}$alkyl$)$, $N(C_{2-4}$alkenyl$)(C_{1-4}$alkyl$)$ and CN.

As used herein the term "cycloalkyl" refers to saturated, non-aromatic cyclic alkyl radicals. For example, $C_{3-6}$cycloalkyl refers to cycloalkyl groups containing from three to six carbon atoms and includes cyclopropyl, cyclobutyl, cyclopentyl, and cyclohexyl. "Heterocycloalkyl" is defined similarly as cycloalkyl, except the ring contains one or more heteroatoms, for example, one to three heteroatoms, independently selected from the group consisting of oxygen, nitrogen, and sulfur. Nonlimiting examples of heterocycloalkyl groups include piperidinyl, tetrahydrofuranyl, tetrahydropyranyl, dihydrofuranyl, and the like. Cycloalkyl and heterocycloalkyl groups can optionally substituted with 1 to 5 substituents independently selected from the group consisting of $C_{1-4}$alkyl, $C_{2-4}$alkenyl, $OC_{1-4}$alkyl, $OC_{2-4}$alkenyl, $CF_3$, $NO_2$, halo, OH, $OCF_3$, SH, $SC_{1-4}$alkyl, $NH_2$, $NHC_{1-4}$alkyl, $NHC_{2-4}$alkenyl, $N(C_{1-4}$alkyl$)(C_{1-4}$alkyl$)$, $N(C_{2-4}$alkenyl$)(C_{1-4}$alkyl$)$ and CN.

As used herein, the term "cycloalkenyl" refers to unsaturated, non-aromatic cyclic alkenyl radicals. For example, cyclo($C_3$-$C_6$)alkenyl refers to cyclic alkenyl radicals containing from three to six carbon atoms and includes cyclopropenyl, cylobutenyl, cyclopentenyl and cyclohexenyl.

As used herein, the term "halo" refers to the halogens of Group VIIA of the periodic table, such as F, Cl, Br, and I.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with 1 to 5 groups independently selected from $C_{1-4}$alkyl, $C_{2-4}$alkenyl, $OC_{1-4}$alkyl, $OC_{2-4}$alkenyl, OH, $CF_3$, $OCF_3$, halo, SH, $SC_{1-4}$alkyl, $SC_{2-4}$alkenyl $NH_2$, $NHC_{1-4}$alkyl, $NHC_{2-4}$alkenyl, $N(C_{1-4}$alkyl$)(C_{1-4}$alkyl$)$, $N(C_{2-4}$alkenyl$)(C_{1-4}$alkyl$)$CN, C(O)OH, C(O)O$C_{1-4}$alkyl, C(O)O$C_{2-4}$alkenyl, C(O)NH$C_{1-4}$alkyl, C(O)NH$C_{2-4}$alkenyl, NHC(O)$C_{1-4}$alkyl, NHC(O)$C_{2-4}$alkenyl, OC(O)$C_{1-4}$alkyl, OC(O)$C_{2-4}$alkenyl, SO$C_{1-4}$alkyl, SO$C_{2-4}$alkenyl, $SO_2$ $C_{1-4}$alkyl, $SO_2C_{2-4}$alkenyl, $SO_2$NH$C_{1-4}$alkyl, $SO_2$NH$C_{2-4}$alkenyl and $SO_2NH_2$. Exemplary aryl groups include, but are not limited to, phenyl, naphthyl, tetrahydronaphthyl, chlorophenyl, methylphenyl, methoxyphenyl, trifluoromethylphenyl, nitrophenyl, and 2,4-methoxychlorophenyl.

As used herein, the term "heteroaryl" refers to a monocyclic or polycyclic aromatic group, preferably a monocyclic or bicyclic aromatic group, containing at least one nitrogen, oxygen, or sulfur atom in an aromatic ring. Unless otherwise indicated, a heteroaryl group can be unsubstituted or substituted with 1 to 5 groups independently selected from $C_{1-4}$alkyl, $C_{2-4}$alkenyl, $OC_{1-4}$alkyl, $OC_{2-4}$alkenyl, OH, $CF_3$, $OCF_3$, halo, SH, $SC_{1-4}$alkyl, $SC_{2-4}$alkenyl $NH_2$, $NHC_{1-4}$alkyl, $NHC_{2-4}$alkenyl, $N(C_{1-4}$alkyl$)(C_{1-4}$alkyl$)$, $N(C_{2-4}$alkenyl$)(C_{1-4}$alkyl$)$CN, C(O)OH, C(O)O$C_{1-4}$alkyl, C(O)O$C_{2-4}$alkenyl, C(O)NH$C_{1-4}$alkyl, C(O)NH$C_{2-4}$alkenyl, NHC(O)$C_{1-4}$alkyl, NHC(O)$C_{2-4}$alkenyl, OC(O)$C_{1-4}$alkyl, OC(O)$C_{2-4}$alkenyl, SO$C_{1-4}$alkyl, SO$C_{2-4}$alkenyl, $SO_2$ $C_{1-4}$alkyl, $SO_2C_{2-4}$alkenyl, $SO_2$NH$C_{1-4}$alkyl, $SO_2$NH $C_{2-4}$alkenyl and $SO_2NH_2$. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

As used herein, the term "modulate" includes the inhibition or suppression of a function or activity (such as CYP24 activity) as well as the enhancement of a function or activity.

As used herein, to "inhibit" or "suppress" or "reduce" a function or activity, such as CYP24 activity, is to reduce the function of activity when compared to otherwise same conditions except for a condition or parameter of interest, or alternatively, as compared to another condition.

As used therein, the term "animal" includes all members of the animal kingdom including human. The animal is preferably a human.

As used herein, the term "cell" includes a plurality of cells. Administering a compound to a cell includes in vivo, ex vivo, and in vitro treatment.

As used herein, the term "cancer cells" includes all forms of cancer or neoplastic disease.

As used herein, the term "catabolism" refers to the metabolic process by which organisms convert substances into compounds for excretion.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that intermediate values and ranges, such as 2% to 40%, 10% to 30%, or 1% to 3%, etc., are expressly enumerated in this specification. These are only examples of what is specifically intended.

The compounds, compositions, methods and uses of the invention described herein are contemplated to include embodiments including any combination of one or more of the additional optional or preferred elements, features, and steps further described below (including those shown in the figures), unless stated otherwise.

In one aspect, the invention provides compounds of Formula I, or a pharmaceutically acceptable salt, solvate, or hydrate thereof:

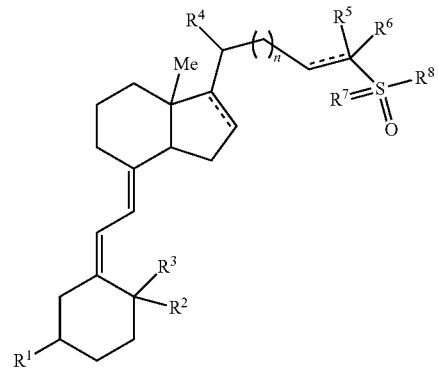

Formula I wherein each --- independently is a single bond or a double bond;

n is 0, 1 or 2;

$R^1$ is selected from the group consisting of OH, $OC_{1-6}$alkyl, and halo;

$R^2$ and $R^3$ are each independently H or halo, or together form $=CH_2$;

$R^4$ is $C_{1-6}$alkyl;

$R^5$ and $R^6$ are each independently H, halo, $C_{1-4}$alkyl, or can be taken, together with the carbon atom to which they are bound, to form a $C_{3-6}$cycloalkyl ring, with the proviso that when --- between carbon-23 and carbon-24 is a double bond, then $R^5$ is absent;
$R^7$ is selected from the group consisting of O, NH, $N(C_{1-6}$alkyl), and $NC(O)R^9$;
$R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo, OH, $OCF_3$, SH, $SC_{1-4}$alkyl, $NH_2$, $NHC_{1-4}$alkyl, $N(C_{1-4}$alkyl$)(C_{1-4}$alkyl), and CN; and
$R^9$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo.

One contemplated class of embodiments of this aspect of the invention is characterized by n being 0 or 1.

Another class of embodiments of this aspect of the invention is characterized by $R^1$ being OH or halo, more preferably OH or F, and further preferably OH.

Another class of embodiments of this aspect of the invention is characterized by $R^2$ and $R^3$ each being both H or together forming =$CH_2$; more preferably $R^2$ and $R^3$ together form =$CH_2$.

Another class of embodiments of this aspect of the invention is characterized by $R^4$ being $C_{1-4}$alkyl, and more preferably $CH_3$.

Another class of embodiments of this aspect of the invention is characterized by $R^5$ and $R^6$ each independently being H, $C_{1-2}$alkyl, or halo, and more preferably H, $CH_3$, or halo, with the proviso that when --- between carbon-23 and carbon-24 is a double bond, then $R^5$ is absent.

Another class of embodiments of this aspect of the invention is characterized by $R^7$ being selected from the group consisting of O, NH, and $N(C_{1-6}$alkyl), and more preferably O or NH.

Another class of embodiments of this aspect of the invention is characterized by $R^8$ being selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo; more preferably $R^8$ is selected from the group consisting of $C_{1-4}$alkyl, aryl and heteroaryl, wherein each of aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo; further preferably $R^8$ is selected from the group consisting of $C_{1-4}$alkyl and aryl, wherein aryl is either unsubstituted or substituted with 1 to 5 substituents independently selected from the group consisting of $C_{1-4}$alkyl, $OC_{1-4}$alkyl, $CF_3$, $NO_2$, and halo.

Another class of embodiments of this aspect of the invention is characterized by the compounds of Formula I including those in which each --- independently is a single bond or a double bond; n is 0 or 1; $R^1$ is OH or halo; $R^2$ and $R^3$ are either both H or together form =$CH_2$; $R^4$ is $C_{1-4}$alkyl; $R^5$ and $R^6$ are each independently H, $C_{1-2}$alkyl, or halo, with the proviso that when --- between carbon-23 and carbon-24 is a double bond, then $R^5$ is absent; $R^7$ is selected from the group consisting of O, NH, and $N(C_{1-6}$alkyl); and $R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo.

Another class of embodiments of this aspect of the invention is characterized by the compounds of Formula I including those in which each --- independently is a single bond or a double bond; n is 0 or 1; $R^1$ is OH or F; $R^2$ and $R^3$ together form =$CH_2$; $R^4$ is $CH_3$; $R^5$ and $R^6$ are each independently H, $CH_3$, or halo, with the proviso that when --- between carbon-23 and carbon-24 is a double bond, then $R^5$ is absent; $R^7$ is O or NH; and $R^8$ is selected from the group consisting of $C_{1-4}$alkyl, aryl and heteroaryl, wherein each of aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo.

Another class of embodiments of this aspect of the invention is characterized by the compounds of Formula I including those in which each --- independently is a single bond or a double bond; n is 0 or 1; $R^1$ is OH; $R^2$ and $R^3$ together form =$CH_2$; $R^4$ is $CH_3$; $R^5$ and $R^6$ are each independently H, $CH_3$, Cl, or F, with the proviso that when --- between carbon-23 and carbon-24 is a double bond, then $R^5$ is absent; $R^7$ is O or NH; and $R^8$ is selected from the group consisting of $C_{1-4}$alkyl and aryl, wherein aryl is either unsubstituted or substituted with 1 to 5 substituents independently selected from the group consisting of $C_{1-4}$alkyl, $OC_{1-4}$alkyl, $CF_3$, $NO_2$, and halo.

In specific embodiments of the present invention, the compounds of Formula I include:

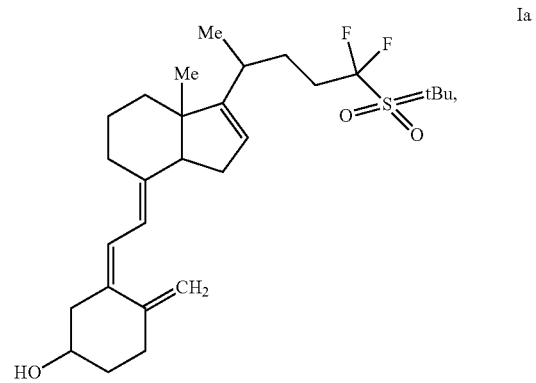

Ia

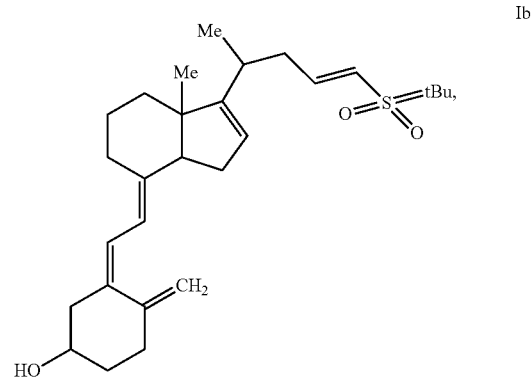

Ib

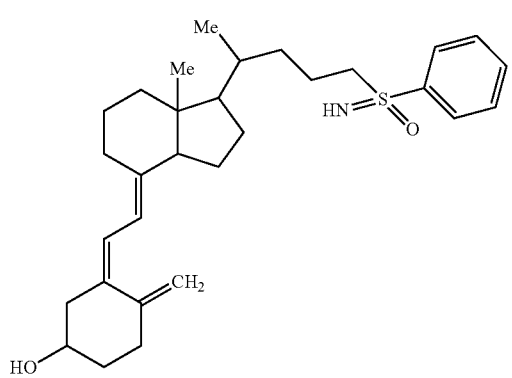
Ic
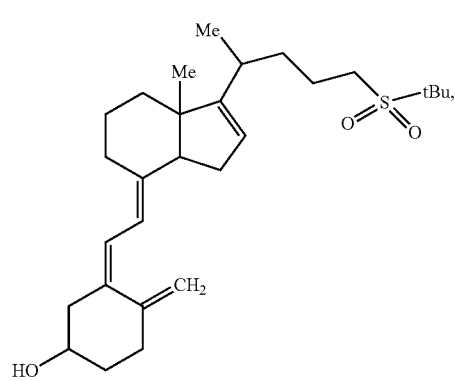
Ig
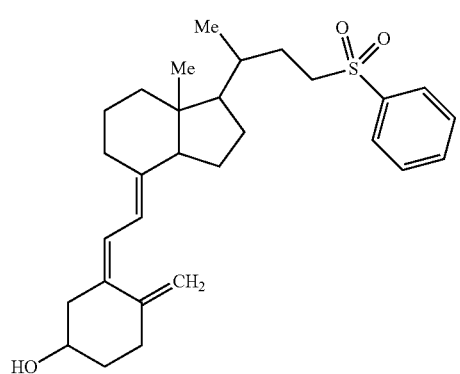
Id
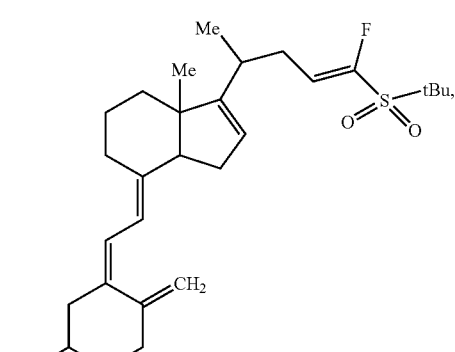
Ih
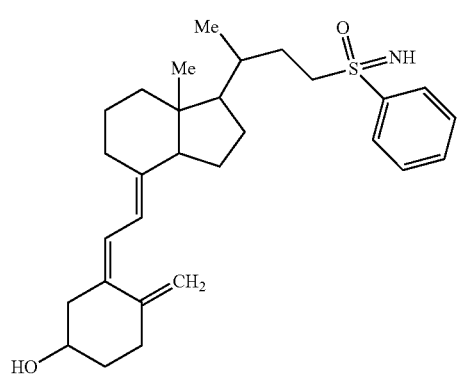
Ie
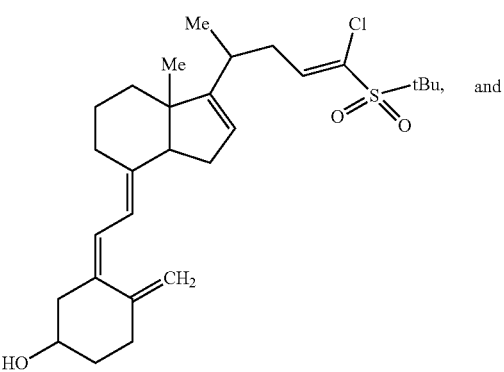
Ij
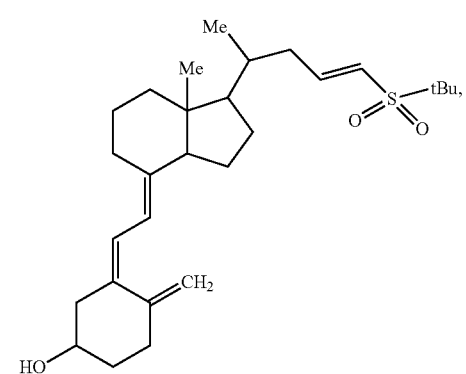
If
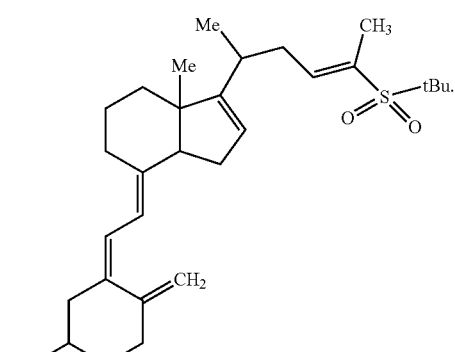
Ik
All of the compounds of Formula I have more than one chiral center. Where the compounds according to the invention possess more than one chiral center, they may exist as stereoisomers. It is to be understood that all such isomers and mixtures thereof in any proportion are encompassed within the scope of the present invention. The stereochemistry of the A, C and D rings and at the C20 position of the compounds of the invention is preferably that of natural 25-dihydroxyvitamin $D_3$. When $R^7$ is not O, the stereochemistry at the sulfur atom may be either R or S. Therefore the present invention preferably provides compounds of Formula I, and pharmaceutically acceptable acid addition salts and hydrates thereof, having the following relative stereochemistry:

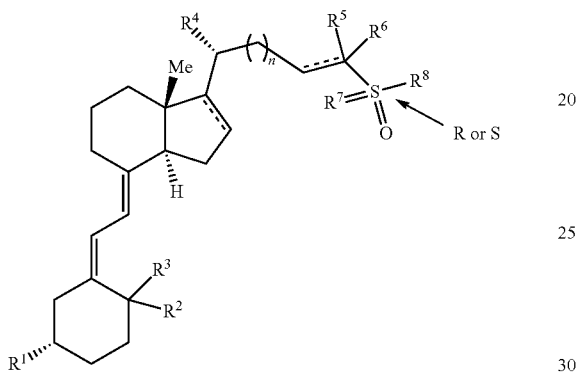

wherein ---, n, and $R^1$-$R^8$ are as defined above. One class of embodiments is characterized by --- being a double bond between carbon-23 and carbon-24 with 'E' stereochemistry.

It is to be understood that, while the relative stereochemistry of the compounds of Formula I is preferably as shown above, such compounds of Formula I may also contain certain amounts (e.g. less than 20%, preferably less than 10%, more preferably less than 5%) of compounds of Formula I having alternate stereochemistry. For example, a compound of Formula I having the 3β-stereochemistry of natural 25-dihydroxyvitamin $D_3$, shown above, may contain less then 20%, preferably less then 10%, more preferably less then 5%, of a compound of Formula I having the unnatural 3α-stereochemistry.

In embodiments of the present invention, the compounds of Formula I include:

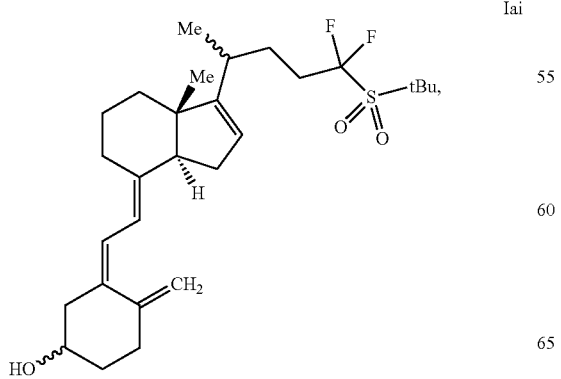

Iai

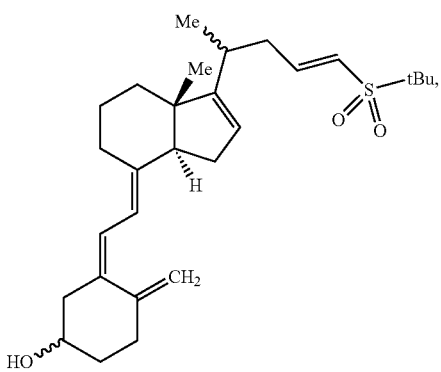

Ibi

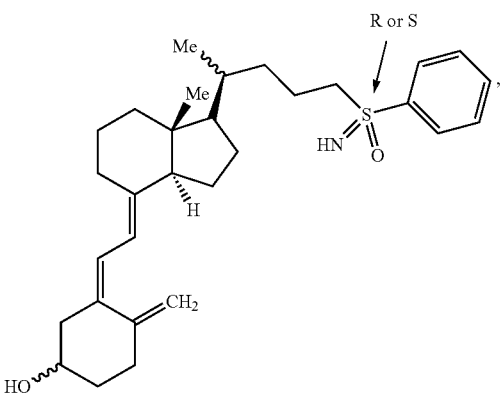

Ici

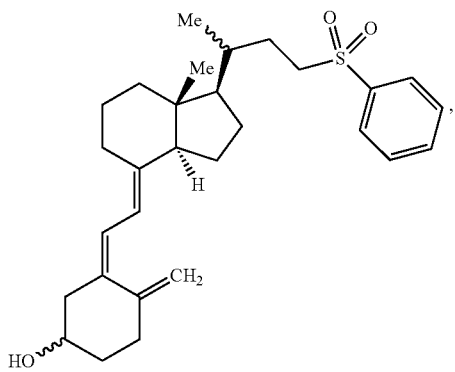

Idi

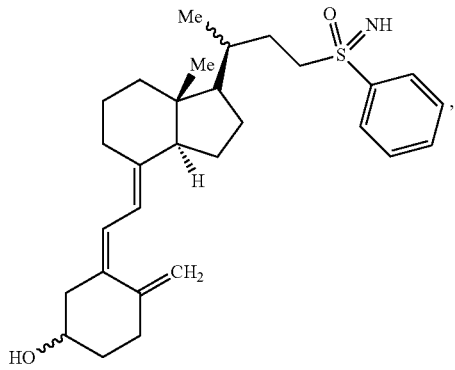

Iei

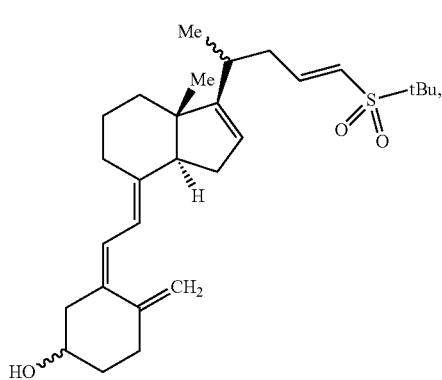
Ifi
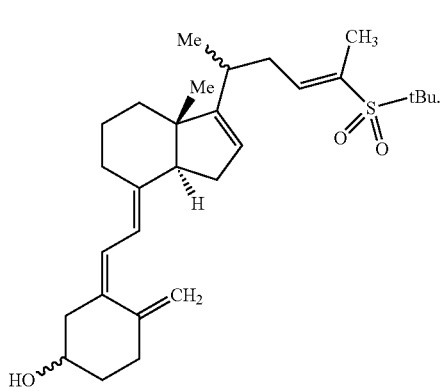
Iki
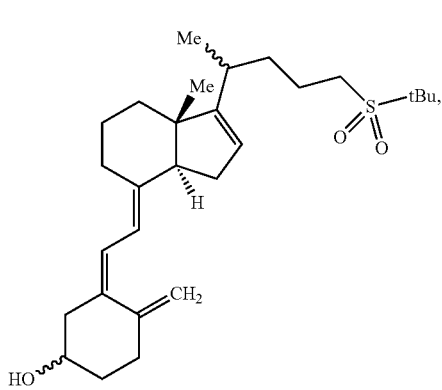
Igi
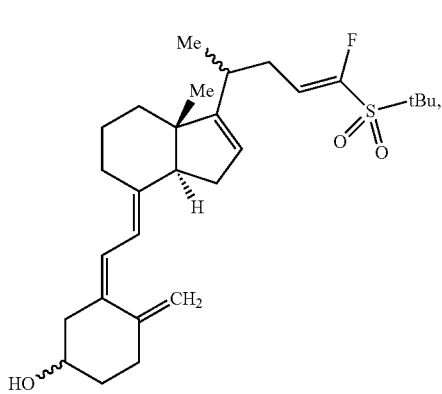
Ihi
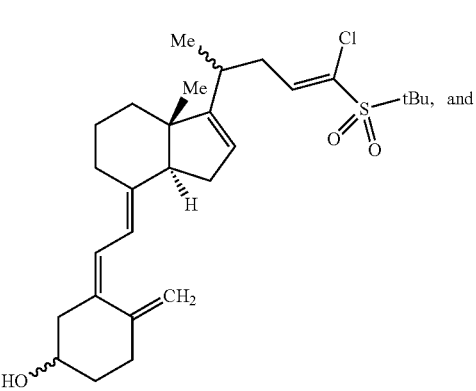
Iji
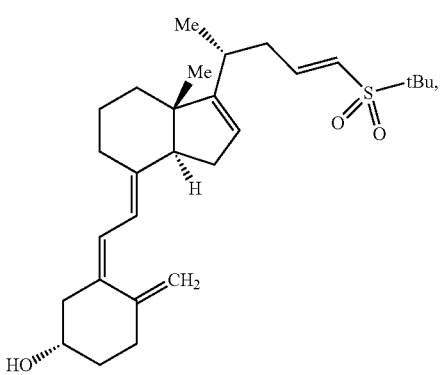
Ibii
wherein the symbol, ⁓, represents that the carbon atom to which it is bound can have either R or S stereochemistry.
In specific embodiments of the present invention, the compounds of Formula I include:
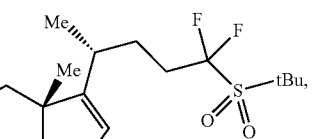
Iaii
and -continued
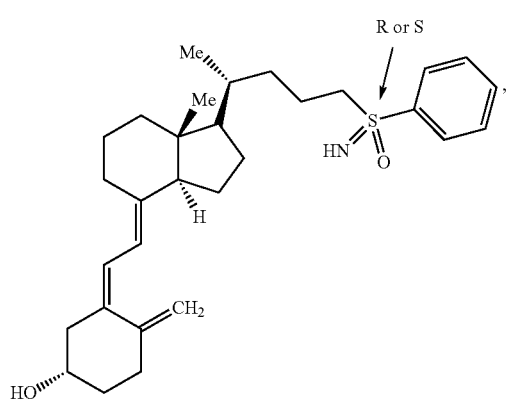
Icii
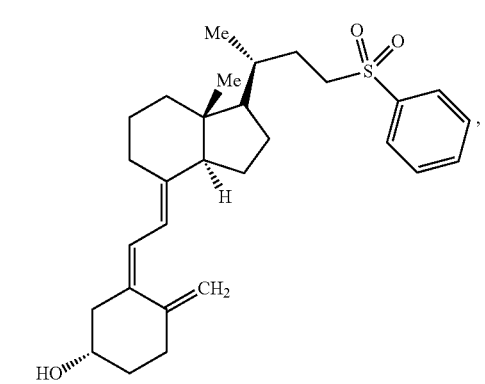
Idii
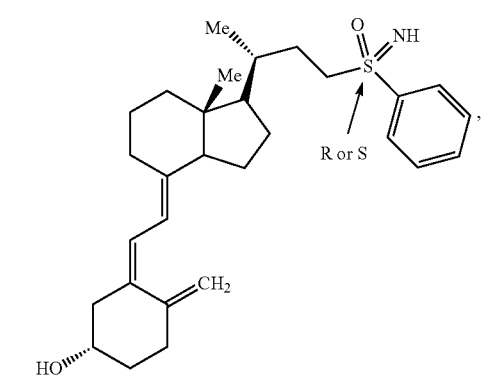
Ieii
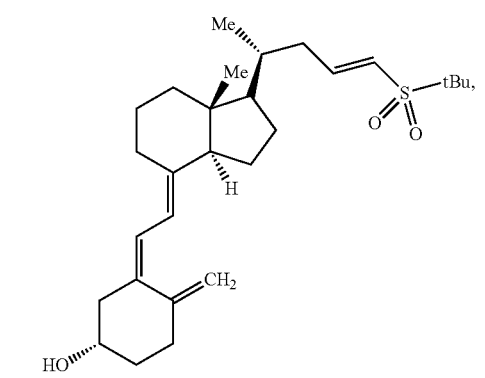
Ifii
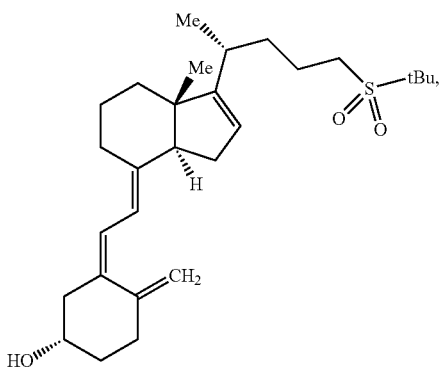
Igii
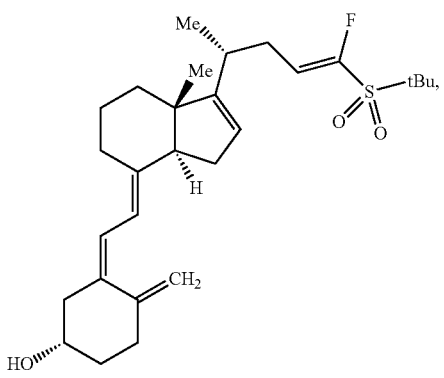
Ihii
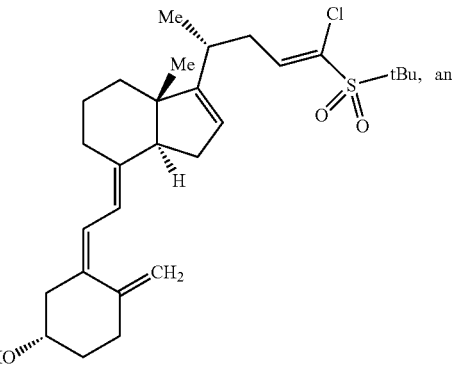
Ijii, and
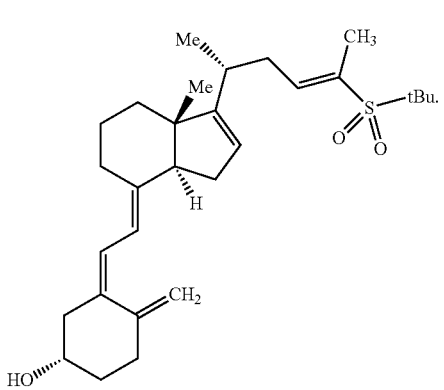
Ikii
In another aspect, the invention provides a compound of Formula II, or a pharmaceutically acceptable salt, solvate or hydrate thereof:

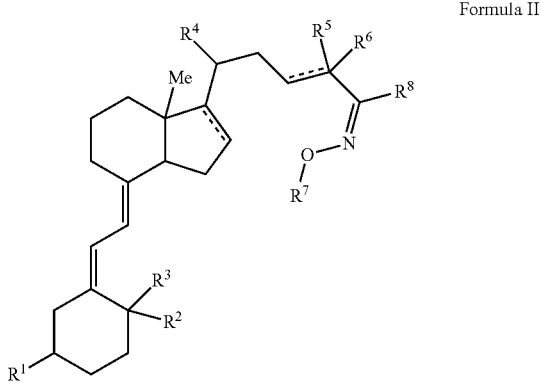

Formula II wherein each --- independently is a single bond or a double bond;
$R^1$ is selected from the group consisting of OH, $OC_{1-6}$alkyl, and halo;
$R^2$ and $R^3$ are each independently H or halo, or together form $=CH_2$;
$R^4$ is $C_{1-6}$alkyl;
$R^5$ and $R^6$ are each independently H, halo, $C_{1-4}$alkyl, or can be taken, together with the carbon atom to which they are bound, to form a $C_{3-6}$cycloalkyl ring, with the proviso that when --- between carbon-23 and carbon-24 is a double bond, then $R^5$ is absent;
$R^7$ is selected from the group consisting of H, $C_{1-6}$alkyl, $C_{2-6}$alkenyl, aryl and heteroaryl, with $C_{1-6}$alkyl and $C_{2-6}$alkenyl being unsubstituted or substituted with 1 to 4 groups independently selected from $C_{1-4}$alkyl, $C_{2-4}$alkenyl, $OC_{1-4}$alkyl, $OC_{2-4}$alkenyl, OH, halo, $NH_2$, $NHC_{1-4}$alkyl, $NHC_{2-4}$alkenyl, $N(C_{1-4}$alkyl$)(C_{1-4}$alkyl$)$, $N(C_{2-4}$alkenyl$)(C_{1-4}$alkyl$)$, and with aryl and heteroaryl being unsubstituted or substituted with 1 to 5 groups independently selected from $C_{1-4}$alkyl, $C_{2-4}$alkenyl, $OC_{1-4}$alkyl, $OC_{2-4}$alkenyl, OH, $CF_3$, $OCF_3$, halo, SH, $SC_{1-4}$alkyl, $SC_{2-4}$alkenyl $NH_2$, $NHC_{1-4}$alkyl, $NHC_{2-4}$alkenyl, $N(C_{1-4}$alkyl$)(C_{1-4}$alkyl$)$, $N(C_{2-4}$alkenyl$)(C_{1-4}$alkyl$)$CN, C(O)OH, $C(O)OC_{1-4}$alkyl, $C(O)OC_{2-4}$alkenyl, $C(O)NHC_{1-4}$alkyl, $C(O)NHC_{2-4}$alkenyl, $NHC(O)C_{1-4}$alkyl, $NHC(O)C_{2-4}$alkenyl, $OC(O)C_{1-4}$alkyl, $OC(O)C_{2-4}$alkenyl, $SOC_{1-4}$alkyl, $SOC_{2-4}$alkenyl, $SO_2C_{1-4}$alkyl, $SO_2C_{2-4}$alkenyl, $SO_2NHC_{1-4}$alkyl, $SO_2NHC_{2-4}$alkenyl and $SO_2NH_2$; and
$R^8$ is selected from the group consisting of $C_{1-6}$alkyl, $C_{2-6}$alkenyl, cyclo($C_3$-$C_6$)alkyl, cyclo($C_5$-$C_6$)alkenyl, aryl, heteroaryl, aryl-$C_{1-6}$alkyl, aryl-$C_{2-6}$alkenyl, heteroaryl-$C_{1-6}$alkyl, and heteroaryl-$C_{2-6}$alkenyl with $C_{1-6}$alkyl and $C_{2-6}$alkenyl being unsubstituted or substituted with 1-4 groups independently selected from $C_{1-4}$alkyl, $C_{2-4}$alkenyl, $OC_{1-4}$alkyl, $OC_{2-4}$alkenyl, OH, halo, $NH_2$, $NHC_{1-4}$alkyl, $NHC_{2-4}$alkenyl, $N(C_{1-4}$alkyl$)(C_{1-4}$alkyl$)$, and $N(C_{2-4}$alkenyl$)(C_{1-4}$alkyl$)$, and with cyclo($C_3$-$C_6$)alkyl, cyclo($C_5$-$C_6$) alkenyl aryl, heteroaryl, aryl-$C_{1-6}$alkyl, aryl-$C_{2-6}$alkenyl, heteroaryl-$C_{1-6}$alkyl, heteroaryl-$C_{2-6}$alkenyl being unsubstituted or substituted with 1-5 groups independently selected from $C_{1-4}$alkyl, $C_{2-4}$alkenyl, $OC_{1-4}$alkyl, $OC_{2-4}$alkenyl, OH, $CF_3$, $OCF_3$, halo, SH, $SC_{1-4}$alkyl, $SC_{2-4}$alkenyl, $NH_2$, $NHC_{1-4}$alkyl, $NHC_{2-4}$alkenyl, $N(C_{1-4}$alkyl$)(C_{1-4}$alkyl$)$, $N(C_{2-4}$alkenyl$)(C_{1-4}$alkyl$)$, CN, C(O)OH, $C(O)OC_{1-4}$alkyl, $C(O)OC_{2-4}$alkenyl, $C(O)NHC_{1-4}$alkyl, $C(O)NHC_{2-4}$alkenyl, $NHC(O)C_{1-4}$alkyl, $NHC(O)C_{2-4}$alkenyl, $OC(O)C_{1-4}$alkyl, $OC(O)C_{2-4}$alkenyl, $SOC_{1-4}$alkyl, $SOC_{2-4}$alkenyl $SO_2C_{1-4}$alkyl, $SO_2C_{2-4}$alkenyl, $SO_2NHC_{1-4}$alkyl, $SO_2NHC_{2-4}$alkenyl and $SO_2NH_2$.

One contemplated class of embodiments of this aspect of the invention is characterized by $R^1$ being OH or F, and more preferably OH.

Another class of embodiments of this aspect of the invention is characterized by $R^2$ and $R^3$ being are either both H or together form $=CH_2$, and more preferably $R^2$ and $R^3$ together form $=CH_2$.

Another class of embodiments of this aspect of the invention is characterized by $R^4$ being $C_{1-4}$alkyl, and more preferably $CH_3$.

Another class of embodiments of this aspect of the invention is characterized by each $R^5$ and $R^6$ independently being H, $C_{1-2}$alkyl, or halo, more preferably H, $CH_3$, Cl, or F, and further preferably both H, with the proviso that when --- between carbon-23 and carbon-24 is a double bond, then $R^5$ is absent.

Another class of embodiments of this aspect of the invention is characterized by $R^7$ being selected from the group consisting of H, $C_{1-4}$alkyl, $C_{2-5}$alkenyl, aryl and heteroaryl, with $C_{1-4}$alkyl and $C_{2-4}$alkenyl being unsubstituted or substituted with 1 to 4 groups independently selected from $C_{1-4}$alkyl, $C_{2-4}$alkenyl, $OC_{1-4}$alkyl, $OC_{2-4}$alkenyl, OH, and halo, and with aryl and heteroaryl being unsubstituted or substituted with 1 to 5 groups independently selected from $C_{1-4}$alkyl, $C_{2-4}$alkenyl, $OC_{1-4}$alkyl, $OC_{2-4}$alkenyl, OH, $CF_3$, $OCF_3$, and halo. More preferably, $R^7$ is selected from the group consisting of H, $C_{1-4}$alkyl, $C_{2-5}$alkenyl, aryl and heteroaryl, with aryl and heteroaryl being unsubstituted or substituted with 1 to 5 groups independently selected from $C_{1-4}$alkyl, $OC_{1-4}$alkyl, OH, $CF_3$, $OCF_3$, and halo.

Another class of embodiments of this aspect of the invention is characterized by $R^8$ being selected from the group consisting of $C_{1-4}$alkyl, $C_{2-4}$alkenyl, cyclo($C_3$-$C_6$) alkyl, cyclo($C_5$-$C_6$)alkenyl, aryl, heteroaryl, with $C_{1-4}$alkyl and $C_{2-4}$alkenyl being unsubstituted or substituted with 1-4 groups independently selected from $C_{1-4}$alkyl, $C_{2-4}$alkenyl, $OC_{1-4}$alkyl, $OC_{2-4}$alkenyl, OH, and halo, and with cyclo($C_3$-$C_6$)alkyl, cyclo($C_5$-$C_6$)alkenyl aryl, and heteroaryl, being unsubstituted or substituted with 1-5 groups independently selected from $C_{1-4}$alkyl, $C_{2-4}$alkenyl, $OC_{1-4}$alkyl, $OC_{2-4}$alkenyl, OH, $CF_3$, $OCF_3$, and halo. More preferably, $R^8$ is selected from the group consisting of $C_{1-4}$alkyl, aryl, and heteroaryl, with aryl, and heteroaryl, being unsubstituted or substituted with 1-5 groups independently selected from $C_{1-4}$alkyl, $OC_{1-4}$alkyl, OH, $CF_3$, $OCF_3$, and halo. Further preferably, $R^8$ is selected from the group consisting of $C_{1-4}$alkyl, aryl, and heteroaryl, with aryl, and heteroaryl, being unsubstituted or substituted with 1-5 groups independently selected from $C_{1-4}$alkyl, $OC_{1-4}$alkyl, OH, $CF_3$, $OCF_3$, and halo.

Another class of embodiments of this aspect of the invention is characterized by the compounds of Formula I including those in which each --- independently is a single bond or a double bond; $R^1$ is OH or halo; $R^2$ and $R^3$ are either both H or together form $=CH_2$; $R^4$ is $C_{1-4}$alkyl; $R^5$ and $R^6$ are each independently H, $C_{1-2}$alkyl, or halo, with the proviso that when --- between carbon-23 and carbon-24 is a double bond, then $R^5$ is absent; $R^7$ is selected from the group consisting of H, $C_{1-4}$alkyl, $C_{2-5}$alkenyl, aryl and heteroaryl, with $C_{1-4}$alkyl and $C_{2-4}$alkenyl being unsubstituted or substituted with 1 to 4 groups independently selected from $C_{1-4}$alkyl, $C_{2-4}$alkenyl, $OC_{1-4}$alkyl, $OC_{2-4}$alkenyl, OH, and halo, and with aryl and heteroaryl being unsubstituted or substituted with 1 to 5 groups independently selected from $C_{1-4}$alkyl, $C_{2-4}$alkenyl, $OC_{1-4}$alkyl, $OC_{2-4}$alkenyl, OH, $CF_3$, $OCF_3$, and halo; and $R^8$ is selected from the group consisting of $C_{1-4}$alkyl, $C_{2-4}$alkenyl, cyclo($C_3$-$C_6$)alkyl, cyclo($C_5$-$C_6$)alkenyl, aryl, heteroaryl, with $C_{1-4}$alkyl and $C_{2-4}$alkenyl being unsubstituted or substituted with 1-4 groups independently selected from $C_{1-4}$alkyl, $C_{2-4}$alkenyl, $OC_{1-4}$alkyl, $OC_{2-4}$alkenyl, OH, and halo, and with cyclo($C_3$-$C_6$)alkyl, cyclo($C_5$-$C_6$)alkenyl aryl, and heteroaryl, being unsubstituted or substituted with 1-5 groups independently selected from $C_{1-4}$alkyl, $C_{2-4}$alkenyl, $OC_{1-4}$alkyl, $OC_{2-4}$alkenyl, OH, $CF_3$, $OCF_3$, and halo.

Another class of embodiments of this aspect of the invention is characterized by the compounds of Formula I including those in which each --- independently is a single bond or a double bond; $R^1$ is OH or F; $R^2$ and $R^3$ together form =$CH_2$; $R^4$ is $CH_3$; $R^5$ and $R^6$ are each independently H, $CH_3$, Cl, or F, with the proviso that when --- between carbon-23 and carbon-24 is a double bond, then $R^5$ is absent; $R^7$ is selected from the group consisting of H, $C_{1-4}$alkyl, $C_{2-5}$alkenyl, aryl and heteroaryl, with aryl and heteroaryl being unsubstituted or substituted with 1 to 5 groups independently selected from $C_{1-4}$alkyl, $OC_{1-4}$alkyl, OH, $CF_3$, $OCF_3$, and halo; and $R^8$ is selected from the group consisting of $C_{1-4}$alkyl, aryl, and heteroaryl, with aryl, and heteroaryl, being unsubstituted or substituted with 1-5 groups independently selected from $C_{1-4}$alkyl, $OC_{1-4}$alkyl, OH, $CF_3$, $OCF_3$, and halo.

Another class of embodiments of this aspect of the invention is characterized by the compounds of Formula I including those in which each --- independently is a single bond or a double bond; $R^1$ is OH; $R^2$ and $R^3$ together form =$CH_2$; $R^4$ is $CH_3$; $R^5$ and $R^6$ are both H, with the proviso that when --- between carbon-23 and carbon-24 is a double bond, then $R^5$ is absent; $R^7$ is selected from the group consisting of H, $C_{1-4}$alkyl, $C_{2-5}$alkenyl, aryl and heteroaryl, with aryl and heteroaryl being unsubstituted or substituted with 1 to 5 groups independently selected from $C_{1-4}$alkyl, $OC_{1-4}$alkyl, OH, $CF_3$, $OCF_3$, and halo; and $R^8$ is selected from the group consisting of $C_{1-4}$alkyl, aryl, and heteroaryl, with aryl, and heteroaryl, being unsubstituted or substituted with 1-5 groups independently selected from $C_{1-4}$alkyl, $OC_{1-4}$alkyl, OH, $CF_3$, $OCF_3$, and halo.

In a specific embodiment of the present invention, a compound of Formula II includes:

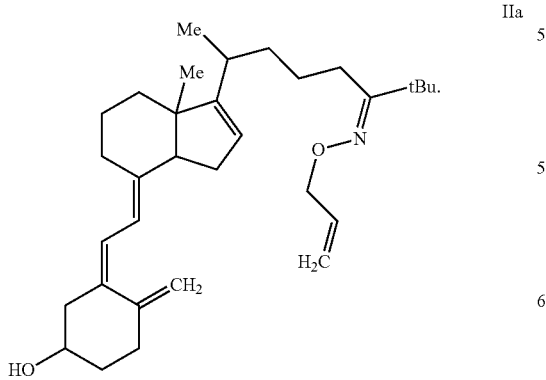

IIa

The compounds of Formula II have more than one chiral center. Where the compounds according to the invention possess more than one chiral center, they may exist as stereoisomers. It is to be understood that all such isomers and mixtures thereof in any proportion are encompassed within the scope of the present invention. The stereochemistry of the A, C and D rings and at the C20 position of the compounds of the invention is preferably that of natural 25-dihydroxyvitamin $D_3$. Therefore the present invention preferably provides compounds of Formula I, and pharmaceutically acceptable acid addition salts and hydrates thereof, having the following relative stereochemistry:

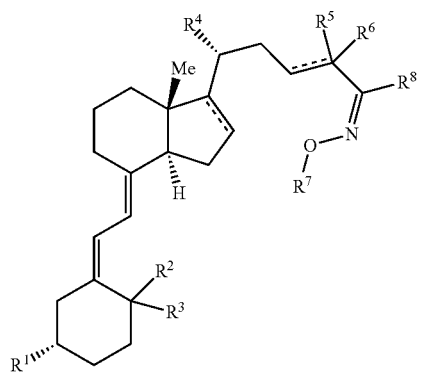

wherein --- and $R^1$-$R^8$ are as defined above. One class of embodiments is characterized by --- being a double bond between carbon-23 and carbon-24 with 'E' stereochemistry.

It is to be understood that, while the relative stereochemistry of the compounds of Formula II is preferably as shown above, such compounds of Formula II may also contain certain amounts (e.g. less than 20%, preferably less than 10%, more preferably less than 5%) of compounds of Formula II having alternate stereochemistry. For example, a compound of Formula II having the 3β-stereochemistry of natural 25-dihydroxyvitamin $D_3$, shown above, may contain less then 20%, preferably less then 10%, more preferably less then 5%, of a compound of Formula II having the unnatural 3α-stereochemistry.

Another class of embodiments of the present invention is characterized by a compound of Formula II:

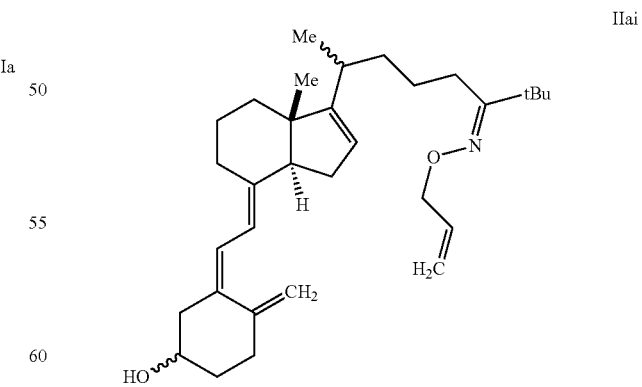

IIai wherein the symbol, ⁓, represents that the carbon atom to which it is bound can have either R or S stereochemistry.

In a specific embodiment of the present invention, a compound of Formula II includes:

IIaii

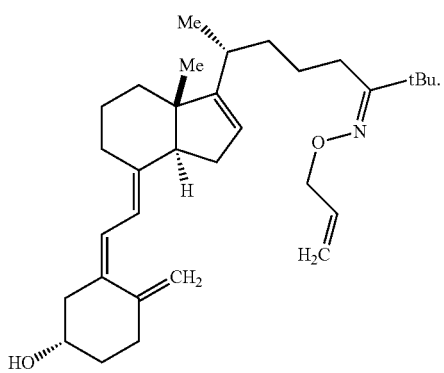

In one aspect, the invention provides compounds of Formula III, or a pharmaceutically acceptable salt, solvate, or hydrate thereof:

Formula III

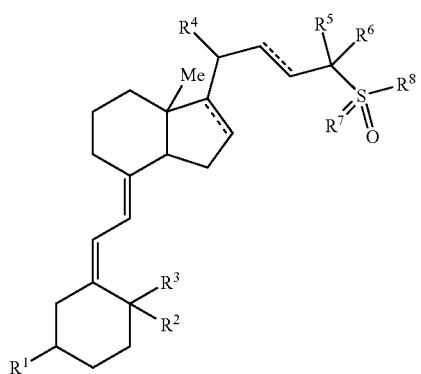

wherein each --- independently is a single bond or a double bond;
$R^1$ is selected from the group consisting of OH, $OC_{1-6}$alkyl, and halo;
$R^2$ and $R^3$ are each independently H or halo, or together form $=CH_2$;
$R^4$ is $C_{1-6}$alkyl;
$R^5$ and $R^6$ are each independently H, halo, $C_{1-4}$alkyl, or can be taken, together with the carbon atom to which they are bound, to form a $C_{3-6}$cycloalkyl ring;
$R^7$ is selected from the group consisting of O, NH, $N(C_{1-6}$alkyl), and $NC(O)R^9$;
$R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo, OH, $OCF_3$, SH, $SC_{1-4}$alkyl, $NH_2$, $NHC_{1-4}$alkyl, $N(C_{1-4}$alkyl)$(C_{1-4}$alkyl), and CN; and,
$R^9$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo.

One contemplated class of embodiments of this aspect of the invention is characterized by $R^1$ being OH or halo, more preferably OH or F, and further preferably OH.

Another class of embodiments of this aspect of the invention is characterized by $R^2$ and $R^3$ each being H or together forming $=CH_2$; more preferably $R^2$ and $R^3$ together form $=CH_2$.

Another class of embodiments of this aspect of the invention is characterized by $R^4$ being $C_{1-4}$alkyl, and more preferably $CH_3$.

Another class of embodiments of this aspect of the invention is characterized by $R^7$ being selected from the group consisting of O, NH, and $N(C_{1-6}$alkyl), and more preferably.

Another class of embodiments of this aspect of the invention is characterized by $R^8$ being selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo; more preferably $R^8$ is selected from the group consisting of $C_{1-4}$alkyl, aryl and heteroaryl, wherein each of aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo; further preferably $R^8$ is selected from the group consisting of $C_{1-4}$alkyl and aryl, wherein aryl is either unsubstituted or substituted with 1 to 5 substituents independently selected from the group consisting of $C_{1-4}$alkyl, $OC_{1-4}$alkyl, $CF_3$, $NO_2$, and halo.

Another class of embodiments of this aspect of the invention is characterized by the compounds of Formula III including those in which each --- independently is a single bond or a double bond; $R^1$ is OH or F; $R^2$ and $R^3$ together form $=CH_2$; $R^4$ is $CH_3$; $R^5$ and $R^6$ are each independently H, halo, $C_{1-2}$alkyl, or can be taken, together with the carbon atom to which they are bound, to form a $C_{3-4}$cycloalkyl ring; $R^7$ is O or NH; and $R^8$ is selected from the group consisting of $C_{1-4}$alkyl, aryl and heteroaryl, wherein each of aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo.

Another class of embodiments of this aspect of the invention is characterized by the compounds of Formula III including those in which each --- independently is a single bond or a double bond; $R^2$ and $R^3$ together form $=CH_2$; $R^4$ is $CH_3$; $R^5$ and $R^6$ are each independently H, F, Cl, $CH_3$, or can be taken, together with the carbon atom to which they are bound, to form a $C_{3-4}$cycloalkyl ring; $R^7$ is O or NH; and $R^8$ is selected from the group consisting of $C_{1-4}$alkyl and aryl, wherein aryl is either unsubstituted or substituted with 1 to 5 substituents independently selected from the group consisting of $C_{1-4}$alkyl, $OC_{1-4}$alkyl, $CF_3$, $NO_2$, and halo.

In specific embodiments of the present invention, the compounds of Formula III include:

IIIa

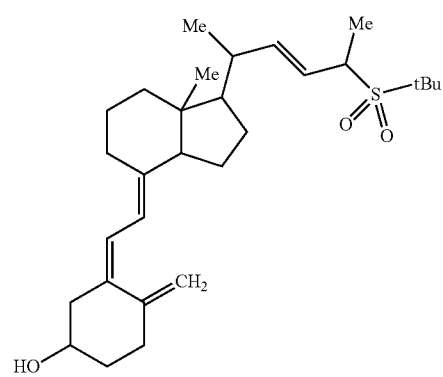

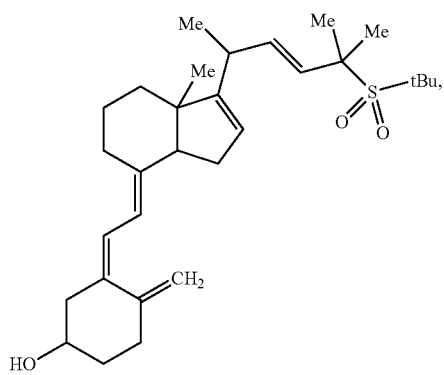
IIIb
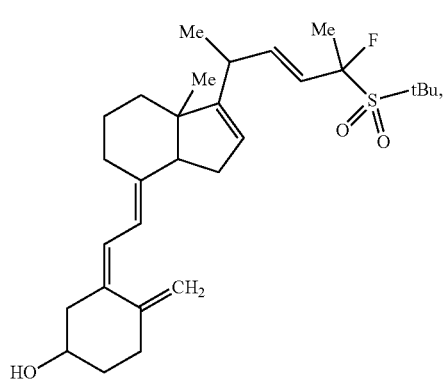
IIIc
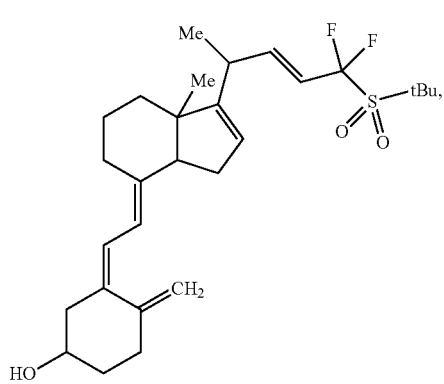
IIId
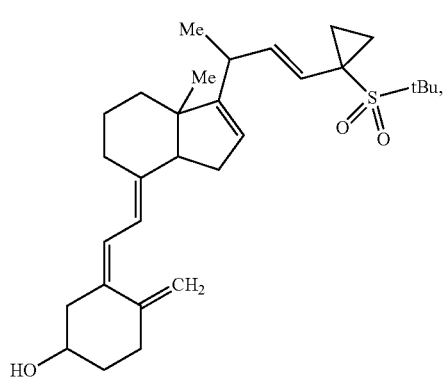
IIIe
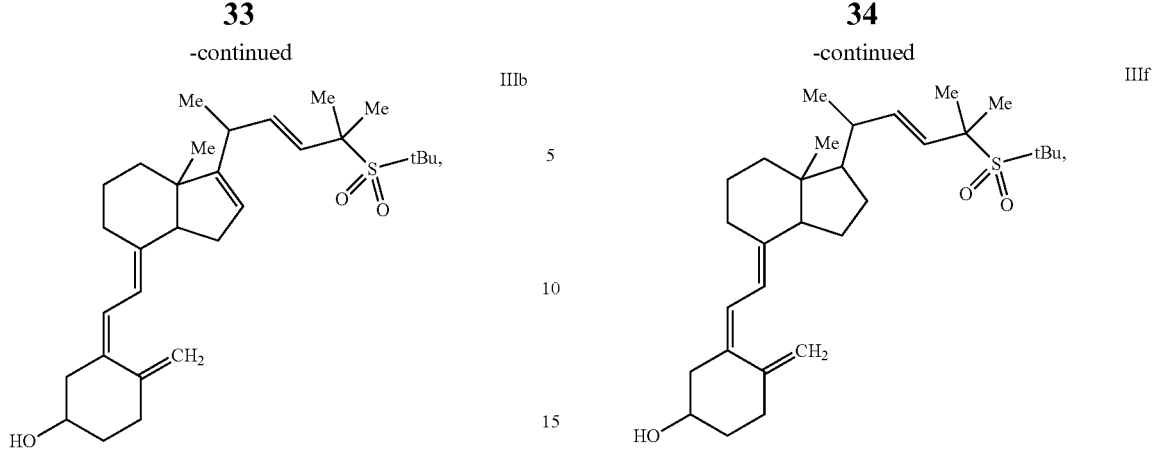
IIIf
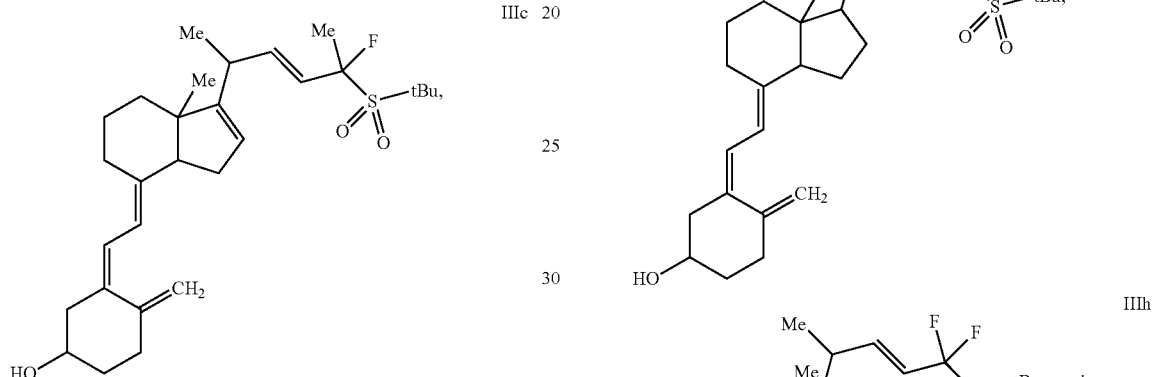
IIIg
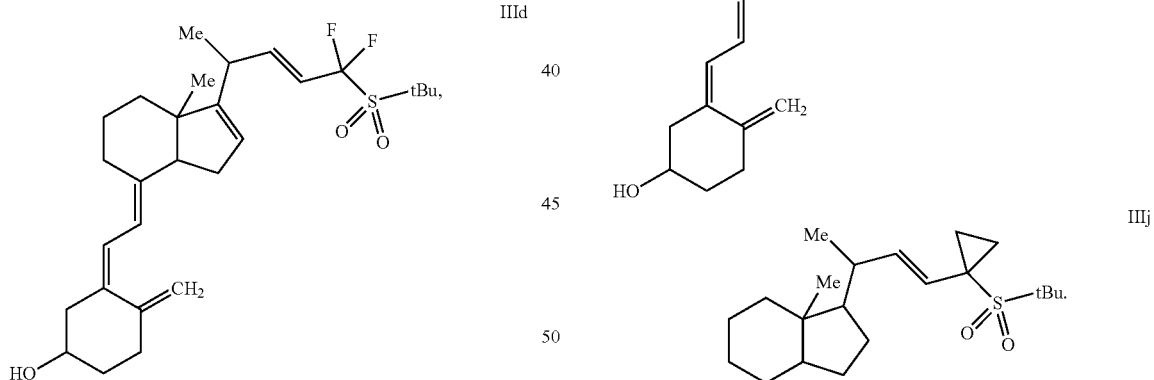
IIIh
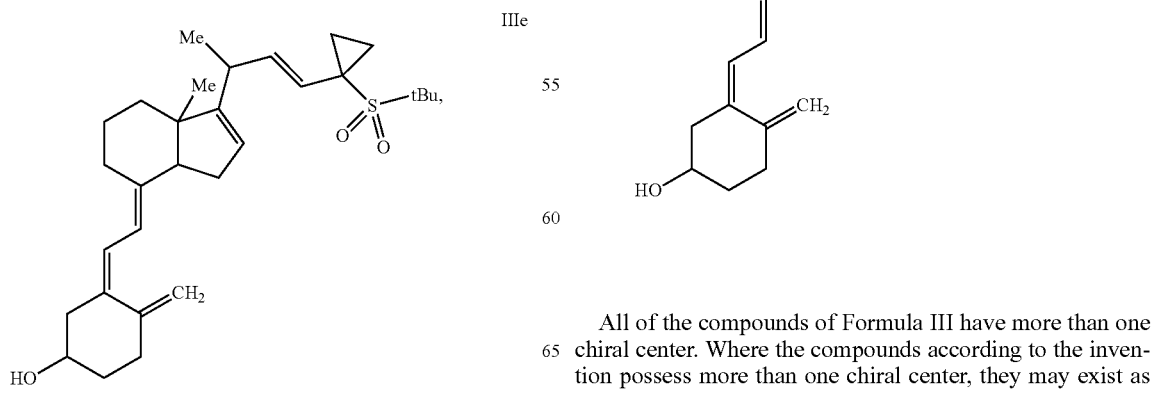
IIIj
All of the compounds of Formula III have more than one chiral center. Where the compounds according to the invention possess more than one chiral center, they may exist as stereoisomers. It is to be understood that all such isomers and mixtures thereof in any proportion are encompassed within the scope of the present invention. The stereochemistry of the A, C and D rings and at the C20 position of the compounds of the invention is preferably that of natural 25-dihydroxyvitamin $D_3$. When $R^7$ is not O, the stereochemistry at the sulfur atom may be either R or S. Therefore the present invention preferably provides compounds of Formula I, and pharmaceutically acceptable acid addition salts and hydrates thereof, having the following relative stereochemistry:

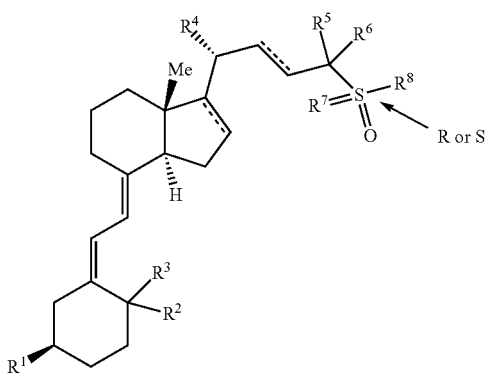

wherein --- and $R^1$-$R^8$ are as defined above. One class of embodiments is characterized by --- being a double bond between carbon-22 and carbon-23 with 'E' stereochemistry.

It is to be understood that, while the relative stereochemistry of the compounds of Formula III is preferably as shown above, such compounds of Formula III may also contain certain amounts (e.g. less than 20%, preferably less than 10%, more preferably less than 5%) of compounds of Formula III having alternate stereochemistry. For example, a compound of Formula III having the 3β-stereochemistry of natural 25-dihydroxyvitamin $D_3$, shown above, may contain less then 20%, preferably less then 10%, more preferably less then 5%, of a compound of Formula III having the unnatural 3α-stereochemistry.

In embodiments of the present invention, the compounds of Formula III include:

IIIai
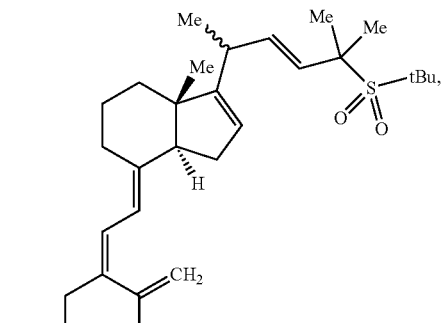

IIIbi
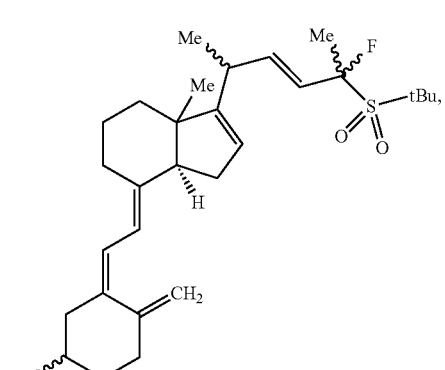

IIIci
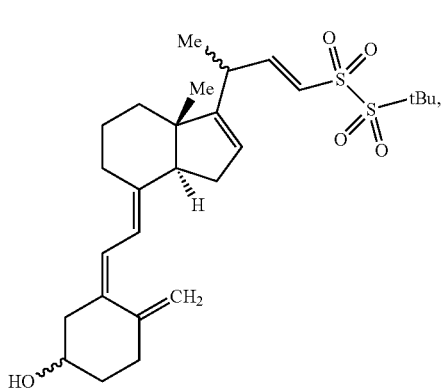

IIIdi

IIIei
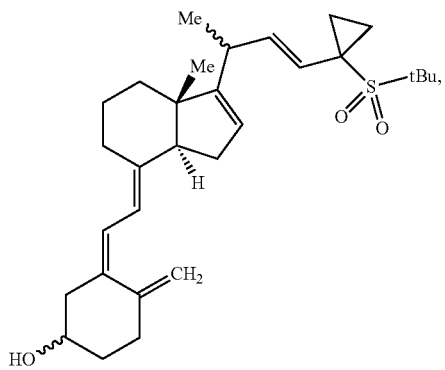

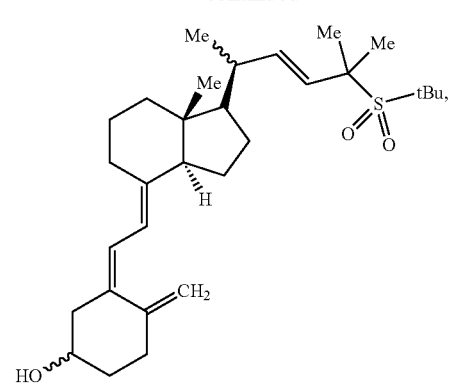
IIIfi
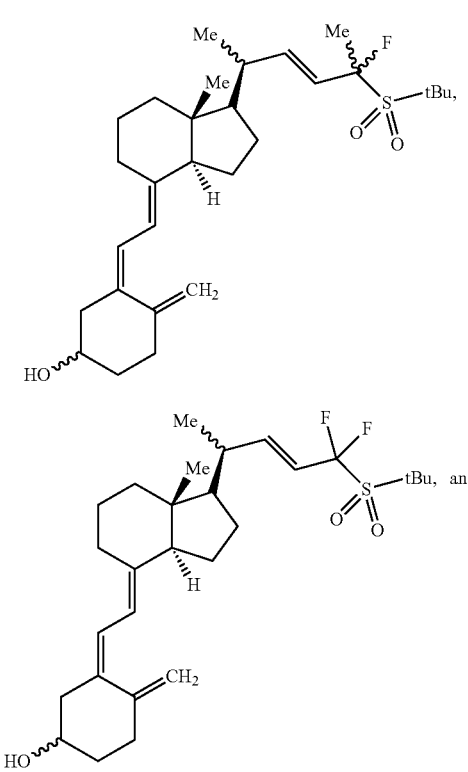
IIIgi
IIIhi
IIIji
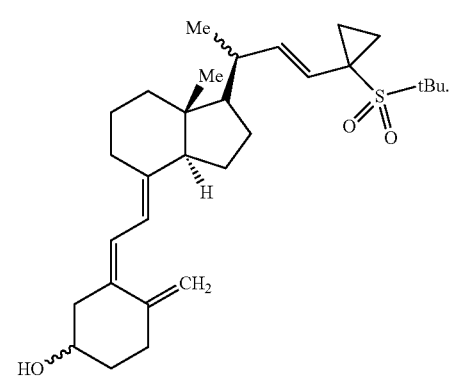
wherein the symbol, ⌇, represents that the carbon atom to which it is bound can have either R or S stereochemistry.
In specific embodiments of the present invention, the compounds of Formula III include:
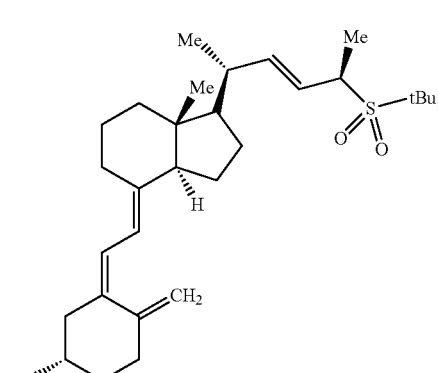
IIIaii
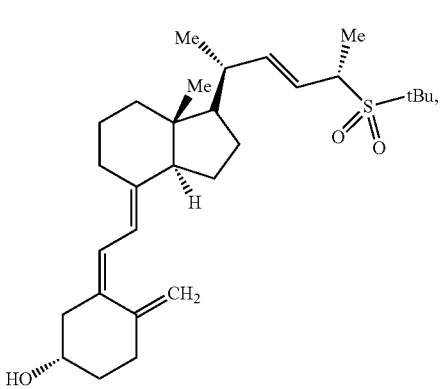
IIIaiii
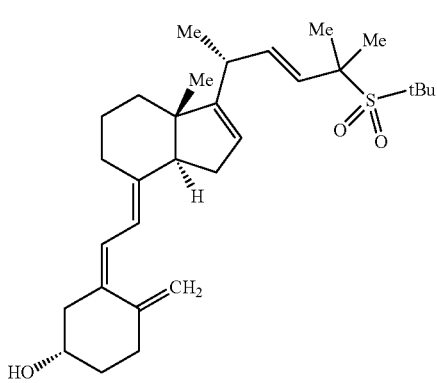
IIIbii
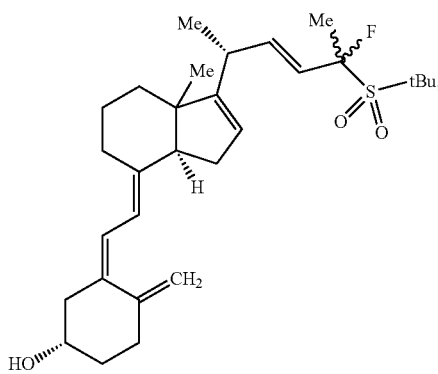
IIIcii

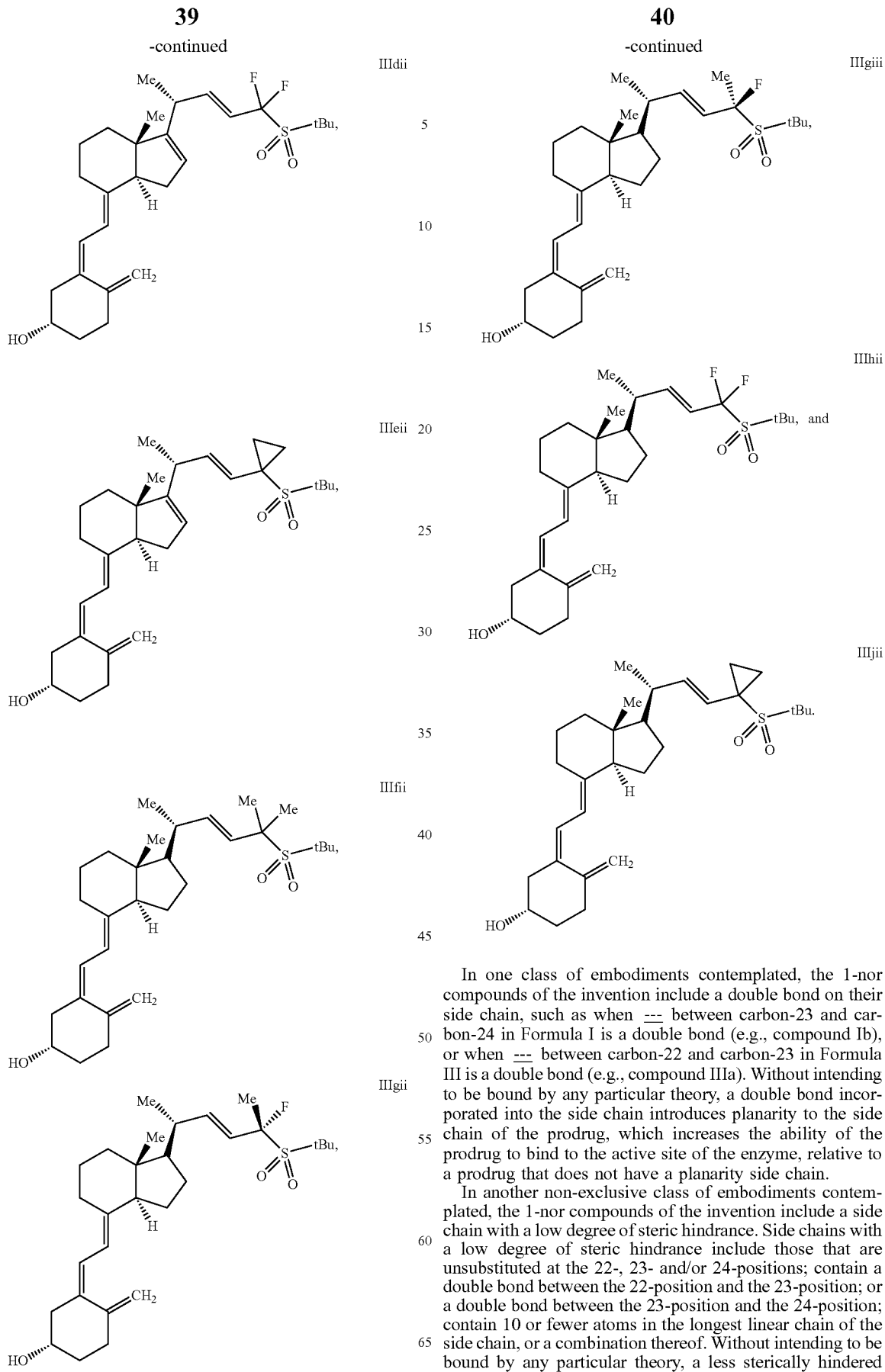

In one class of embodiments contemplated, the 1-nor compounds of the invention include a double bond on their side chain, such as when --- between carbon-23 and carbon-24 in Formula I is a double bond (e.g., compound Ib), or when --- between carbon-22 and carbon-23 in Formula III is a double bond (e.g., compound IIIa). Without intending to be bound by any particular theory, a double bond incorporated into the side chain introduces planarity to the side chain of the prodrug, which increases the ability of the prodrug to bind to the active site of the enzyme, relative to a prodrug that does not have a planarity side chain.

In another non-exclusive class of embodiments contemplated, the 1-nor compounds of the invention include a side chain with a low degree of steric hindrance. Side chains with a low degree of steric hindrance include those that are unsubstituted at the 22-, 23- and/or 24-positions; contain a double bond between the 22-position and the 23-position; or a double bond between the 23-position and the 24-position; contain 10 or fewer atoms in the longest linear chain of the side chain, or a combination thereof. Without intending to be bound by any particular theory, a less sterically hindered side chain increases the ability of the prodrug to bind to the active site of the enzyme, relative to a prodrug with more sterically hindered side chain. Examples of prodrugs that have a less sterically hindered side chain include compound Ib and Ig.

In another non-exclusive class of embodiments contemplated, the 1-nor compounds of the invention include a less sterically hindered side chain that itself has a double bond. Examples of these compounds include compound Ib, If, and Ih.

The present invention also encompasses 1-nor analogs of other known approved or experimental active Vitamin D compounds, such as, for example, 1-nor prohormone forms of paricalcitol, alfacacidiol, 22-oxacalcitriol (OCT), calcipotril (i.e., DOVONEX), falecalcitriol, tacalcitol, EB1089, KH1060, ED-71, gemini Vitamin D analogs (e.g., BXL024), $1\alpha,25(OH)_2$-16-ene-20-cyclopropylvitamin $D_3$ (e.g., BXL-62), and others. Examples of these compounds are shown below:

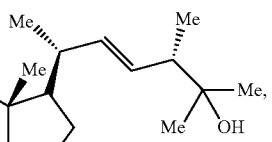

1-Nor-Paricalcitol (paricalcitol is indicated for treatment of SHPT)

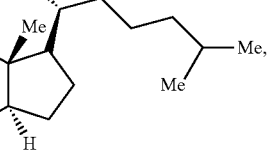

1-Nor-Alphacalcidol (alphacalcidol is indicated for the treatment of hypocalcemia, secondary hyperparathyroidism, and osteodystrophy in patients with chronic renal failure)

1-Nor-22-Oxacalcitriol (22-oxacalcitriol is indicated for the treatment of SHPT and psoriasis)

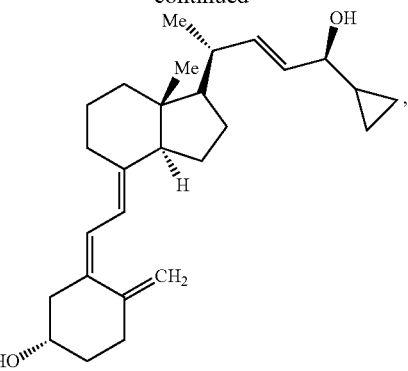

1-Nor-Calcipotriol (calcipotriol is indicated for the treatment of psoriasis)

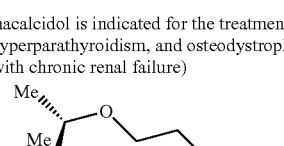

1-Nor-Falecalcitriol (falecalcitriol is indicated for the treatment of SHPT)

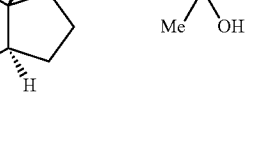

1-Nor-Tacalcitol (tacalcitol is indicated for the treatment of psoriasis)

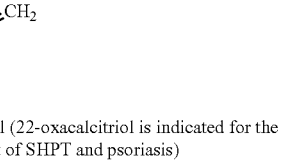

1-Nor-EB1089

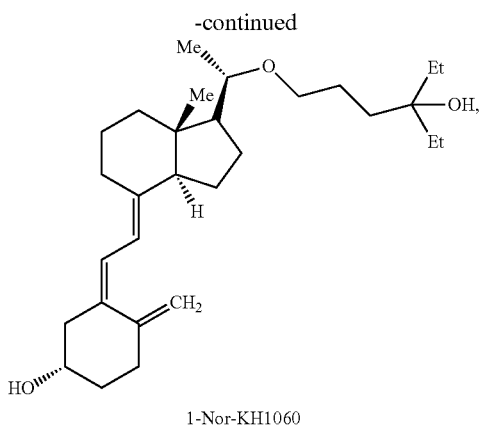

1-Nor-KH1060

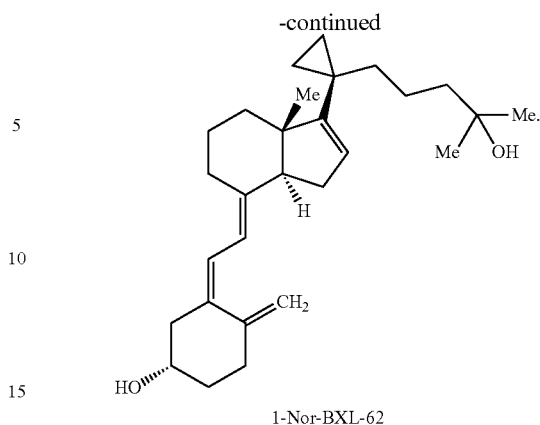

1-Nor-BXL-62

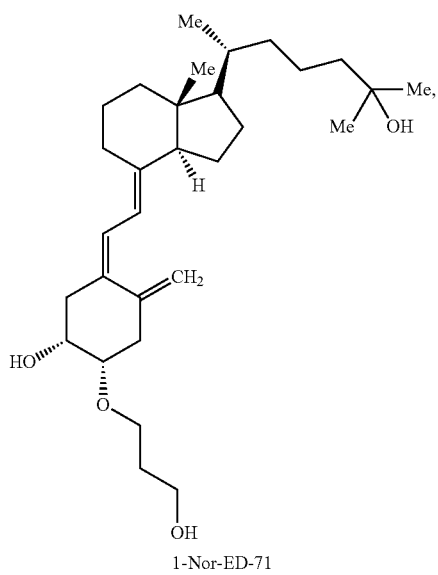

1-Nor-ED-71

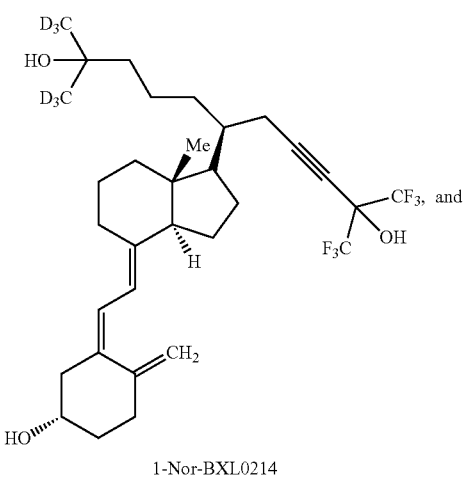

1-Nor-BXL0214

The present invention includes ester derivatives of the prodrug compounds of the invention. These ester derivatives are esters that are formed with one or more available hydroxyl groups of the prodrug compounds described herein. Contemplated esters include phenyl esters, aliphatic (C8-C24) esters, acyloxymethyl esters, carbamates, and amino acid esters. For example, when $R^1$ is OH in a prodrug compound described herein, it may be acylated using a carboxylic acid or an activated form of a carboxylic acid in the presence of a base, and optionally, in an inert solvent (e.g. an acid chloride in pyridine). As used herein, the term "activated form of a carboxylic acid" refers to the general formula R(C=O)X, wherein X is a leaving group (e.g. N-hydroxysuccinimide, halogen, alcohol, sulfonate ester, carboxylate). Contemplated activated forms of carboxylic acids include acyl chlorides, anhydrides, and esters.

The present invention also includes radiolabeled forms of compounds of the invention, for example, compounds of the invention labeled by incorporation within the structure $^3$H or $^{14}$C or a radioactive halogen such as $^{125}$I.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C.

As previously described, the Vitamin D prohormones (e.g. 25-hydroxyvitamin $D_3$) are metabolized in the kidneys into the active hormones (e.g. 1α,25-dihydroxyvitamin $D_3$) by CYP27B1 as shown, for example, below:

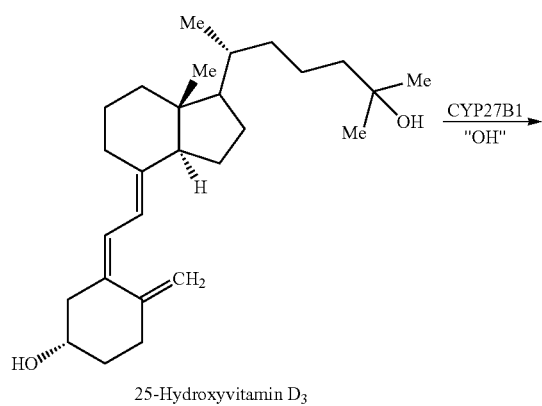

25-Hydroxyvitamin D₃

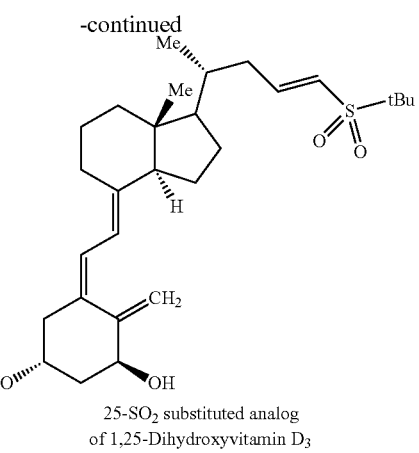

25-SO₂ substituted analog
of 1,25-Dihydroxyvitamin D₃

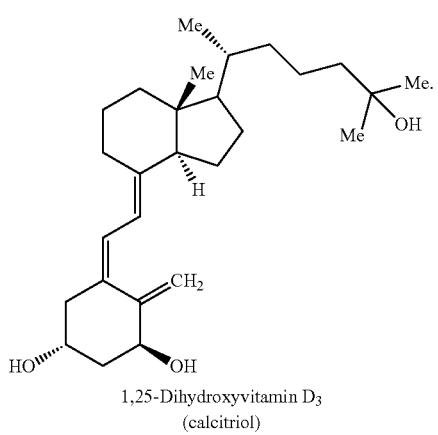

1,25-Dihydroxyvitamin D₃
(calcitriol)

The blood levels of 1,25-dihydroxyvitamin D₃ and the substrate 25-hydroxyvitamin D₃ prohormone, and regulation thereof, can be affected by vitamin D hormone analogs, 24-sulfoximine vitamin D₃ compounds, oxime analogs of 1α,25-dihydroxyvitamin D₃, and 25-SO₂ substituted analogs of 1α,25-dihydroxyvitamin D₃. The compounds of the invention will be metabolized into active hormones by CYP27B1 as shown, for example, below for compound Ibii.

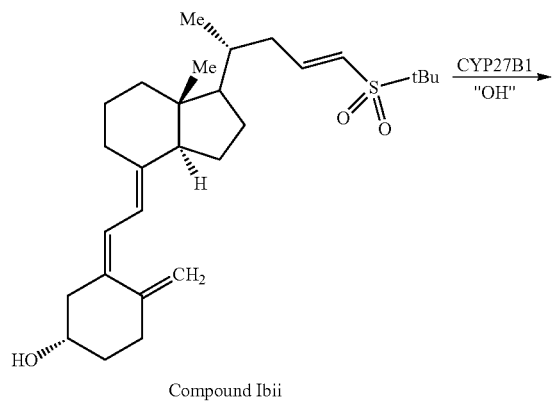

Compound Ibii

Analogous to 25-hydroxyvitamin D₃, which has a binding affinity to the VDR that is 100-fold lower than 1,25-hydroxyvitamin D₃, the 1-deoxy compounds of Formulas I and II do not substantially bind to the VDR (see FIG. 1). As a consequence, physiological concentrations of these hormone precursors exert little, if any, biological actions without metabolism by CYP27B1. Therefore, the 1-deoxy compounds represented by Formulas I and II can act as effective prodrugs of their 1-hydroxylated, active counterparts, e.g. such as 24-sulfoximine, oxime, and 25-SO₂ substituted analogs of 1α,25-dihydroxyvitamin D₃. The compounds will provide slower, "on-demand" introduction of these low calcemic, anti-proliferative analogs of 1α,25-dihydroxyvitamin D₃ to the body.

Administration of the compounds of Formulas I and II as prodrugs of the low calcemic, anti-proliferative, CYP24 inhibitory analogs of 1α,25-dihydroxyvitamin D₃ (e.g. 24-sulfoximine, oxime, and 25-SO₂ substituted analogs) has advantages over administration of the corresponding 25-hydroxyvitamin D₃ prohormone. Direct administration of 25-hydroxyvitamin D₃ can produce surges or spikes in blood and intracellular 25-hydroxyvitamin D levels, thereby promoting toxicity manifesting as hypercalcemia and hypercalciuria. Without intending to be bound by any particular theory, it is believed that surges or spikes in blood and intracellular 25-hydroxyvitamin D levels can promote one or more disadvantages, including (a) competitive displacement of Vitamin D hormones from the serum Vitamin D Binding Protein (DBP) and excessive delivery of the displaced hormones to tissues containing VDR, and (b) transiently excessive renal and extrarenal production of Vitamin D hormones, which together can lead to local aberrations in calcium and phosphorus metabolism. In addition, these surges in blood 25-hydroxyvitamin D levels can promote catabolism of both Vitamin D and 25-hydroxyvitamin D by 24- and/or 26-hydroxylation in the kidney and other tissues, and down-regulation of hepatic production of Vitamin D prohormones, unnecessarily impeding the efficient repletion of Vitamin D insufficiency or deficiency, and, additional local aberrations in calcium and phosphorus homeostasis mediated by direct binding to VDR. Importantly, 25-hydroxyvitamin D₃ is believed to promote its intestinal absorption via a mechanism substantially involving transport to the liver in chylomicrons, rather than bound to the serum DBP. Delivery of 25-hydroxyvitamin D to the liver via chylomicrons is believed to significantly increase the likelihood of its catabolism. By administering the prodrugs of the invention instead of 25-hydroxyvitamin D₃, the slow or "on-demand" release of the low calcemic, anti-proliferative, selective CYP24 inhibitor analogs of 1α,25-dihydroxyvitamin $D_3$ would occur instead.

Accordingly, in another aspect the invention is related to a method of treating or preventing vitamin D deficiency by administering a compound of Formula I or II to a subject in need of vitamin D supplementation, either prophylactically to prevent vitamin D insufficiency or deficiency, or therapeutically to supplement low serum vitamin 25(OH)D levels with a prodrug of the invention to provide a sufficient pool of prohormone and prohormone analog for conversion to active vitamin D (native) and an analog thereof. The prodrugs of the invention are also useful for preventing or treating hyperparathyroidism, for example hyperparathyroidism secondary to CKD. In general, serum 25(OH)D values less than 5 ng/mL indicate severe deficiency associated with rickets and osteomalacia. Although 30 ng/mL has been suggested as the low end of the normal range, more recent research suggests that PTH levels and calcium absorption are not optimized until serum total 25(OH)D levels reach approximately 40 ng/mL. [See also Vieth, R. Prog Biophys Mol Biol. 2006 September; 92(1):26-32.]

Patients in need of vitamin D supplementation include healthy subjects and subjects at risk for vitamin D insufficiency or deficiency, for example, subjects with stage 1, 2, 3, 4 or 5 chronic kidney disease; infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D in skin during exposure to sunlight and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with an Sun Protection Factor (SPF) of 8 reduces production of vitamin D by 95%, and higher SPFs may further reduce cutaneous vitamin D production); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenyloin, fosphenyloin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); subjects with osteoporosis and/or postmenopausal women. According to the Institute of Medicine's report on the Dietary Reference Intakes for vitamin D, food consumption data suggest that median intakes of vitamin D for both younger and older women are below current recommendations; data suggest that more than 50% of younger and older women are not consuming recommended amounts of vitamin D. Optionally excluded from the methods of the invention are therapeutic treatment of subjects suffering from renal osteodystrophy (including osteomalacia and osteitis fibrosa cystica).

In other aspects, the prodrugs of the invention are useful for the prophylactic or therapeutic treatment of vitamin D-responsive diseases, i.e., diseases where vitamin D, 25(OH)D or active vitamin D (e.g., 1,25(OH)$_2$D) prevents onset or progression of disease, or reduces signs or symptoms of disease. Such vitamin D-responsive diseases include cancer, for example (e.g., breast, lung, skin, melanoma, colon, colorectal, rectal, prostate and bone cancer). 1,25 (OH)$_2$D has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, chronic obstructive pulmonary disease, polycystic kidney disease (PKD), polycystic ovary syndrome, pancreatitis, nephritis, hepatitis, and/or infection. Vitamin D-responsive diseases have also been reported to include hypertension and cardiovascular diseases. Thus, the invention contemplates prophylactic or therapeutic treatment of subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

The compounds of Formulas I and II are prodrugs of hormones that selectively modulate CYP24, the enzyme that metabolizes 1α,25-dihydroxyvitamin $D_3$. Therefore, the levels of 1α,25-dihydroxyvitamin $D_3$ (either endogenous or administered as part of a chemotherapeutic regimen), or analogs thereof, may also be modulated with the prodrugs of Formulas I and II. Diseases that benefit from a modulation, in particular an increase, of the levels of 1α,25-dihydroxyvitamin $D_3$ can therefore be treated using a prodrug of a modulator of CYP24. By acting preferentially on CYP24, side effects caused by interaction with other enzymes and receptors may be reduced. Accordingly, the present invention provides a method for treating diseases which benefit from a modulation, preferably an increase, of the levels of 1α,25-dihydroxyvitamin $D_3$, or an analog of 1α,25-dihydroxyvitamin $D_3$, comprising administering an effective amount of a compound of Formula I or II to a cell or animal in need thereof. The invention also includes the use of a compound of Formula I or II to treat diseases which benefit from a modulation, preferably an increase, of the levels of 1α,25-dihydroxyvitamin $D_3$, or an analog of 1α,25-dihydroxyvitamin $D_3$. Further, the invention includes a use of a compound of the invention to prepare a medicament to treat diseases which benefit from a modulation, preferably an increase, of the levels of 1α,25-dihydroxyvitamin $D_3$, or an analog of 1α,25-dihydroxyvitamin $D_3$.

Inhibition of CYP24 will inhibit the catabolism of 1α,25-dihydroxyvitamin $D_3$, or its analogs, which is expected to lengthen the biological lifetime of these compounds and thus allow smaller amounts of them to be used for effective disease treatment. Such smaller dosing is expected to avoid, or at least minimize, the hypercalcemic toxicity associated with medicinal use of 1α,25-dihydroxyvitamin $D_3$ and its analogs. Further, by inhibiting the catabolism of 1α,25-dihydroxyvitamin $D_3$, the prodrugs of the invention will increase the endogenous levels of this hormone, which will have similar beneficial therapeutic effects. Therefore, in an embodiment, the present invention provides a method for treating diseases which benefit from inhibiting the catabolism of 1α,25-dihydroxyvitamin $D_3$, or an analog of 1α,25-dihydroxyvitamin $D_3$, comprising administering an effective amount of the prodrug of the invention to a cell or animal in need thereof. The invention also includes the use of a prodrug of the invention to treat diseases which benefit from inhibiting the catabolism of 1α,25-dihydroxyvitamin $D_3$, or an analog of 1α,25-dihydroxyvitamin $D_3$. Further, the invention includes a use of a prodrug of the invention to prepare a medicament to treat diseases which benefit from inhibiting the catabolism of 1α,25-dihydroxyvitamin $D_3$, or an analog of 1α,25-dihydroxyvitamin $D_3$.

Diseases which will benefit for a modulation in the levels of 1α,25-dihydroxyvitamin $D_3$ include, but are not limited to:

(i) in the parathyroid—hyper- and hypoparathyroidism, osudohypoparathyroidism, secondary hyperparathyroidism;

(ii) in the pancreas—diabetes;

(iii) in the thyroid—medullary carcinoma;

(iv) in the skin psoriasis, wound healing;

(v) in the lung—sarcoidosis and tuberculosis;

(vi) in the kidney—chronic renal disease, hypophsphtatemic vitamin D resistant rickets (VDDR), vitamin D dependent rickets;

(vii) in the bone—anticonvulsant treatment, fibrogenisis imperfecta ossium, osteitits fibrosa cystica, osteomalacia, osteoporosis, osteopenia, osteosclerosis, renal osteodytrophy, rickets;

(viii) in the intestine—glucocorticoid antagonism, idopathic hypercalcemia, malabsorption syndrome, steatorrhea, tropical sprue; and autoimmune disorders.

For example, the disease that benefits from a modulation in the levels of 1α,25-dihydroxyvitamin $D_3$, or an analog of 1α,25-dihydroxyvitamin $D_3$, can be selected from cancer, dermatological disorders (for example psoriasis), parathyroid disorders (for example hyperparathyroidism and secondary hyperparathyroidism), bone disorders (for example osteoporosis) and autoimmune disorders.

In accordance with a further aspect of the present invention, the disease that benefits from a modulation, in particular an increase, in the levels of 1α,25-dihydroxyvitamin $D_3$, or an analog of 1α,25-dihydroxyvitamin $D_3$, is a cell proliferative disorder. Accordingly, there is provided a method for modulating cell proliferation (preferably inhibiting cell proliferation) and/or promoting cell differentiation, comprising administering an effective amount of a prodrug of the invention to a cell or animal in need thereof. The invention also includes a use of a prodrug of the invention to modulate cell proliferation (preferably to inhibit cell proliferation) and/or to promote cell differentiation. The invention further includes a use of a prodrug of the invention to prepare a medicament to modulate cell proliferation (preferably to inhibit cell proliferation) and/or to promote cell differentiation.

In particular, the method of the invention is useful in inhibiting the proliferation of abnormal but not normal cells. Abnormal cells include any type of cell that is causative of or involved in a disease or condition and wherein it is desirable to modulate or to inhibit the proliferation of the abnormal cell, or to promote its differentiation, in order to treat the disease or condition. Examples of abnormal cells include malignant or cancerous cells as well as cells that over-proliferate in inflammatory conditions such as psoriasis.

In another embodiment of the present invention, the disease that benefits from a modulation, in particular an increase, in the levels of 1α,25-dihydroxyvitamin $D_3$, or an analog of 1α,25-dihydroxyvitamin $D_3$, is cancer. Accordingly, the present invention provides a method of treating cancer comprising administering an effective amount of a prodrug of the invention to a cell or animal in need thereof. The invention also includes a use of a prodrug of the invention to treat cancer. The invention further includes a use of a prodrug of the invention to prepare a medicament to treat cancer. In embodiments of the invention, the cancer is selected from the group consisting of breast cancer, lung cancer, prostate cancer, colon and colorectal cancer, kidney cancer, head and neck cancer, pancreatic cancer, skin cancer, Kaposi's sarcoma and leukemia.

In another aspect, the invention provides a method of modulating CYP24 activity in a cell by administering an effective amount of a prodrug of the invention. In a further aspect, the invention provides a method of inhibiting CYP24 activity in a cell by administering an effective amount of a prodrug of the invention. The present invention also provides a use of a prodrug of the invention to modulate, preferably to inhibit, CYP24 activity. The present invention further provides a use of a prodrug of the invention to prepare a medicament to modulate CYP24 activity, preferably to inhibit, CYP24 activity.

The prodrugs of the invention can be used alone or in combination with other agents that modulate CYP24 activity, or in combination with other types of treatment (which may or may not modulate CYP24) for diseases that benefit from a modulation, preferably an increase, in the levels of 1α,25-dihydroxyvitamin $D_3$, or analogs thereof, and/or an inhibition of the catabolism of 1α,25-dihydroxyvitamin $D_3$, or an analog thereof. The compounds of the invention can be administered in combination with 1α,25-dihydroxyvitamin $D_3$ (calcitriol), an analog of 1α,25-dihydroxyvitamin $D_3$ or other vitamin D receptor agonists. Inhibiting catabolism of vitamin D receptor agonists such as 1α,25-dihydroxyvitamin $D_3$, or analogs thereof, will lengthen the biological lifetime or efficacy of these therapies and thus allow smaller amounts of the drug to be used for effective human chemotherapy; such smaller dosing will avoid, or at least reduce or minimize, the side effects, for example the hypercalcemic toxicity, associated with medicinal use of vitamin D agonist compounds. The present invention therefore provides a method of increasing the efficacy of a vitamin D receptor agonist comprising co-administering an effective amount of a prodrug of the invention and an effective amount of the vitamin D receptor agonist. Further the invention includes the use of a prodrug of the invention to increase the efficacy of a vitamin D receptor agonist and a use of a prodrug of the invention to prepare a medicament to increase the efficacy of a vitamin D receptor agonist. In embodiments of the invention, the vitamin D receptor agonist is 1α,25-dihydroxyvitamin $D_3$, or an analog thereof. By analog of 1α,25-dihydroxyvitamin $D_3$, it is meant a chemically modified analog of 1α,25-dihydroxyvitamin $D_3$ which is a vitamin D receptor agonist, and preferably one which exhibits a therapeutic profile similar to 1α,25-dihydroxyvitamin $D_3$. Examples of such compounds can be found in the following review articles, the contents of which are incorporated herein by reference: Pinette, K. V et al. "Vitamin D Receptor as a Drug Discovery Target", Mini Reviews in Med. Chem. 2003, 3:193-204; Mathieu, C. and Adorini, L. "The Coming of Age of 1,25-Dihydroxyvitamin $D_3$ Analogs as Immunomodulatory Agents", Trends in Mol. Med. 2002, 8:174-179; Carlberg, C. "Molecular Basis of the Selective Activity of Vitamin D Analogues", J. Cell. Bio. 2003, 88:274-281; Stein, M. S. and Wark, J. D. "An update on the therapeutic potential of vitamin D analogues", Expert Opin. Invest. Drugs 2003, 12:825-840; Bouillon, R. et al. "Structure-Function Relationships in the Vitamin D Endocrine System" Endocr. Rev. 1995, 16:200-257; and Nagpal, S. et al. "Vitamin D Analogs: Mechanism of Action and Therapeutic Applications", Current Med. Chem. 2001, 8:1661-1679.

Treatments used in combination with the compounds of the present invention may be based on the disease type and do not have to specifically target CYP24 activity or the VDR. In a particular aspect of the present invention, the prodrugs of the invention are used in combination with other therapies and therapeutics to treat dermatological disorders, bone disorders, cancer and autoimmune disorders. Such therapies include, but are not limited to the following: for cancer: surgery, radiation, chemotherapies and biotherapies; for psoriasis: ultraviolet B radiation, chemotherapy and biotherapies.

One skilled in the art can determine which prodrugs of the invention would have therapeutic utility, for example, in inhibiting cell proliferation in any type of cancer or cell proliferative disorder. Prodrugs may be examined for their potency in inhibiting cell growth in cell proliferation assays such as inhibition of growth of murine keratinocyte cells (cell line PE) and for the inhibition of TPA-induced ornithine decarboxylase (ODC) activity as described in U.S. Pat. No. 5,830,885, the contents of which are incorporated herein by reference.

In addition to cancer, the prodrugs of the invention are useful in treating other conditions involving aberrant or abnormal cell proliferation. Other cell proliferative disorders that may be treated by the present invention include inflammatory diseases, allergies, autoimmune disease, graft rejection, psoriasis, restenosis, atherosclerosis, and any other disorder wherein it is desirable to inhibit, prevent or suppress cell growth. Prodrugs of the invention may be tested for their potency in a particular cell proliferation disorder using assays and techniques known to those of skill in the art. For example, the following references provide assays for various conditions: Rheumatoid Arthritis: "Regulation of IL-15—Simulated TNF-alpha Production by Rolipram", Journal of Immunology (1999) volume 163 page 8236 by C. S. Kasyapa et al.; Allergy: "A novel Lyn-Binding Peptide Inhibitor Blocks Eosinophil Differentiation, Survival, and Airway eosinophilic inflammation". Journal of Immunology (1999) volume 163 page 939 by T. Adachi et al.; Psoriasis: Journal of Immunology (2000) volume 165 page 224 "Inhibition of Keratinocyte apoptosis by IL-15: a new parameter in the pathegenosis of psoriasis" by R. Üchert; and Psoriasis: International Archives of allergy and Immunology (2000) Volume 123 page 275. "T-cell receptor mimic peptides and their potential application in T-cell mediated disease" by A. H. Enk.

The prodrugs of the invention are preferably formulated into pharmaceutical compositions for administration to human subjects in a biologically compatible form suitable for administration in vivo. Accordingly, in another aspect, the present invention provides a pharmaceutical composition comprising a prodrug of the invention in admixture with a pharmaceutically-acceptable excipient, e.g. a diluent or carrier. The present invention can further comprise a pharmaceutical composition comprising a prodrug of the invention and a vitamin D receptor agonist in admixture with a suitable a pharmaceutically-acceptable excipient. In one class of such embodiments of the invention, the vitamin D receptor agonist is 1α,25-dihydroxyvitamin $D_3$, or an analog thereof.

The compositions containing the prodrugs of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions can include, albeit not exclusively, solutions of the substances in association with one or more pharmaceutically acceptable vehicles or diluents, and contained in buffered solutions with a suitable pH and iso-osmotic with the physiological fluids.

The prodrugs of the invention may be used in the form of the free base, as ester prodrugs of the prodrugs of the invention, and in the form of solvates and as hydrates. All forms are within the scope of the invention.

In accordance with the methods of the invention, the described prodrugs or solvates thereof may be administered to a patient in a variety of forms depending on the selected route of administration, as will be understood by those skilled in the art. The compositions of the invention may be administered, for example, by oral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A prodrug of the invention thereof may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipients and used in the form of ingestible tablets, buccal tablets, troches, capsules, elixirs, suspensions, syrups, wafers, and the like.

A prodrug of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations may include one or more additional ingredients such as diluents, buffers, flavoring agents, binders, surface active agents, thickeners, lubricants, preservatives, e.g. methyl hydroxybenzoate (including anti-oxidants), emulsifying agents and the like.

Time-release compositions (e.g. sustained- or extended release) or directed (e.g., delayed) release compositions can be formulated, e.g. liposomes or those wherein the active compound is protected with differentially degradable coatings, such as by microencapsulation, multiple coatings, etc. It is also possible to freeze-dry the compounds of the invention and use the lypolizates obtained, for example, for the preparation of products for injection.

The prodrugs of the invention may be administered to a subject alone or in combination with pharmaceutically acceptable carriers, as noted above, the proportion of which is determined by the solubility and chemical nature of the compound, chosen route of administration and standard pharmaceutical practice.

The dosage of the prodrugs and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. For example, in the topical treatment, ointments, creams, or lotions containing from 1-1000 µg/g of a compound of the invention may be administered. Oral preparations may be formulated, preferably as tablets, capsules, or drops, containing from 0.5-1000 µg of a prodrug of the invention, per dosage unit. The compounds of the invention may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

In addition to the above-mentioned therapeutic uses, the prodrugs of the invention are also useful in diagnostic assays, screening assays and as research tools.

In diagnostic assays the prodrugs of the invention may be useful in identifying or detecting a cell proliferative disorder. In such an embodiment, the prodrugs of the invention may be radiolabelled (as hereinbefore described) and contacted with a population of cells. The presence of the radiolabel on the cells may indicate a cell proliferative disorder.

In screening assays, the prodrugs of the invention may be used to identify other compounds that modulate cell proliferation or CYP24 activity. As research tools, the compounds of the invention may be used in receptor binding assays and assays to study the localization of CYP24. In such assays, the compounds may also be radiolabelled.

EXAMPLES

The following examples are provided for illustration and are not intended to limit the scope of the invention. It should be appreciated by those of skill in the art that many changes can be made in the specific embodiments which are disclosed and still obtain a like or similar result without departing from the spirit and scope of the invention.

The NMR spectra were recorded on a Bruker 400 MHz spectrometer. Chemical shift values are recorded in δ units (ppm). Solvents and chemicals were obtained from either the Aldrich Chemical Company or Acros Organics. IR spectroscopy was performed on a Perkin-Elmer series FT-IR instrument. UV spectroscopy was performed on a Varian Cary 50 Conc UV-Vis spectrophotometer. Mass spectrometry was performed on a VG-70S magnetic sector mass spectrometer. Optical rotation was determined using Jasco P-1010.

General Procedures

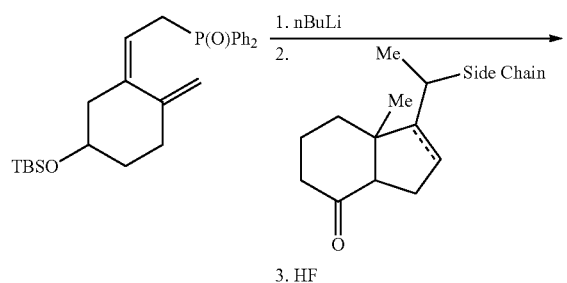

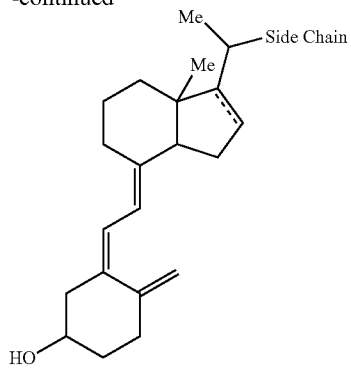

In general, the 1-nor compounds of the invention can be synthesized by reacting either 1-deoxy-A-ring-phosphine oxide or 1-deoxy-19-nor-A-ring-phosphine oxide with a ketone precursor having a desired D-ring and a desired side chain by using n-butyllithium and hydrofluoric acid or camphorsulfonic acid.

Enantiomerically pure 1-deoxy-A-ring-phosphine oxide can be prepared using a procedure by Wilson, S. R. et. al. in *Bioorganic Chemistry*, 1995, 23, 22-32, incorporated herein by reference. Kutner et al., *Bioorganic Chemistry*, 23:22-32 (1995), and Toh and Okamura, *J. Org. Chem.* 48:1414-1417 (1983), each incorporated herein by reference, also provide methods for synthesizing the 1-deoxy-A-ring-phosphine oxide.

The 1-deoxy-19-nor-A-ring-phosphine oxide precursor can be prepared according to procedures described in Perlman et al., Tetrahedron Letters 32(52):7663-7666 (1991), incorporated herein by reference, as shown in the scheme shown below.

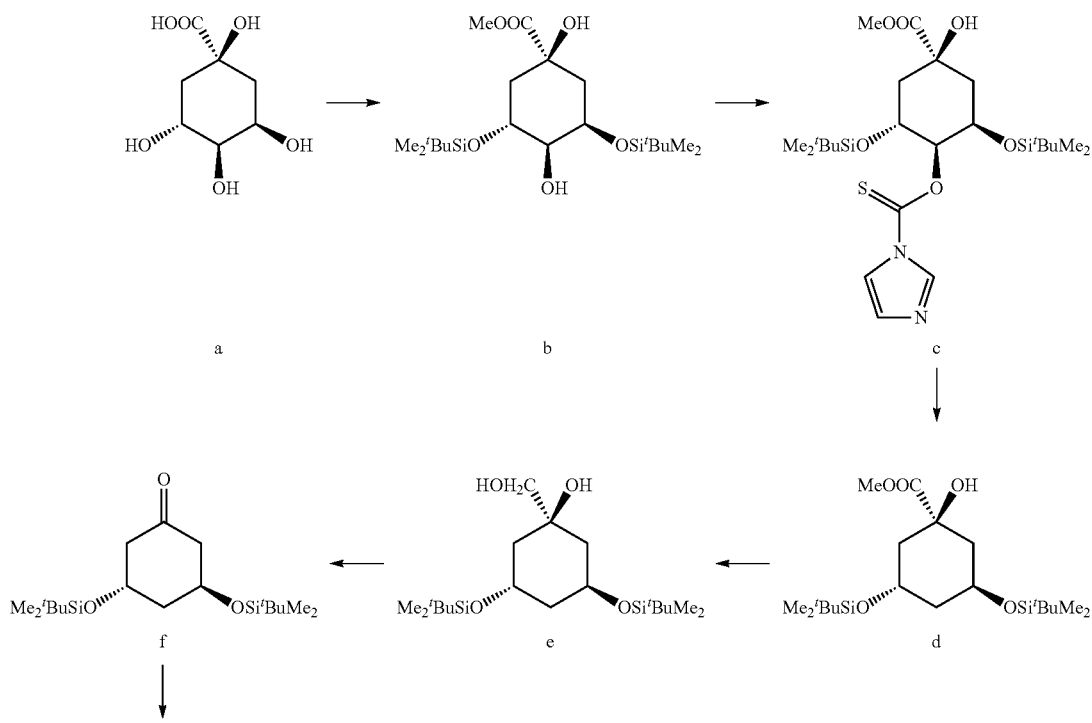

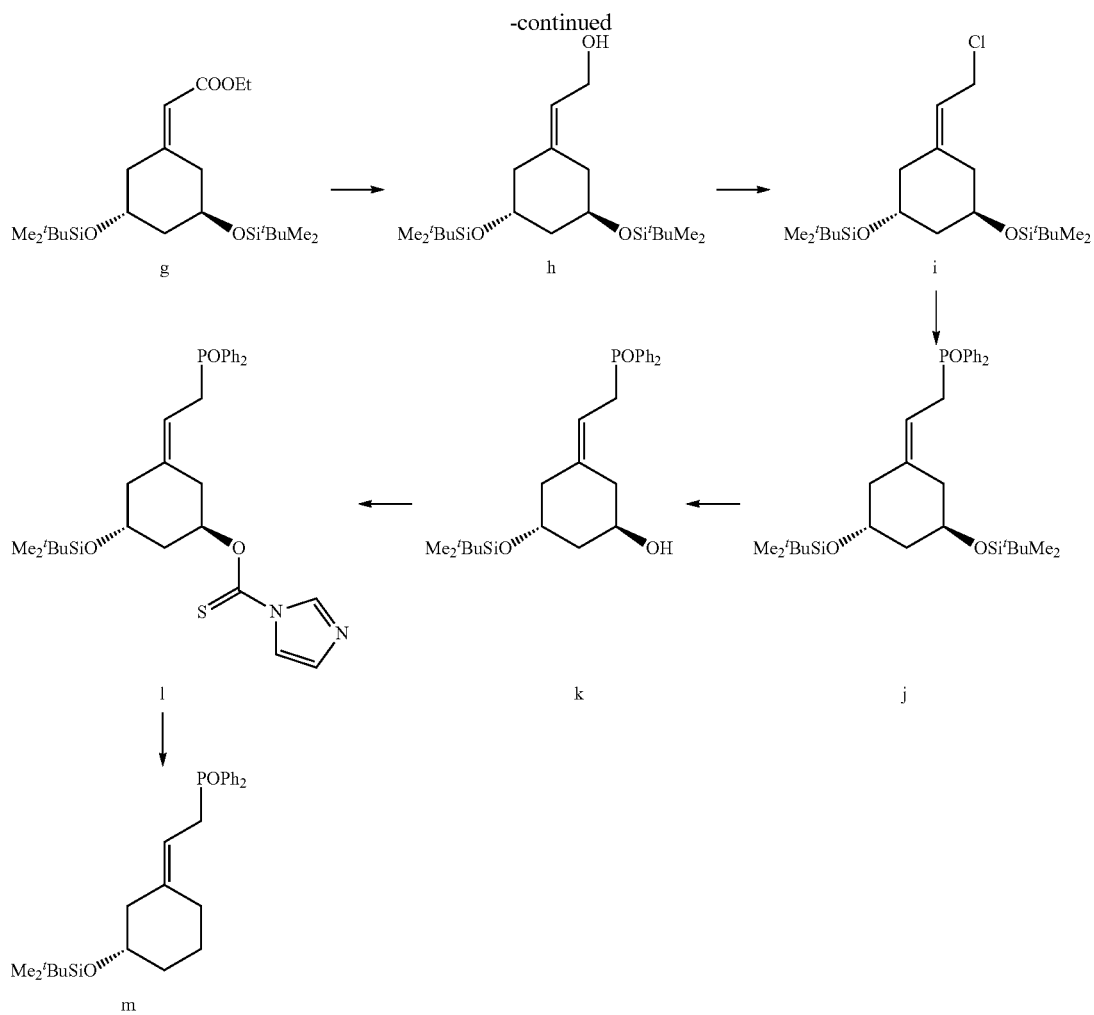

For example, compound a is esterified and the hydroxyl groups are protected to result in compound b (p-TsOH, MeOH, rt, 24 h, 92%; TBDMSCl, TEA, DMF, rt, 18 h, 70%). The thioimidazoline, c, is prepared through reaction of b with 1,1'-thiocarbonyl-diimidazole in methylene chloride (60 h, rt, 90%). Radical deoxygenation of c with tributyltin hydride in the presence of azobisisobutyronitrile (AIBN) produces the desoxy-ester, d (Bu₃SnH, AIBN, toluene, 80° C., 2 h, 90%). Ester d is reduced to the alcohol, e (DIBAL-H, toluene, −78° C., 2 h, 60%), which then undergoes oxidation to form cyclohexanone derivative f (saturated NaIO₄ in water, MeOH, 0° C., 30 min, 78%), Reaction of f with ethyl (trimethylsilyl)acetate in the presence of lithium diisopropylamide (LDA) in THF (−78° C., 2 h, 86%) produces the cyclohexyldiene ester, g. The latter is reduced to the allylic alcohol, h (DIBAL-H, toluene, −78° C., 1 h, 78-95%), which is converted to chloride i by reaction with the complex made from N-chlorosuccinimide and dimethyl sulfide (−25° C., then 0° C., 80%). This chloride is treated with lithium diphenylphosphide 0° C. (−78° C., 30 min), followed by oxidation with hydrogen peroxide, to form compound j. Compound j is partially deprotected to form compound k, which is dehydroxylated as described for compound c, to result in compound m. Compound m can react with a ketone precursor by methods described herein to form the 19-nor prodrugs of the invention.

The method of synthesizing the ketone precursor is dependent on the exact composition of the ketone (e.g., D-ring and side chain compositions). Methods of preparing Vitamin D ketone precursors having saturated or unsaturated D-rings and variable side chains are known to one skilled in the art. For example, U.S. Pat. No. 7,101,865, incorporated herein by reference, describes the synthesis of a ketone precursor of compound Ieii in Example 2.

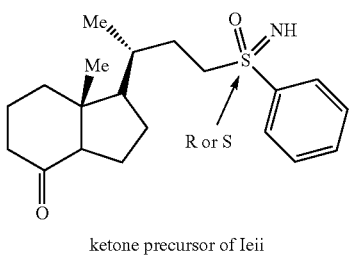

ketone precursor of Ieii

Specific experimental procedures for the conjugation of 1-deoxy-A-ring-phosphine oxide with ketone having specific D-rings and specific side chains are described in the following examples.

Example 1: Synthesis of 3-(2-{1-[4,4-Difluoro-1-methyl-4-(2-methyl-propane-2-sulfonyl)-butyl]-7α-methyl-3,3α,5,6,7,7a-hexahydro-inden-4-ylidene}-ethylidene)-4-methylene-cyclohexanol (Iaii)
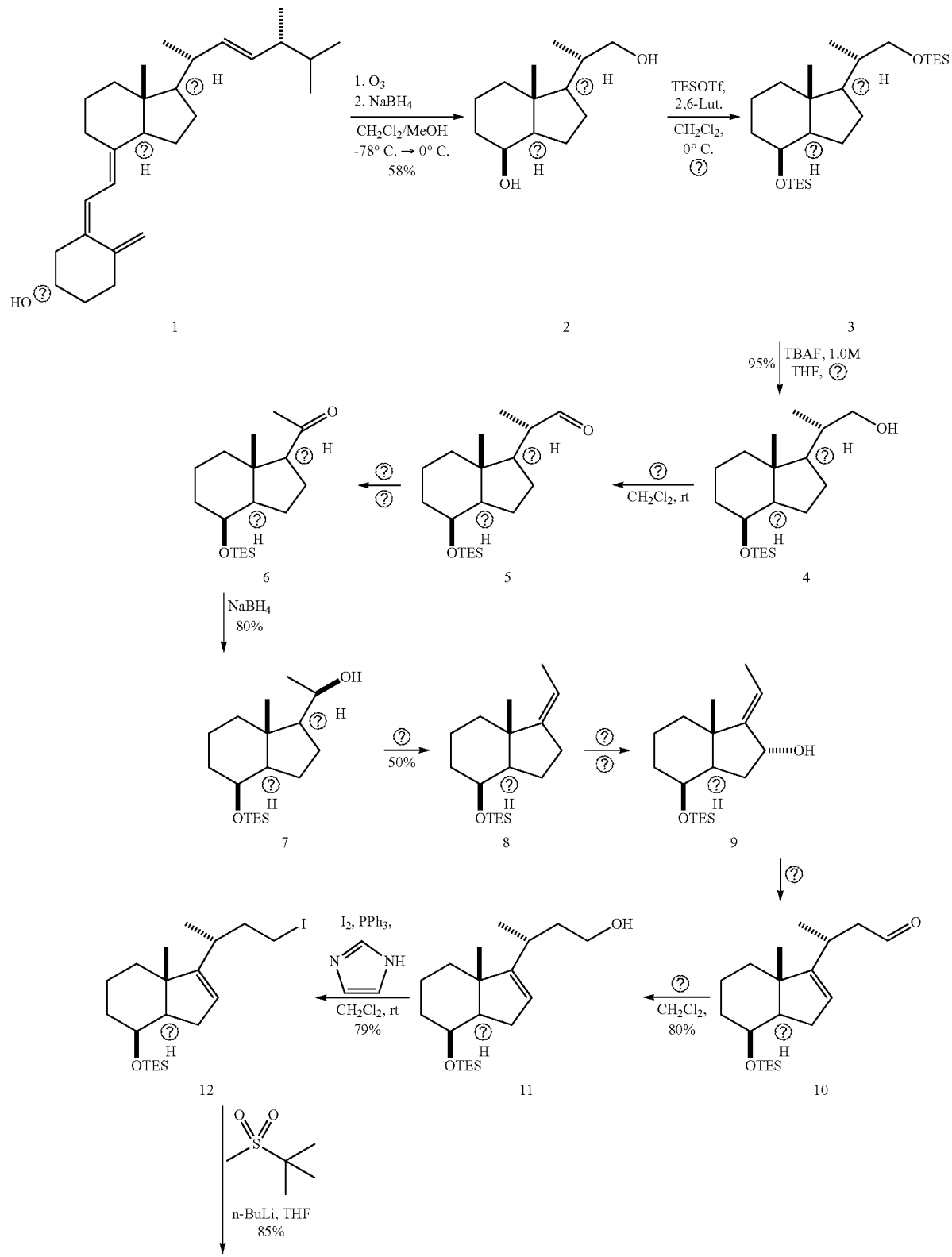

-continued

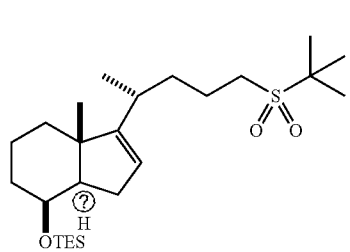
13

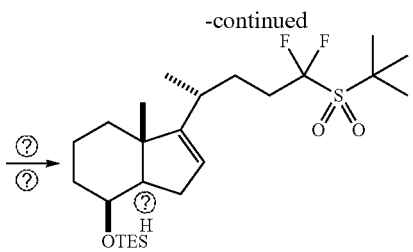
14

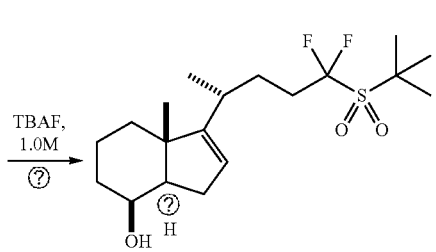
TBAF, 1.0M
15

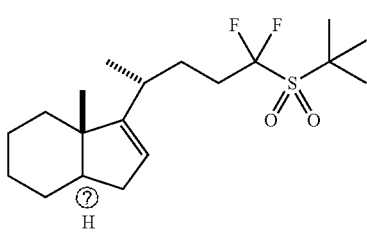
Iaii

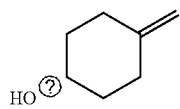

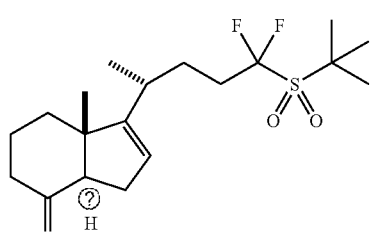
16

(?) indicates text missing or illegible when filed

The compound numbers in the scheme shown above (i.e., 1, 2, 3, 4, 5, 6, 7, 8, 9, 10, 11, 12, 13, 14, 15, 16, and 17) are relevant only in the context of this Example 1.

Synthesis of Compound 2

Compound 2 was synthesized according to the procedure in Grzywacz et al. Archives of *Biochemistry and Biophysics*, 2007, 460, 274-284. A flame dried, three-neck 1000 mL round bottom flask was connected to an ozonolyzer at the first opening, and to a gas adaptor at the third opening with a tygon tube that was dipped in 1000 mL of a saturated solution of sodium bisulfite. The central opening of the round bottom flask was plugged with a glass stopper. The flask was charged with argon gas, compound 1 (5.00 g, 12.61 mmol), NaHCO$_3$ (0.08 g, 0.88 mmol, 0.07 equiv.), CH$_2$Cl$_2$ (210 mL) and MeOH (60 mL). The mixture was stirred at −78° C. for 10 min while the ozonolyzer purged the system with O$_2$. The flow of O$_3$ was initiated and the solution continued to stir at −78° C. for 6 hours. During this time, the color of the solution turned from yellow to dark blue, and TLC analysis determined that most of the starting material was consumed. The clear reaction solution was then purged with O$_2$ for 1 hour and the solution turned to a light blue color. The flask was then transferred to a 0° C. ice water bath and NaBH$_4$ (4.30 g, 113.45 mmol, 9.00 equiv.) was added in five, separate portions to minimize the exothermic effects. The reaction mixture was then stirred at 0° C. for 5 hours. TLC analysis determined that the intermediate material had been consumed. The clear reaction solution was then was acidified to a pH of 6 with 30% acetic acid in methanol. The crude material was concentrated under reduced pressure, taken up in CH$_2$Cl$_2$ (300 mL) and washed with saturated NaHCO$_3$ (4×200 mL), brine (2×200 mL) and water (2×200 mL). The crude material was dried over MgSO$_4$ and the solvent was reduced under vacuum. Purification was performed using silica gel column with a solvent system of ethyl acetate/petroleum ether (1:1) to yield pure product 2 (45% yield, 1.20 g, 5.68 mmol). $^1$H NMR (400 MHz, CDCl$_3$) δ 4.08 ($^1$H, d, J=2.0 Hz), 3.63 (1H, dd, J=10.5, 3.1 Hz), 3.38 (1H, dd, J=10.5, 6.8 Hz), 1.99 (1H, br d, J=13.2 Hz), 1.03 (3H, d, J=6.6 Hz), 0.96 (3H,); $^{13}$C NMR (100 MHz) δ 69.16, 67.74, 52.90, 52.33, 41.83, 40.19, 38.20, 33.53, 26.62, 22.54, 17.36, 16.59, 13.54.

Synthesis of Compound 3

A flame dried, 50 mL round bottom flask was charged with argon gas, compound 2 (0.21 g, 0.96 mmol, 1.00 equiv.) and anhydrous CH$_2$Cl$_2$ (25 mL) The mixture was allowed to stir at 0° C. for 5 min. Then, 2,6-lutidine (0.44 mL, 3.72 mmol, 4.10 equiv.) was added dropwise to the stirring solution. The mixture stirred at 0° C. for 10 min. Neat triethylsilyl trifluoromethanesulfonate (TESOTf, 0.45 mL, 1.99 mmol, 2.20 equiv.) was added dropwise to this solution. The solution was stirred for 1 hour while warming to room temperature. TLC analysis determined that the starting material had been completely consumed. The clear reaction solution was quenched with ammonium chloride (10 mL). The reaction mixture was taken up into CH$_2$Cl$_2$ (20 mL), washed with ice cold brine (2×10 mL), water (2×10 mL), dried over MgSO$_4$, and the solvent was reduced under vacuum. Purification was performed using a silica gel column with a solvent system of ethyl acetate/petroleum ether (1:9) to yield pure product 3 (99% yield, 0.42 g, 0.95 mmol). This pure product was carried on to the next step with out spectroscopic analysis.

Synthesis of Compound 4

Compound 4 was synthesized according to the procedure in U.S. Patent Application No. US/2007/238702. A flame dried, 50 mL single neck round bottom flask was charged with argon gas, compound 3 (0.367 g, 0.84 mmol, 1.00 equiv.) and anhydrous THF (15 mL). The mixture was stirred at −30° C. and tetrabutylammonium fluoride (TBAF, 0.85 mL, 0.84 mmol, 1.00 equiv.) was added dropwise via syringe to the stirring solution. The mixture was stirred at −30° C. for 1 hour and then at −10° C. for 3 hours. TLC analysis determined that almost complete consumption of starting material had occurred. The clear reaction solution was quenched with ammonium chloride (10 mL). The reaction mixture was taken up in $CH_2Cl_2$ (20 mL), washed with brine (2×10 mL), water (2×10 mL), dried over $MgSO_4$, and the solvent was reduced under vacuum. Purification was performed using a silica gel column with a solvent system of ethyl acetate/petroleum ether (3:7) to yield pure product 4 as an clear oil in (90% yield, 0.25 g, 0.76 mmol). $^1H$ NMR (400 MHz, $CDCl_3$) δ 4.07 (1H, d, J=2.3 Hz), 3.66 (1H, dd, J=10.5, 3.2, Hz), 3.39 (1H, dd, J=10.5, 6.8 Hz, 22-H), 1.98 (1H, dm, J=12.7 Hz), 1.05 (3H, d, J=6.6 Hz), 0.98 (9H, t, J=7.9 Hz), 0.95 (3H, s), 0.58 (6H, q, J=7.9 Hz); $^{13}C$ NMR (125 MHz) δ 69.2, 67.9, 53.1, 52.8, 42.1, 40.6, 38.2, 34.6, 26.8, 23.0, 17.6, 16.6, 13.5, 6.9, 4.9.

Synthesis of Compound 5

Pyridinium chlorochromate (6.00 g, 27.9 mmol) and oven-dried Celite (6.00 g) with dichloromethane (90 mL) was added to a 250 mL round bottom flask and stirred for 5 min. Compound 4 (4.55 g, 13.9 mmol) was dissolved in dichloromethane (10 mL) and cannulated into the reaction flask. The contents of the flask were stirred for 4.5 hour. An additional 0.50 g of pyridinium chlorochromate (2.3 mmol) and Celite (0.5 g) were added. The reaction mixture was stirred for 2 hours, diluted with diethyl ether (50 mL), and filtered through a pad of Celite. The resulting organic layer was dried over $MgSO_4$ and concentrated in vacuo. Purification by gradient column chromatography (0 to 5% ethyl acetate/hexanes) afforded 4.96 g of the crude compound 5, which was used directly in the next step without farther analysis.

Synthesis of Compound 6

A 250 mL round bottom flask was charged with compound 5 (4.96 g) and dissolved in anhydrous benzene (70 mL). The contents of the flask were stirred and morpholine (1.60 g, 18.3 mmol) and p-toluenesulfonic acid (0.145 g, 0.8 mmol) were added. The apparatus was equipped with a Dean-Stark condenser and refluxed for 12 hours. Excess benzene was removed to yield the intermediate enamine, which was diluted in dichloromethane (150 mL) and added to a 3 neck 500 mL round bottom flask. A small amount of methylene blue was added to the flask and it was cooled to −78° C. The flask was exposed to hv while $O_2$ was bubbled through it for 6 hours. The solution was filtered through a pad of silica to remove the methylene blue, washed with dichloromethane (2×50 mL), washed with ethyl acetate (1×5 0 mL), and concentrated in vacuo. Purification by gradient column chromatography (0 to 10% ether/hexanes) afforded 1.91 g of compound 6 (6.16 mmol, 49%) as a colorless oil.

Synthesis of Compound 7

Compound 6 (1.91 g, 6.16 mmol) was dissolved in methanol (150 mL) and added to a 250 mL round bottom flask. The solution was cooled to −5° C. and sodium borohydride (1.17 g, 30.8 mmol) was added in two portions over 10 minutes. The reaction was quenched with 1N HCl (100 mL), extracted with diethyl ether (3×50 mL), dried over $MgSO_4$, and concentrated in vacuo. Purification by gradient column chromatography (0 to 5% ethyl acetate/hexanes) afforded compound 7 (1.54 g, 4.93 mmol, 80% yield) as a colorless oil.

Synthesis of Compound 8

Compound 7 (0.99 g, 3.18 mmol) was dissolved in 25 mL of freshly distilled pyridine and added to a 50 mL round bottom flask. The resulting solution was cooled to 0° C. and phosphoryl chloride (5.00 mL, 49.4 mmol) was added dropwise over 10 minutes. The reaction was warmed to room temperature and stirred for 16 hours. The reaction cooled to 0° C., was quenched with ice water, extracted with ethyl acetate (3×25 mL), dried over $MgSO_4$, and concentrated in vacuo. Purification by column chromatography (100% hexanes) afforded compound 8 (0.45 g, 1.53 mmol, 48% yield) as a colorless oil.

Synthesis of Compound 9

A mixture of tert-butylhydroperoxide (0.306 mL, 3.06 mmol), selenium dioxide (42.5 mg, 0.38 mmol), and dichloromethane (8 mL) was added to a 25 mL round bottom flask and allowed to stir for 1 h. The reaction was cooled to 0° C. and compound 8 (0.45 g, 1.53 mmol) was cannulated into the reaction flask with dichloromethane (12 mL). The reaction was stirred for 16 hours before slowly returning to room temperature. The resulting solution was concentrated in vacuo and dissolved in methanol (5 mL). The mixture was then cooled to 0° C. and sodium borohydride (58 mg, 1.53 mmol) was slowly added. The reaction stirred for an additional hour, was quenched with water (5 mL), sequentially extracted with dichloromethane (1×10 mL) and ethyl acetate (2×10 mL), dried over $MgSO_4$, concentrated in vacuo, and purified by column chromatography (5% ethyl acetate/ hexanes). Compound 9 (0.39 g, 1.27 mmol, 82% yield) was obtained as a colorless oil.

Synthesis of Compound 10

Compound 9 (0.39 g, 1.27 mmol) was dissolved in ethyl vinyl ether (8 mL) and added to a pressure tube. Mercury acetate (0.32 g, 1.01 mmol) was added to the tube and it was tightly sealed. The reaction was heated to 120° C., stirred overnight, concentrated in vacuo, and purified by column chromatography (10% ethyl acetate/hexanes) to yield compound 10 (0.29 g, 0.86 mmol, 68% yield) as a colorless oil.

Synthesis of Compound 11

Compound 10 (0.29 g, 0.86 mmol) was added to a 50 mL round bottom flask, dissolved in HPLC grade hexanes (15 mL), and cooled to 0° C. Diisobutylaluminum hydride (1.0 M) in dichloromethane (2.58 mL, 2.58 mmol) was added dropwise over 10 minutes and then stirred for 45 minutes. The reaction was diluted with diethyl ether (15 mL) and quenched with 10% HCl (20 mL). The mixture was extracted with ethyl acetate (3×20 mL) and sequentially washed with a saturated solution of sodium bicarbonate (15 mL) and then brine (15 mL). The combined organic extracts were dried over sodium sulfate, concentrated in vacuo, and purified by column chromatography (10% ethyl acetate/ hexanes) to afford compound 11 (227 mg, 0.67 mg, 78% yield) as a colorless oil.

Synthesis of Compound 12

Imidazole (74 mg, 1.09 mmol) and triphenylphosphine ($PPh_3$, 125 mg, 0.48 mmol) were added to a 25 mL round bottom flask and dissolved in dichloromethane (8 mL). The resulting solution was cooled to 0° C. and a solution of $I_2$ was (135 mg, 0.53 mmol) in dichloromethane (6 mL) was added to the flask. The solution stirred for 20 minutes, compound 11 was cannulated into the reaction flask, and the flask was warmed to room temperature. Stirring continued overnight. The reaction was then extracted with dichloromethane (1×10 mL), with ethyl acetate (2×15 mL) and sequentially washed with $H_2O$ (10 mL) and then brine (10 mL). The organic extracts were combined, dried over $MgSO_4$, concentrated in vacuo, and purified by column chromatography (100% hexanes) to yield compound 12 (47 mg, 0.10 mmol, 79% yield) as a colorless oil.

Synthesis of Compound 13

A solution of methyl t-butyl sulfone (0.12 g, 0.87 mmol) in anhydrous THF (3.0 mL) was cooled to −78° C. To the above solution n-butyllithium (n-BuLi) in hexanes (1.4 M, 0.61 mL) was added dropwise and stirred for 30 minutes. Compound 12 (78 mg, 0.17 mmol) in 1.0 mL of anhydrous THF was added to a separate flask. The solution containing compound 12 was added to the solution containing n-butyllithium via cannula over 2 minutes. The reaction mixture was stirred at −78° C. for an additional 30 minutes and then allowed to warm to room temperature. After 4 hours, TLC analysis indicated that starting material was consumed. The reaction was quenched with buffer (pH 7), extracted with ethyl acetate, washed with brine, dried over anhydrous $MgSO_4$, concentrated in vacuo, and then purified by silica gel column chromatography (20% ethyl acetate/petroleum ether) to afford compound 13 (0.06 g, 0.14 mmol, 85% yield) as a colorless oil.

Synthesis of Compound 14

Compound 13 (0.06 g, 0.12 mmol) was dissolved in THF (2.0 mL). A solution of n-butyllithium in hexanes (0.18 mL, 0.29 mmol) was added to the solution at −78° C. The solution was stirred for 45 minutes at −78° C. N-Fluorobenzenesulfonamide (NFSI, 0.08 g, 0.24 mmol) in THF (1.5 mL) was added to a separate, dry flask. The NFSI solution was added to the n-butyllithium solution reaction via cannula over 2 minutes. The reaction mixture was stirred while warming to room temperature overnight. TLC analysis indicated that all starting material was consumed. The reaction was quenched with buffer (pH 7), extracted with ethyl acetate, washed with brine, dried over anhydrous $MgSO_4$, concentrated in vacuo, and then purified by silica gel column chromatography (20% ethyl acetate/petroleum ether) to afford a mixture of both mono- and difluorinated sulfones (0.05 g) as a white solid.

The mixture was redissolved in anhydrous THF (2.0 mL) and n-BuLi in hexanes (0.18 mL 0.29 mmol) at −78° C. was added dropwise. N-Fluorobenzenesulfonamide (NFSI) (0.08 g, 0.24 mmol) in THF (1.5 mL) was added to a separate, dry flask. The NFSI solution was added to the n-butyllithium reaction via cannula over 2 minutes. The reaction mixture was stirred while warming to room temperature overnight. TLC analysis indicated that all starting material was consumed, and the reaction was quenched with buffer (pH 7), extracted with ethyl acetate, washed with brine, dried over anhydrous $MgSO_4$, concentrated in vacuo, and then purified by silica gel column chromatography (10% ethyl acetate/petroleum ether) to give compound 14 (0.04 g, 0.07 mmol, 58% yield) as a colorless oil.

Synthesis of Compound 15

A flame dried 50 mL single neck round bottom flask was charged with argon gas, compound 14 (0.04 g, 0.07 mmol) and anhydrous THE (3.0 mL) The mixture was stirred at room temperature. TBAF (0.22 mL, 0.22 mmol) was added dropwise via syringe to the stirring solution. The mixture continued to stir at room temperature for 1 hour. TLC analysis indicated that complete consumption of starting material had occurred. The clear reaction solution was quenched with ammonium chloride (5.0 mL). The reaction mixture was then taken up into $CH_2Cl_2$ (20 mL), washed with brine (2×10 mL), and water (2×10 mL). The crude material was dried over $MgSO_4$ and reduced under vacuum.

Purification was performed using silica gel (20% ethyl acetate/petroleum ether) to give compound 15 as an clear oil (0.03 g, 0.10 mmol, 68% yield).

Synthesis of Compound 16

A flame dried 25 mL flask was charged with compound 15 (0.03 g, 0.10 mmol), anhydrous $CH_2Cl_2$ (5.0 mL), oven dried celite, and pyridinium dichromate (0.05 g, 0.12 mmol). The reaction was stirred for 13 hours at room temperature. TLC analysis indicated that complete consumption of starting material had occurred. The resulting red reaction solution was quenched with water (5.0 mL) and the reaction mixture was taken up into $CH_2Cl_2$ (20 mL), washed with brine (2×10 mL), and water (2×10 mL). The crude material was dried over $MgSO_4$ and reduced under vacuum. Purification was performed using silica gel column chromatography (20% ethyl acetate/petroleum ether) to give pure compound 16 as an clear oil (0.03 g, 0.10 mmol, 69% yield).

Synthesis of Compound Iaii

The synthesis of enantiomerically pure 1-nor A-ring phosphine oxide (compound 17) was conducted using a procedure by Wilson, S. R. et. al. in *Bioorganic Chemistry*, 1995, 23, 22-32.

Compounds 16 and 17 were azeotropically dried with anhydrous benzene (5×10 mL) on a rotary evaporator at 40° C. for 30 minutes at a time and then held under vacuum (about 0.1 mmHg) for at least 96 hours prior to use. A flame-dried 10-mL recovery flask equipped with a magnetic stir bar and a septum along with an argon balloon was charged with phosphine oxide 17 (0.06 g, 0.11 mmol, 2.15 equiv.), which was dissolved in 1.0 mL of freshly distilled THF to give a 0.1 M solution. The flask was cooled to −78° C. in a 2-propanol/dry ice bath. n-Butyllithium (75 μL, 0.21 mmol, 1.6 M solution in hexanes) was added dropwise to this solution over several minutes, during which time a deep red color developed and persisted. This mixture was stirred at −78° C. for an additional 10 minutes. A flame-dried 10-mL recovery flask equipped with a magnetic stir bar, a septum, and an argon balloon was charged with compound 16 (0.02 g, 0.05 mmol, 1.00 equiv.) dissolved in 1 mL of freshly distilled THF and cooled to −78° C. in a 2-propanol/ dry ice bath. A solution of compound 17 was transferred dropwise into the flask containing the phosphine oxide anion at −78° C. via cannula over several minutes. After the addition was complete, a deep red color persisted and the mixture was allowed to stir at −78° C. for about 8 hours. During this time, the color of the solution was monitored. Upon observation of a light yellow color, the reaction was quenched at −78° C. by addition of 5 mL of buffer (pH 7) and warmed to room temperature. The mixture was then rinsed into a separatory funnel with ethyl acetate and extracted with ethyl acetate (3×25 mL). The extracts were combined, washed with water (1×25 mL), washed with brine solution (1×25 mL), dried over $Na_2SO_4$, and filtered. The filtrate was concentrated in vacuo to give crude product. The product was purified by column chromatography using an eluent of 50% ethyl acetate in hexanes in the presence of 1% triethylamine to afford a coupled product. This coupled product (0.02 g, 0.04 mmol, 91% yield) was charged into a 5 mL argon-purged polypropylene vial equipped with a magnetic stir bar and then dissolved in 2.5 mL of acetonitrile to result in a 0.02 M solution. This solution was stirred and HF was added (2.50 mmol, 8.6 mL) via syringe at room temperature. The mixture was stirred at room temperature in the dark for 1 hour. TLC showed the completion of the reaction. This reaction mixture was diluted with ether (25 mL), and a saturated solution of $NaHCO_3$ was added until the liberation of carbon dioxide ceased. The reaction mixture was then rinsed into a separatory funnel with ethyl acetate and extracted with ethyl acetate (5×25 mL). The extracts were combined, washed with water (1×25 mL), washed with brine solution (1×25 mL), dried over $Na_2SO_4$, and filtered. The filtrate was concentrated in vacuo to give the crude product. The product was purified by column flash chromatography using 99% ethyl acetate in the presence of 1% triethylamine as the eluent to afford (0.01 g, 0.03 mmol, 70% yield) of Iaii as a single diastereomer. $[\alpha]_D^{25.1}=+37.5$ (c=0.10, MeOH); IR (neat) 3390, 3041, 2933, 1650, 1627, 1470, 1401, 1367, 1321, 1246, 1179, 1131, 981, 891 cm$^{-1}$; $^{19}$F NMR (Acetone d$_6$, 376 MHz) δ −98.2; $^1$H NMR (Acetone d$_6$, 400 MHz) δ 6.15 (d, J=11.0 Hz, 1H), 6.05 (d, J=11 Hz, 2H), 5.29 (s, 1H), 4.92 (d, J=1.2 Hz, 1H), 4.64, (s, 1H), 3.80-3.50 (m, 2H), 2.80-2.60 (m, 2H), 2.50-2.35 (m, 1H), 2.34-2.22 (m, 2H), 2.20-2.05 (m, 2H), 2.03-1.88 (m, 3H), 1.85-1.50 (m, 4H), 1.50-1.40 (m, 3H), 1.40-1.30 (m, 9H), 1.00-0.91 (m, 6H), 0.58 (s, 3H); $^{13}$C (Acetone d$_6$, 125 MHz) δ 159.5, 157.5, 147.0, 140.9, 137.7, 133.2, 122.2, 120.1, 118.8, 112.4, 69.6, 63.7, 59.2, 50.7, 48.7, 47.2, 36.1, 35.8, 33.2, 33.1, 32.4, 31.2, 24.29, 24.27, 22.1, 17.3; UV (MeOH)λ$_{max}$ 273 nm (ε 25,886).

Example 2: Synthesis of 4-Methylene-3-(2-{7α-methyl-1-[1-methyl-4-(2-methyl-propane-2-sulfonyl)-but-3-enyl]-3,3α,5,6,7,7a-hexahydro-inden-4-ylidene}-ethylidene)-cyclohexanol (Ibii)

Small-Scale Synthesis

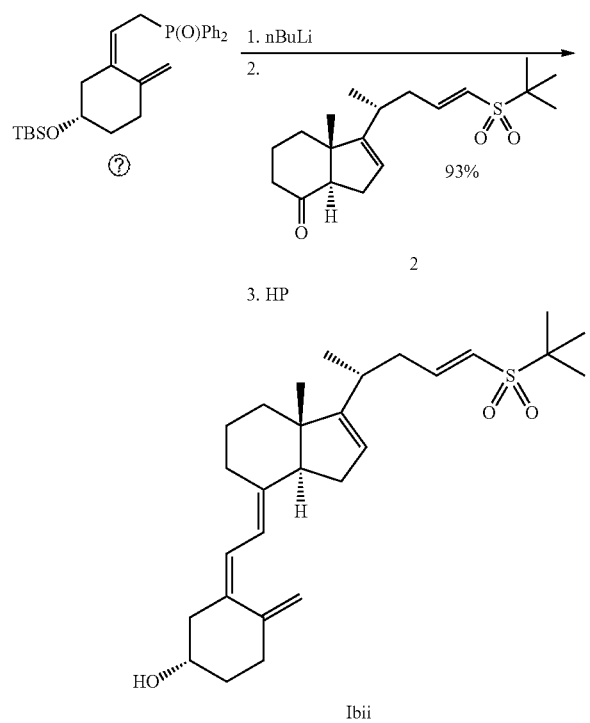

Ⓟ indicates text missing or illegible when filed

The compound numbers in the scheme shown (i.e., 1 and 2) are relevant only in the context of this Example 2.

Enantiomerically pure 1-deoxy-phosphine oxide 1 was prepared according to Wilson, et al. *Bioorganic Chemistry* 1995, 23, 22-32) and compound 2 was prepared according to Posner et al. *J. Med. Chem.* 1999, 42, 3425-3435). These compounds were separately azeotropically dried with anhydrous benzene (3×4 mL) on a rotary evaporator and held under vacuum for 120 hours prior to use.

Compound 1 (60 mg, 0.13 mmol) was added to a flame dried 10 mL pear shaped flask equipped with a magnetic stir bar and an argon balloon, and dissolved in 1 mL of freshly distilled tetrahydrofuran (THF). The solution was cooled to −78° C. and n-butyllithium (83 μL, 0.13 mmol, 1.6 M in hexanes) was added dropwise over 5 minutes during which time a deep red color developed and persisted. This mixture was stirred at −78° C. for an additional 25 minutes. A flame-dried, 10 mL round bottom flask containing compound 2 (15 mg, 0.044 mmol) dissolved in 1 mL of THF was cooled to −78° C. This solution was transferred dropwise via cannula into the flask containing the compound 1 at −78° C. over 5 minutes. After the addition was complete, the deep red color persisted and the mixture was stirred −78° C. for an additional 4 hours. After the reaction developed a light yellow color, the reaction was quenched with 3 mL of buffer (pH 7) and warmed to room temperature. The mixture was extracted with ethyl acetate (1×5 mL) and methylene chloride (2×5 mL). The organic extracts were combined, dried over MgSO$_4$, and filtered. The filtrate was concentrated in vacuo to give crude product. The product was purified by column chromatography (20% ethyl acetate/hexanes with 1% triethylamine) to affording the protected analog (24 mg, 0.022 mmol, 93% yield). The protected analog was dissolved in acetonitrile (2 mL) and hydrofluoric acid (8.0 mL, 2.2 mmol, 49% aqueous solution) was added to the solution. The reaction was stirred for 4 hours, quenched with a saturated aqueous solution of sodium bicarbonate (10 mL), and stirred until gas ceased to evolve. The aqueous layer was extracted with ethyl acetate (3×5 mL), dried over MgSO$_4$, and filtered. The filtrate was concentrated in vacu, and the crude product was purified by column chromatography (30% ethyl acetate/hexanes with 1% triethylamine) to afford compound Ibii (13 mg, 0.030 mmol, 72% yield) as a colorless oil. $[\alpha]_D^{23}=+19.5$ (c=0.1, CHCl$_3$), IR (thin film) 3500, 2930, 2850, 1739, 1471, 1455, 1290, 1113, 1048, 1006, 969, 907, 890, 730, 690, 618 cm$^{-1}$; $^1$H NMR (400 MHz, CDCl$_3$) δ 6.84-6.77 (m, 1H), 6.25-6.21 (m, 2H), 6.10 (d, J=11 Hz, 1H), 5.35 (s, 1H), 5.05 (s, 1H), 4.82 (s, 1H), 3.96 (s, 1H), 2.84-2.80 (m, 1H), 2.59-1.49 (m, 18H), 1.34 (s, 9H), 1.09 (d, 3H J=6 Hz), 0.69 (s, 3H); $^{13}$C NMR (100 MHz, CDCl$_3$) δ 157.9, 150.2, 145.0, 140.9, 135.5, 124.5, 122.2, 122.1, 117.7, 112.5, 69.1, 58.3, 58.2, 50.0, 45.9, 38.7, 35.4, 35.1, 32.0, 31.8, 29.4, 28.6, 23.5, 23.3, 21.3, 17.1; UV (MeOH) λ$_{max}$ 266 nm (ε 13210).

Large-Scale Synthesis

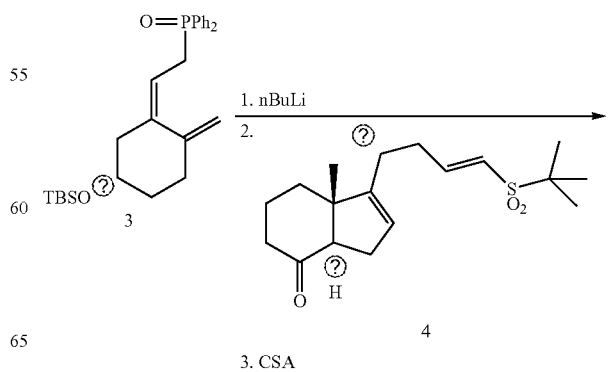

-continued

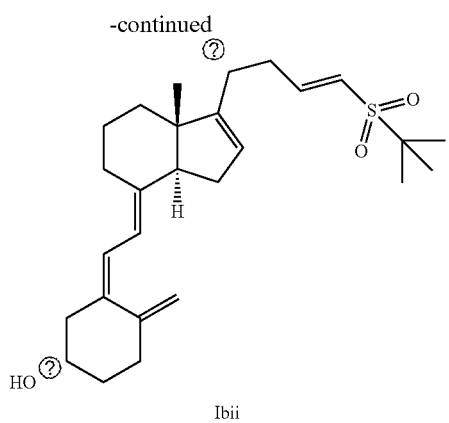

Ibii

⟨?⟩ indicates text missing or illegible when filed

The compound numbers in the scheme shown above (i.e., 3 and 4) are relevant only in the context of this Example 2.

A 250-mL, flame dried, three-neck round bottom flask was charged with compound 3 (4.20 g, 9.27 mmol) in THF. The flask was connected to a continuous flow of argon gas and placed in a −78° C. acetone/dry ice bath. N-Butyllithium (4.08 mL, 10.20 mmol, 2.5 M in hexane) was added to the flask dropwise via a syringe and the solution was stirred for 45 minutes at −78° C. In another flask, ketone 4, (6.28 g, 18.55 mmol, 1:2 cis-trans mix at side chain olefin) was dissolved in anhydrous THF (50 mL) and slowly transferred via cannula to the reaction flask under argon pressure. The resulting mixture was stirred for another 45 minutes at −78° C. TLC (in methylene chloride) indicated that the starting materials had been completely consumed. A saturated solution of ammonium chloride was added to the reaction flask and extraction was performed with 200 mL of ethyl acetate. The organic layer was washed with brine, water, dried over anhydrous $Na_2SO_4$, filtered, and concentrated. The crude product was purified by gradient column chromatography using 0 to 100% methylene chloride in hexane. The pure trans olefin fractions were concentrated to yield the protected product (65%) as a white solid.

The protected product (2.3 g, 4.0 mmol) was dissolved in $CH_2Cl_2$/MeOH (1:1; 100 mL) and camphorsulfonic acid (CSA, 1.39 g, 6.02 mmol) was added. The reaction occurred overnight under an argon atmosphere in a 250 mL round bottom flask. TLC (30% ethyl acetate/hexanes) of the reaction mixture indicated the complete disappearance of the starting material. A saturated solution of sodium bicarbonate was slowly added to the flask and the solution was concentrated under vacuum. The crude mass was dissolved in ethyl acetate, washed with water, and washed with brine. The organic layer was dried over anhydrous sodium sulfate, evaporated under vacuum, purified by gradient silica gel column chromatography (0 to 50% ethyl acetate in hexanes), and crystallized from diethyl ether/hexanes to provide compound Ibii (89% yield) as a white solid. Compound Ibii was characterized by $^1$H-NMR and mass spectrometry. The purity of compound Ibii was measured by HPLC as 99.56%. $^1$H NMR (400 MHz, $CDCl_3$) δ 6.84-6.77 (m, 1H), 6.25-6.21 (m, 2H), 6.10 (d, J=11 Hz, 1H), 5.35 (s, 1H), 5.05 (s, 1H), 4.82 (s, 1H), 3.96 (s, 1H), 2.84-2.80 (m, 1H), 2.59-1.49 (m, 18H), 1.34 (s, 9H), 1.09 (d, 3H J=6 Hz), 0.69 (s, 3H); MS (m/z): 481.33 (M+$Na^+$), 458.33 (M+$H^+$), 441.33 (M+$H^+$−$H_2O$). UV (MeOH); $\lambda_{max}$ 265 nm (ε 20,183). Optical rotation: +15.76 (C=0.52, $CHCl_3$).

Example 3: Synthesis of 3-{2-[1-(3-Benzenesulfonyl-1-methyl-propyl)-7α-methyl-octahydro-inden-4-ylidene]-ethylidene}-4-methylene-cyclohexanol (Idii)

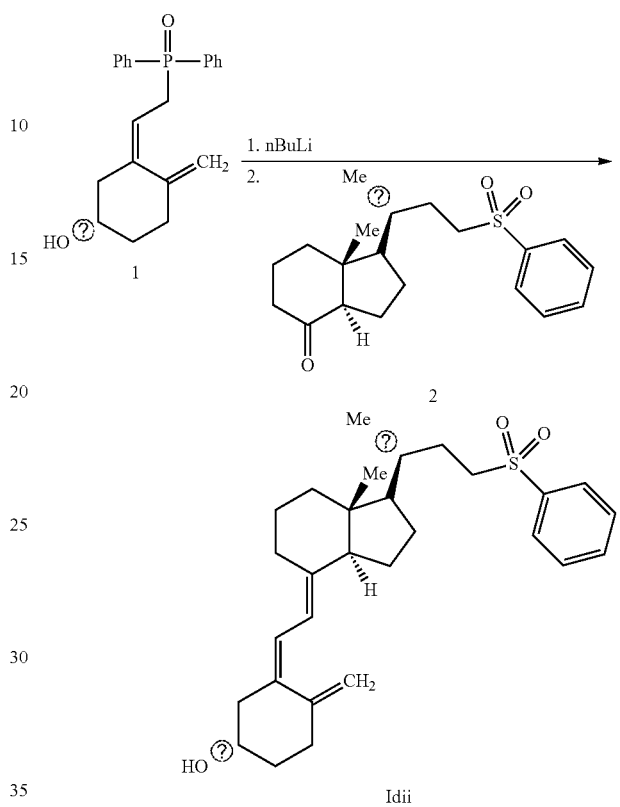

Idii

The compound numbers in the scheme shown above (i.e., 1 and 2) are relevant only in the context of this Example 3.

Enantiomerically pure 1-deoxy-phosphine oxide 1 was prepared according to Wilson, et al. *Bioorganic Chemistry* 1995, 23, 22-32) and compound 2 was prepared according to Posner et. al, *J. Steroid Biochem. Mol. Biol.*, 2005, 89-90, 5-12. These compounds were separately azeotropically dried with anhydrous benzene (3×4 mL) on a rotary evaporator and held under vacuum (less than 0.5 mmHg) for 96 hours prior to use.

Phosphine oxide 1 (63 mg, 0.14 mmol) was added to a flame dried 10 mL round bottom flask equipped with a magnetic stir bar and an argon balloon, and dissolved in 1 mL of freshly dried tetrahydrofuran (THF), distilled from sodium-benzophenone, and cooled −78° C. A solution of n-butyllithium (88 μL, 0.14 mmol, 1.6 M in THF) was added dropwise over 5 minutes to the solution in the flask. A deep red color developed and persisted and the resulting solution stirred at −78° C. for an additional 25 minutes.

An oven-dried 10 mL pear bottom flask containing compound 2 (19 mg, 0.054 mmol) was dissolved in 1 mL of freshly distilled THF and cooled to −78° C. This solution was transferred dropwise into the flask containing the compound 1 at −78° C. via cannula over 5 minutes. After the addition was complete, the solution was stirred for 3 hours at −78° C. When a light yellow color was observed, the reaction was quenched with 3 mL of SPECPURE buffer (pH 7) and allowed to warm to room temperature. The mixture was extracted with ethyl acetate (1×5 mL) and dichloromethane (2×5 mL). The organic extracts were combined, dried over $MgSO_4$, and filtered. The filtrate was concentrated in vacuo to give crude product that was purified by gradient column chromatography (100% hexanes to 15% ethyl acetate in hexanes with 1% triethylamine), affording the silylated analog (6 mg, 0.010 mmol, 18% yield). The silylated analog was dissolved in 1 mL of freshly distilled THF and n-Bu$_4$NF (25 μL, 0.025 mmol, 1.0 M in hexanes) was added to it. The solution was stirred for 16 hours and then the reaction was quenched with a saturated aqueous solution of sodium bicarbonate (7 mL). The aqueous layer was extracted with ethyl acetate (2×5 mL), dried over MgSO$_4$, and filtered. The filtrate was concentrated in vacuo, and the crude product was purified by silica gel column chromatography (25% ethyl acetate in hexanes with 1% triethylamine) to afford compound Idii (4, 2.4 mg, 0.005 mmol, 50% yield) as a colorless oil. $^1$H-NMR (400 MHz, CD$_6$CO) δ 8.09 (d, 2H), 7.90, (t, 1H), 7.82 (t, 2H), 6.37 (d, 1H), 6.19 (d, 2H), 5.18 (s, 1H), 4.89 (s, 1H), 3.88 (m, 1H), 3.35 (m, 2H), 2.68 (m, 1H), 2.57 (m, 1H), 2.35 (m, 1H), 2.09 (m, 4H), 1.94 (m, 3H), 1.80 (m, 2H), 1.71 (m, 4H), 1.66 (m, 5H), 1.46 (m, 3H), 1.11 (d, 1H), 1.07 (m, 1H), 0.77 (s, 1H), 0.67 (s, 3H), 0.28 (s, 1H). $^{13}$C NMR (100 MHz, CD$_6$CO) δ 137.6, 134.4, 130.1, 130.1, 128.9, 122.1, 118.9, 112.2, 69.6, 56.8, 56.4, 53.6, 47.2, 46.4, 41.1, 39.4, 36.6, 35.7, 35.1, 33.2, 27.9, 24.1, 22.8, 18.8, 12.2. UV (MeOH) λ$_{max}$ 264 nm (ε 10433), HRMS m/z (M$^+$) calculated 491.25904 for C$_{29}$H$_{40}$O$_3$SNa$^+$. found 491.25928.

Example 4: Synthesis of 7-{4-[2-(5-Hydroxy-2-methylene-cyclohexylidene)-ethylidene]-7α-methyl-3α,4,5,6,7,7a-hexahydro-3H-inden-1-yl}-2,2-dimethyl-octan-3-one 0-allyl-oxime (IIaii)

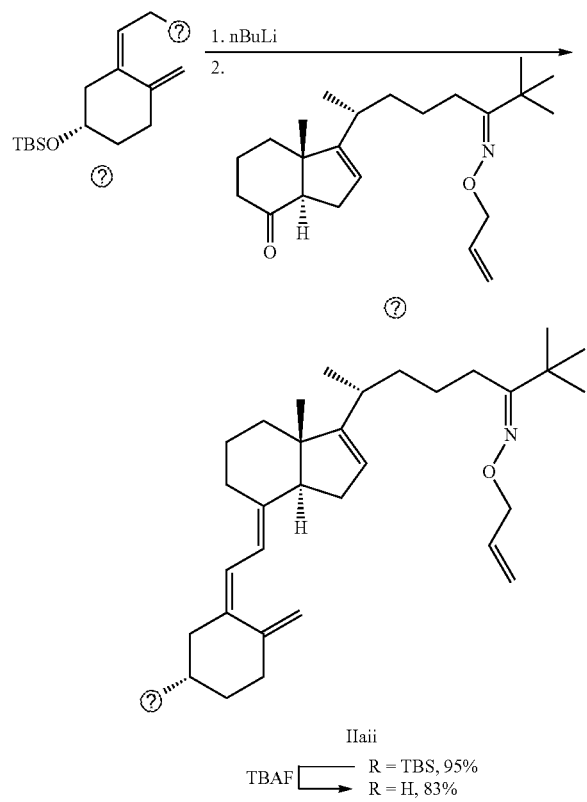

IIaii

TBAF ⎯→ R = TBS, 95%
         R = H, 83%

⊘ indicates text missing or illegible when filed

The compound numbers in the scheme shown above (e.g., 18 and 19) are relevant only in the context of this Example 4.

Enantiomerically pure 1-deoxy-phosphine oxide 19 was prepared according to Wilson, et al. *Bioorganic Chemistry* 1995, 23, 22-32). Compounds 19 and 18 were separately azeotropically dried with anhydrous benzene (3×3 mL) on a rotary evaporator and held under vacuum (less than 0.5 mmHg) for 120 hours prior to use.

A flame dried 10 mL round bottom flask equipped with a magnetic stir bar and an argon balloon was charged with phosphine oxide 19 (79 mg, 0.17 mmol), which was dissolved in 1 mL of tetrahydrofuran (THF) distilled from sodium-benzophenone. The reaction flask was cooled to −78° C. and nBuLi (109 μL, 0.17 mmol, 1.6 M in hexanes) was added dropwise over 5 minutes. A deep red color developed and persisted. This mixture was stirred −78° C. for an additional 25 minutes.

A flame-dried 10 mL round bottom flask containing compound 18 (17 mg, 0.047 mmol) was dissolved in 1 mL of freshly distilled THF and cooled to −78° C. This solution was transferred dropwise via cannula into the flask containing compound 19 at −78° C. over 5 minutes. After the addition was complete, a deep red color persisted and the mixture was stirred at −78° C. for 4 hours. Upon observation of a light yellow color, the reaction was quenched with 3 mL of SPECPURE buffer (pH 7) and allowed to warm to room temperature. The mixture was extracted with ethyl acetate (1×5 mL) and methylene chloride (2×5 mL). The organic extracts were combined, dried over MgSO$_4$ and filtered. The filtrate was concentrated in vacuo to give crude product that was purified by gradient column chromatography (100% hexanes to 50% ethyl acetate in hexanes with 1% NEt$_3$), affording the silylated analog (26.8 mg, 0.045 mmol, 95% yield). The silylated analog was dissolved in 3.0 mL of freshly distilled THF and TBAF was added (112 μL, 0.11 mmol, 1.0M in THF). The reaction was stirred for 16 hours and quenched with a saturated aqueous solution of sodium bicarbonate (10 mL). The aqueous layer was extracted with ethyl acetate (3×5 mL), dried over MgSO$_4$ and filtered. The filtrate was concentrated in vacuo, and the crude product was purified by column chromatography (20% ethyl acetate in hexanes with 1% NEt$_3$) to afford compound IIaii as a colorless oil (18 mg, 0.038 mmol, 83% yield). [α]$_D$26=+20.9 (c=0.535, CHCl$_3$), IR (thin film) 3327, 3012, 2955, 2929, 2866, 1456, 1437, 1393, 1365, 1290, 1258, 1180, 1162, 1045, 961, 106, 812, 718 cm$^{-1}$; $^1$H NMR (400 MHz, CDCl$_3$) δ 6.23 (d, J=9 Hz, 1H), 6.12 (d, J=11 Hz, 1H), 6.01-5.93 (m, 1H), 5.28 (s, 1H), 5.27-5.25 (dq, J=1.6, 17 Hz, 1H), 5.16-5.12 (dq, J=1.2, 11 Hz, 1H) 5.06 (s, 1H), 4.85 (s, 1H), 4.50-4.48 (dt, J=1.2, 6 Hz, 2H), 4.19 (m, 1H), 3.96 (m, 1H), 4.19 (m, 1H), 2.82 (m, 1H), 2.58 (m, 1H), 2.41-1.37 (m, 26H), 1.09 (s, 9H), 1.01 (d, J=7 Hz, 3H), 0.68 (s, 3H); $^{13}$C NMR (100 MHz, CDCl$_3$) δ 166.9, 159.7, 145.1, 141.7, 135.1, 134.9, 122.4, 120.3, 117.3, 116.5, 112.4, 74.1, 69.1, 58.4, 49.9, 45.8, 37.2, 7.1, 35.4, 35.1, 32.6, 31.8, 29.3, 28.7, 27.8, 26.6, 24.6, 23.6, 21.4, 16.9. UV (MeOH)λ$_{max}$ 265 nm (ε 11141).

Example 5: Synthesis of 3-{2-[1-(4-Benzenesulfoximine-1-methyl-butyl)-7α-methyl-octahydro-inden-4-ylidene]-ethylidene}-4-methylene-cyclohexanol (Icii)
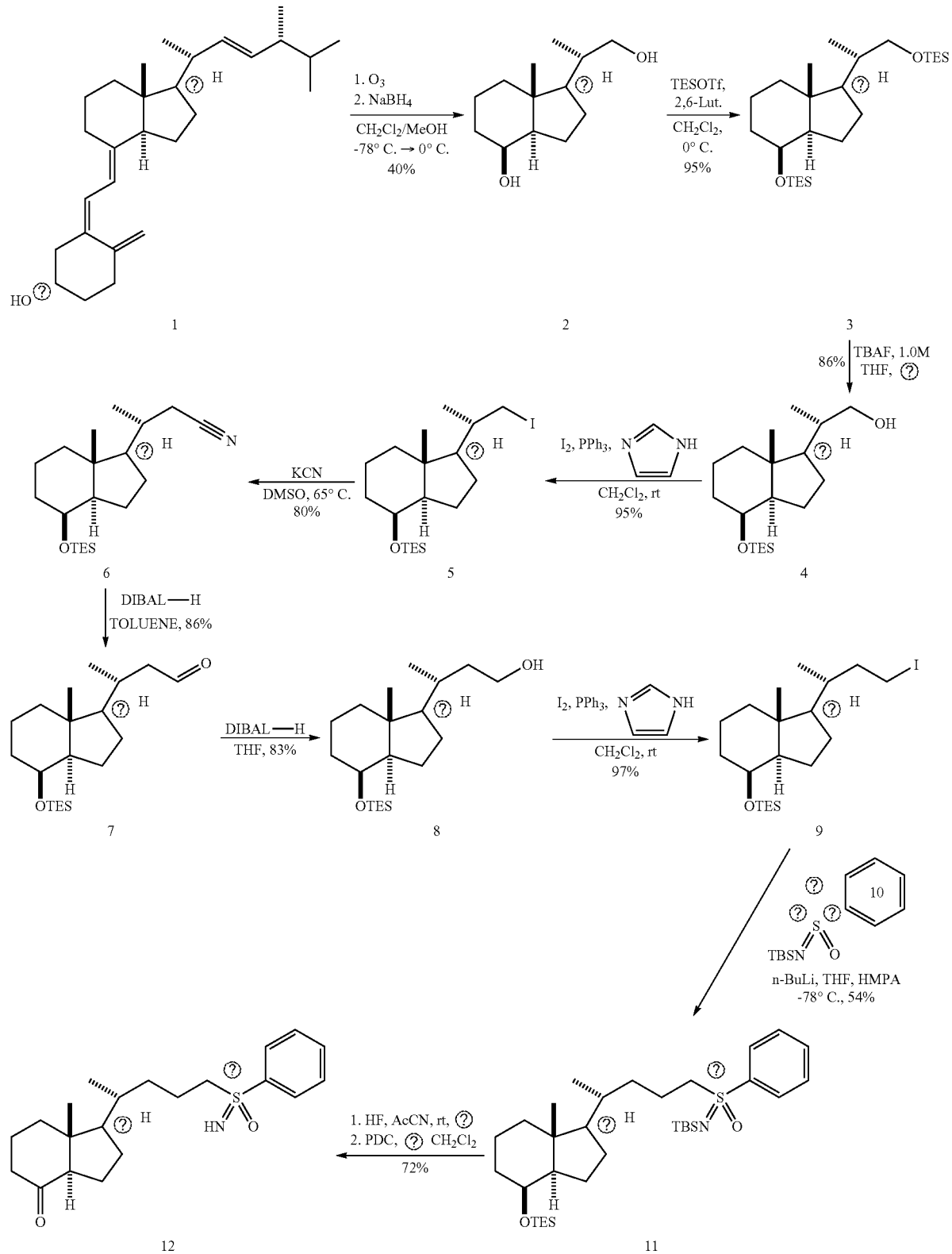

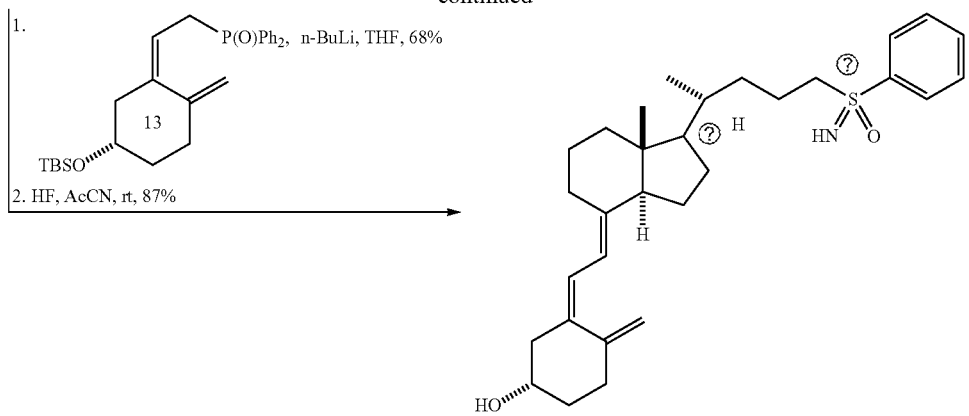

ⓘ indicates text missing or illegible when filed

The compound numbers in the scheme shown above (i.e., 1, 2, 3, 4, 5, 6, 7, 8, 9, 10, 11, 12, and 13) are relevant only in the context of this Example 5.

Synthesis of Compound 2

Compound 2 was synthesized according to the procedure in Grzywacz et al. *Archives of Biochemistry and Biophysics*, 2007, 460, 274-284. A flame dried three neck 1000 mL round bottom flask was connected at the first opening to an ozonolyzer and at the third opening to a gas adaptor with a tygon tube attached to it dipped in a saturated solution of sodium bisulfite (1000 mL). The central opening was plugged with a glass stopper and argon gas, compound 1 (5.00 g, 12.61 mmol), NaHCO$_3$ (0.08 g, 0.88 mmol, 0.07 equiv.), CH$_2$Cl$_2$ (210 mL) and MeOH (60 mL) was added to the flask. The mixture was stirred at −78° C. for 10 minutes while the ozonolyzer was purging the system with O$_2$. The flow of O$_3$ was then started and the solution was stirred at −78° C. for 6 hours. During this time, the color of the solution turned from yellow to dark blue. TLC analysis indicated that most of the starting material had been consumed. The clear reaction solution was purged with O$_2$ for 1 hour and the solution turned to a light blue color. The flask was then transferred to a 0° C. ice water bath and NaBH$_4$ (4.30 g, 113.45 mmol, 9.00 equiv.) was added in five portions to minimize the exothermic effects. The reaction mixture was then stirred at 0° C. for 5 hours. TLC analysis indicated that the intermediate material had been consumed. The clear reaction solution was acidified to pH 6 with 30% acetic acid/MeOH. The crude material was concentrated under reduced pressure, taken up in CH$_2$Cl$_2$ (300 mL) and washed with saturated NaHCO$_3$ (4×200 mL), brine (2×200 mL), and water (2×200 mL). The crude material was dried over MgSO$_4$ and reduced under vacuum. Purification was performed using silica gel chromatography with an eluent of ethyl acetate/petroleum ether (1:1) to give pure compound 2 (1.20 g, 5.68 mmol, 45% yield). $^1$H NMR (400 MHz, CDCl$_3$) δ 4.08 (1H, d, J=2.0 Hz), 3.63 (1H, dd, J=10.5, 3.1 Hz), 3.38 (1H, dd, J=10.5, 6.8 Hz), 1.99 (1H, br d, J=13.2 Hz), 1.03 (3H, d, J=6.6 Hz), 0.96 (3H,); $^{13}$C NMR (100 MHz) δ 69.16, 67.74, 52.90, 52.33, 41.83, 40.19, 38.20, 33.53, 26.62, 22.54, 17.36, 16.59, 13.54.

Synthesis of Compound 3

A flame dried 50 mL single neck round bottom flask was charged with argon gas, compound 2 (0.21 g, 0.96 mmol, 1.00 equiv.) and anhydrous methylene chloride (25 mL). The mixture was stirred at 0° C. for 5 minutes. Then, 2,6-lutidine (0.44 mL, 3.72 mmol, 4.10 equiv.) was added dropwise to the stirring solution. The mixture stirred at 0° C. for 10 min. Neat triethylsilyl trifluoromethanesulfonate (TESOTf, 0.45 mL, 1.99 mmol, 2.20 equiv.) was added dropwise to this solution. The solution was stirred for 1 hour while warming to room temperature. TLC analysis determined that the starting material had been completely consumed. The clear reaction solution was quenched with ammonium chloride (10 mL). The reaction mixture was taken up into CH$_2$Cl$_2$ (20 mL), washed with ice cold brine (2×10 mL), water (2×10 mL), dried over MgSO$_4$, and the solvent was reduced under vacuum. Purification was performed using a silica gel column with a solvent system of ethyl acetate/petroleum ether (1:9) to yield pure product 3 (99% yield, 0.42 g, 0.95 mmol). This pure product was carried on to the next step with out spectroscopic analysis.

Synthesis of Compound 4

Compound 4 was synthesized according to the procedure in U.S. Patent Application No. US/2007/238702. A flame dried, 50 mL single neck round bottom flask was charged with argon gas, compound 3 (0.367 g, 0.84 mmol, 1.00 equiv.) and anhydrous THF (15 mL). The mixture was stirred at −30° C. and tetrabutylammonium fluoride (TBAF, 0.85 mL, 0.84 mmol, 1.00 equiv.) was added dropwise via syringe to the stirring solution. The mixture was stirred at −30° C. for 1 hour and then at −10° C. for 3 hours. TLC analysis determined that almost complete consumption of starting material had occurred. The clear reaction solution was quenched with ammonium chloride (10 mL). The reaction mixture was taken up in CH$_2$Cl$_2$ (20 mL), washed with brine (2×10 mL), water (2×10 mL), dried over MgSO$_4$, and the solvent was reduced under vacuum. Purification was performed using a silica gel column with a solvent system of ethyl acetate/petroleum ether (3:7) to yield pure product 4 as an clear oil in (90% yield, 0.25 g, 0.76 mmol). $^1$H NMR (400 MHz, CDCl$_3$) δ 4.07 (1H, d, J=2.3 Hz), 3.66 (1H, dd, J=10.5, 3.2, Hz), 3.39 (1H, dd, J=10.5, 6.8 Hz, 22-H), 1.98 (1H, dm, J=12.7 Hz), 1.05 (3H, d, J=6.6 Hz), 0.98 (9H, t, J=7.9 Hz), 0.95 (3H, s), 0.58 (6H, q, J=7.9 Hz); $^{13}$C NMR (125 MHz) δ 69.2, 67.9, 53.1, 52.8, 42.1, 40.6, 38.2, 34.6, 26.8, 23.0, 17.6, 16.6, 13.5, 6.9, 4.9.

Synthesis of Compound 5

Compound 5 was synthesized according to the procedure in U.S. Patent Application No. US/2007/238702. A flame dried 50 mL single neck round bottom flask was charged with argon gas, triphenylphosphine (0.77 g, 2.95 mmol, 3.60 equiv.) and anhydrous $CH_2Cl_2$ (20 mL). The mixture was stirred at 0° C. and $I_2$ (0.83 g, 3.28 mmol, 4.00 equiv.) and imidazole (0.46 g, 6.72 mmol, 8.20 equiv.) were added to the stirring solution in one portion. The deep red mixture was stirred at 0° C. for 10 min. A solution of compound 4 (0.26 g, 0.82 mmol, 1.00 equiv.) in anhydrous $CH_2Cl_2$ (5 mL) was cannulated into the above reaction. The reaction mixture was allowed to stir while warming to room temperature over 17 hours. TLC analysis indicated almost complete consumption of starting material. The red reaction solution was quenched with water (10 mL). The reaction mixture was taken up into $CH_2Cl_2$ (20 mL) and washed with brine (2×20 mL) and water (2×20 mL). The crude material was dried over $MgSO_4$ and reduced under vacuum. Purification was performed using silica gel chromatography with an eluent of ethyl acetate/petroleum ether (1:9) to give pure compound 5 as a slightly yellow oil (0.36 g, 0.82 mmol, 99% yield). $^1H$ NMR (400 MHz, $CDCl_3$) δ 4.04 (1H, d, J=2.1 Hz), 3.33 (1H, dd, J=9.5, 2.3 Hz), 3.17 (1H, dd, J=9.5, 5.3 Hz), 1.90 (1H, dm, J=12.5 Hz), 0.99 (3H, d, J=5.9 Hz), 0.95 (9H, t, J=7.9 Hz), 0.95 (3H, s), 0.55 (6H, q, J=7.9 Hz); $^{13}C$ NMR (100 MHz) δ 69.2, 56.0, 52.8, 42.1, 40.4, 36.4, 34.5, 26.6, 22.8, 21.6, 20.7, 17.1, 14.3, 6.9, 4.9.

Synthesis of Compound 6

To a solution of compound 5 (0.13 g, 0.36 mmol, 1.00 equiv.) in dry dimethylsulfoxide (DMSO, 2 mL) was added KCN (0.05 mg, 0.71 mmol, 1.97 equiv.). The mixture was stirred at 70° C. for 1.5 h. The reaction was quenched with $H_2O$ at 0° C. and then extracted with ethyl acetate. The organic layer was washed with brine, dried over $MgSO_4$, and evaporated. The resulting residue was purified by silica gel column chromatography with an eluent of hexane/ethyl acetate (1:1) to give compound 6 (0.08 g, 81% yield) as a colorless oil. $^1H$ NMR ($CDCl_3$, 400 MHz) δ 0.96 (3H, s, H-18), 1.15 (3H, d, J=6.6 Hz, H-21), 2.25 (1H, dd, J=16.7, 6.9 Hz, H-22), 2.35 (1H, dd, J=16.7, 3.8 Hz, H-22), 4.09 (1H, m, H-8). $^{13}C$ NMR δ 13.8, 17.5, 19.3, 22.6, 24.8, 27.2, 33.2, 33.7, 40.2, 42.1, 52.5, 55.3, 69.1, 119.1.

Synthesis of Compound 7

Compound 6 (0.08 g, 0.24 mmol, 1.00 equiv.) was dissolved in $CH_2Cl_2$ (3 mL). A solution of diisobutylaluminum hydride (DIBAL-H) in toluene (1.00 M, 0.9 mL, 0.90 mmol) was added to the solution of compound 6 at 0° C. The reaction mixture was stirred at the 0° C. for 1.5 hours, then quenched with 10% potassium sodium tartrate (aqueous solution). The aqueous layer was extracted with ether, and the organic layer was washed with brine, dried over $MgSO_4$, and concentrated. The residue was purified by column chromatography (3% EtOAc/hexane) to give compound 7 (0.07 g, 0.21 mmol, 86% yield in two steps). $^1H$ NMR ($CDCl_3$, 400 MHz) δ 9.75 (d, J=2.4 Hz, 1H), 4.08 (s, 1H), 2.45 (dm, J=15.7 Hz, 1H), 2.15 (m, 1H), 1.00 (d, J=6.6 Hz, 3H), 0.98 (s, 3H). $^{13}C$ NMR ($CDCl_3$, 100 MHz) δ 203.46, 69.17, 56.34, 52.54, 50.68, 41.99, 40.22, 33.54, 31.22, 27.40, 22.44, 19.85, 17.34, 13.50.

Synthesis of Compound 8

Compound 7 (0.07 g, 0.21 mmol, 1.00 equiv.) was dissolved in $CH_2Cl_2$ (3 mL). A solution of DIBAL-H in toluene (1 M, 0.9 mL, 0.90 mmol, 4.30 equiv.) was added to the solution of compound 7 at 0° C. The reaction mixture was stirred at 0° C. for 1.5 hours, then quenched with 10% potassium sodium tartrate (aqueous solution). The aqueous layer was extracted with ether and the organic layer was washed with brine, dried over $MgSO_4$, and concentrated. The residue was purified by column chromatography (3% EtOAc/hexane) to give compound 8 (0.06 g, 0.17 mmol, 82% yield) $^1H$ NMR (400 MHz, $CDCl_3$) δ 4.08 (s, 1H), 3.68 (m, 1H), 3.59 (m, 1H), 1.99 (m, 1H), 0.97 (t, J=7.9 Hz, 9H), 0.96 (d, 3H), 0.95 (s, 3H), 0.60 (q, J=7.9 Hz, 6H).

Synthesis of Compound 9

A flame dried 50 mL single neck round bottom flask was charged with argon gas, triphenylphosphine (0.16 g, 0.06 mmol, 3.60 equiv.) and anhydrous $CH_2Cl_2$ (4 mL). The mixture was stirred at 0° C. and $I_2$ (0.17 g, 0.68 mmol, 4.00 equiv.) and imidazole (0.10 g, 1.39 mmol, 8.20 equiv.) were added in one portion to the stirring solution. A deep red mixture developed and was stirred at 0° C. for 10 minutes. A solution of compound 8 (0.06 g, 0.17 mmol, 1 equiv.) in anhydrous $CH_2Cl_2$ (2 mL) was cannulated into the reaction mixture. The reaction mixture was stirred while warming to room temperature over 17 hours. TLC analysis indicated that almost complete consumption of starting material had occurred. The clear reaction solution was quenched with water (10 mL), and the reaction mixture was taken up into $CH_2Cl_2$ (20 mL), washed with brine (2×20 mL), and water (2×20 mL). The crude material was dried over $MgSO_4$ and the solvent was reduced under vacuum. Purification was performed using silica gel column chromatography with an eluent of ethyl acetate/petroleum ether (1:9) to give pure compound 9 as a slightly yellow oil (0.07 g, 0.16 mmol, 97% yield). $^1H$ NMR (400 MHz, $CDCl_3$) δ 4.04 (1H, d, J=2.1 Hz), 3.33 (1H, dd, J=9.5, 2.3 Hz), 3.17 (1H, dd, J=9.5, 5.3 Hz), 2.10-1.87 (2H, m), 1.85-1.40 (7H, 3), 1.40-1.00, (9H, m), 1.00-0.80, (16H, m), 0.55 (6H, q, J=7.9 Hz).

Synthesis of Compound 10

Commercially available (S)-methyl-(S)-phenyl sulfoximine (0.25 g, 1.61 mmol, 1.00 equiv.) and $CH_2Cl_2$ (5 mL) was added to a flame dried, argon charged single neck round bottom flask and cooled to 0° C. The compound, 2,6-lutidine (0.35 g, 3.30 mmol, 0.38 mL, 2.05 equiv.) was then added and the resulting mixture was stirred for 5 minutes. tert-Butyldimethylsilyl trifluoromethanesulfonate (TBSOTf, 0.47 g, 1.77 mmol, 0.40 mL, 1.10 equiv.) was added dropwise, and the reaction mixture was allowed to stir at 0° C. for 2 hrs. When TLC analysis indicated that the reaction was complete, the reaction was quenched with ammonium chloride (20 mL), washed with brine (1×30 mL) and washed with water (1×30 mL). The organic layer was dried over $MgSO_4$ and purified by silica gel column chromatography using an eluent of 20% ethyl acetate/petroleum ether to afford pure compound 10 as a clear oil (1.46 mmol, 0.40 g, 91% yield). $^1H$ NMR ($CDCl_3$, 400 MHz) δ 7.95-7.92 (m, 2H), 7.52-7.48 (m, 3H), 2.97 (s, 3H), 0.91 (s, 9H), 0.04 (s, 3H), 0.03 (s, 3H).

Synthesis of Compound 11

A flame-dried 25 mL recovery flask equipped with a magnetic stir bar and a septum along with an argon balloon was charged with (S)—N-tert butyldimethyl silyl-(S)-sulfoximine (compound 10, 0.56 g, 2.10 mmol, 6.00 equiv.) dissolved in 3.0 mL of freshly distilled tetrahydrofuran (THF) and 0.30 mL of hexamethylphosphoramide (HMPA). The flask was then cooled to −78° C. in a 2-propanol/dry ice bath. To this solution was added n-BuLi (2.10 mmol, 1.31 mL, 1.6 M solution in hexanes, 6.00 equiv.) dropwise over several minutes and a pale yellow color developed. This mixture was stirred at −78° C. for an additional 30 minutes.

A flame-dried 10-mL pear-shaped flask equipped with a septum and an argon balloon was charged with compound 9 (0.11 g, 0.22 mmol, 1.00 equiv.) dissolved in 2.0 mL of freshly distilled THF. The solution was cooled to −78° C. in a 2-propanol/dry ice bath, and was transferred into the flask containing the lithiated sulfoximine at −78° C. via cannula over several minutes. After complete addition, the mixture was gradually warmed to room temperature and stirred for about 8 hours. Thin-layer chromatography (TLC) indicated that complete consumption of starting material had occurred. The reaction was quenched by addition of 6 mL of buffer solution (pH 7), and rinsed into a separatory funnel with ethyl acetate. The mixture was extracted with ethyl acetate (3×25 mL). The extracts were combined, washed with water (1×25 mL), washed with brine solution (1×25 mL), dried over $Na_2SO_4$, and filtered. The filtrate was concentrated in vacuo and the crude product was purified by flash column chromatography (1:1 ethyl acetate/hexanes) to afford pure product (0.08 g, 0.13 mmol, 60% yield).

The intermediate was added to an argon-purged 25 mL round bottom flask equipped with a magnetic stir bar and dissolved in acetonitrile (12 mL) to give about a 0.04 M solution. This solution was stirred and an HF solution was added (13.1 mmol, 0.50 mL, 100 equivs) via syringe at room temperature. The resulting mixture was stirred at room temperature for 4 hours. TLC indicated that the reaction had gone to completion. The reaction mixture was diluted with ether (25 mL), and a saturated solution of $NaHCO_3$ was added until the liberation of carbon dioxide ceased. The reaction mixture was then rinsed into a separatory funnel with ethyl acetate and extracted with ethyl acetate (4×25 mL). The extracts were combined, washed with water (1×25 mL), washed with brine solution (1×25 mL), dried over $Na_2SO_4$, and filtered. The filtrate was concentrated in vacuo to give the crude product. Crude compound 11 was purified via flash column chromatography with 100% ethyl acetate as the eluent to afford pure compound 11 (0.055 g, 0.12 mmol, 90% yield) as a viscous oil. $^1H$ NMR ($CDCl_3$, 400 MHz) δ 7.97-7.95 (m, 2H), 7.64-7.53 (m, 3H), 4.05 (br s, 1H), 3.20 (ddd, 1H, J=4.4, 12.0, and 13.6 Hz), 3.03 (ddd, 1H, J=4.4, 12.0, and 13.6 Hz), 2.67 (br s, 1H), 1.93-1.68 (m, 6H), 1.58-1.37 (m, 5H), 1.30-0.95 (m, 5H), 0.87 (s, 3H), 0.84 (d, 3H, J=6.4 Hz).

Synthesis of Compound 12

A flame-dried 10-mL recovery flask equipped with a magnetic stir bar, a septum, and an argon balloon was charged with the compound 11 (0.045 g, 0.12 mmol, 1.00 equiv.), which was dissolved in 5.0 mL of freshly distilled $CH_2Cl_2$ to give a 0.04 M solution. To this solution were added pyridinium dichromate (PDC, 0.10 g, 0.25 mmol, 2.10 equiv.) and 0.10 g of oven-dried Celite in one portion at room temperature. The resulting mixture was stirred at room temperature for about 12 hours. TLC indicated when complete consumption of starting material had occurred. The resulting mixture was directly purified by column chromatography using 100% ethyl acetate as the eluent to afford compound 12 (0.031 g, 0.086 mmol, 72% yield). $^1H$ NMR ($CDCl_3$, 400 MHz) δ 7.98-7.95 (m, 2H), 7.65-7.54 (m, 3H), 3.21 (ddd, 1H, J=4.4, 12.0, and 13.6 Hz), 3.04 (ddd, 1H, J=4.4, 12.0, and 13.6 Hz), 2.67 (s, 1H), 2.42 (dd, 1H, J=8.0 and 11.6 Hz), 2.30-2.16 (m, 2H), 2.05-1.95 (m, 2H), 1.93-1.65 (m, 5H), 1.60-1.35 (m, 4H), 1.27-1.19 (m, 1H), 0.91 (d, 3H, J=6.4 Hz), 0.58 (s, 3H).

Synthesis of Compound Icii

Compounds 12 and 13 were azeotropically dried with anhydrous benzene (5×10 mL) on a rotary evaporator and held under vacuum (about 0.1 mmHg) for at least 96 hours prior to use. A flame-dried 10-mL recovery flask equipped with a magnetic stir bar, a septum, and an argon balloon was charged with phosphine oxide (0.094 g, 0.21 mmol, 3.00 equiv.), which was dissolved in 1.0 mL of freshly distilled THF to give about a 0.1 M solution. The flask was cooled to −78° C. in a 2-propanol/dry ice bath and n-BuLi (130 µL, 0.21 mmol, 1.6 M solution in hexanes) was added dropwise over several minutes. A deep red color developed and persisted. This mixture was allowed to stir at −78° C. for an additional 10 minutes.

A flame-dried 10-mL recovery flask equipped with a magnetic stir bar, a septum, and an argon balloon was charged with compound 12 (0.025 g, 0.069 mmol, 1 equiv.), which was dissolved in 1 mL of freshly distilled THF and cooled to −78° C. in a 2-propanol/dry ice bath. The solution was transferred dropwise into the flask containing the phosphine oxide anion at −78° C. via cannula over several minutes. After the addition was complete, a deep red color persisted and the mixture was stirred at −78° C. for about 8 h. At this time the color of the reaction was monitored. Upon observation of a light yellow color, the reaction was quenched at −78° C. by addition of 5 mL of buffer (pH 7) and allowed to warm to room temperature. The mixture was then rinsed into a separatory funnel with ethyl acetate and extracted with ethyl acetate (3×25 mL). The extracts were combined, washed with water (1×25 mL), washed with brine solution (1×25 mL), dried over $Na_2SO_4$, and filtered. The filtrate was concentrated in vacuo to afford the crude product, which was purified by column chromatography using 50% ethyl acetate in hexanes in the presence of 1% triethylamine as the eluent. The resulting coupled product (0.018 g, 0.025 mmol, 65% yield) was charged into a 5 mL argon-purged polypropylene vial equipped with a magnetic stir bar and dissolved in 2.5 mL of acetonitrile to give about a 0.02 M solution. This solution was well-stirred HF (2.50 mmol, 86 µL, 49% aqueous solution) was added to it via syringe at room temperature. The mixture was stirred at room temperature in the dark for 5 hours. TLC indicated that completion of the reaction had occurred. The reaction mixture was diluted with ether (25 mL), and a saturated solution of $NaHCO_3$ was added until the liberation of carbon dioxide ceased. The reaction mixture was then rinsed into a separatory funnel with ethyl acetate, and extracted with ethyl acetate (5×25 mL). The extracts were combined, washed with water (1×25 mL), washed with brine solution (1×25 mL), dried over $Na_2SO_4$, and filtered. The filtrate was concentrated in vacuo to give crude product that was purified by column flash chromatography using 99% ethyl acetate in the presence of 1% triethylamine as the eluent to afford compound Icii. $[α]_D^{22=}$+81.6 (c=0.35, MeOH); IR (neat) 3326, 2944, 2874, 1673, 1593, 1580, 1448, 1406, 1379, 1280, 1231, 1147, 1055, 989, 910 $cm^{-1}$; $^1H$ NMR (Methanol $d_4$, 400 MHz) δ 7.98-7.89 (d, 2H, J=8.0 1H), 7.64-7.52 (m, 3H), 6.12 (d, 1H, J=12.0 Hz), 5.92 (d, 1H, J=12.0 Hz), 4.94, (s, 1H), 4.65 (s, 1H), 4.00 (bs, 1H), 3.75-3.60 (m, 1H), 3.17-3.00 (m, 2H), 2.80-2.70 (m, 1H), 2.50-2.2 (m, 2H), 2.15-1.97 (m, 2H), 1.93-0.92 (m, 20H), 0.79 (d, 4H, J=6.4 Hz), 0.43 (s, 3H); $^{13}C$ (Methanol $d_4$, 125 MHz) δ 147.0, 142.3, 137.4, 134.5, 130.4, 129.6, 122.6, 119.0, 112.6, 70.5, 58.6, 57.6, 57.4, 49.7, 49.6, 47.0, 46.9, 41.8, 37.0, 36.6, 35.4, 33.6, 29.9, 28.6, 24.5, 23.2, 21.2, 19.0, 12.3; HRMS (FAB, M+H$^+$) calcd. 482.3093 for $C_{30}H_{43}NO_2S$. found 482.3087; UV (MeOH) $λ_{max}$ 264 nm (ϵ 23,987).

Example 6: Binding of Prodrug Ibii to the Vitamin D Receptor (VDR)

Human recombinant VDR (1 pmol/reaction) prepared in Tris-HCl binding buffer (containing 5 mg/mL gelatin and 10 mM dithiothreitol (DTT)) was mixed gently with various concentrations of Ibii or calcitriol ($10^{-7}$ to $10^{-10}$ M) for 1 hour at room temperature. Then, [26,27-methyl-$^3$H]-1α,25

$(OH)_2D_3$ (0.25 nM; about 20,000 cpm) was added to each tube, mixed, and incubated for 1 hour at room temperature. Unbound radioactive ligand was removed by incubation with dextran-charcoal for 30 min on ice and pelleted by centrifugation at 2000 rpm for 10 min at 4° C. The radioactivity in 100 mL of the supernatant was measured using a scintillation counter. The control reactions contained either no VDR protein (background) or no competing ligand (maximum binding). The mean background binding was subtracted and the data divided by the mean maximum binding to yield $B/B_{max}$ values. The concentration necessary to displace 50% of $[26,27\text{-methyl-}^3H]\text{-}1\alpha,25(OH)_2D_3$ from VDR was calculated as the $B_{50}$.

FIG. 1 is a graph showing the binding of Prodrug Ibii to the VDR compared to 1,25-dihydroxyvitamin $D_3$. Prodrug Ibii does not substantially bind to the VDR in vitro ($B_{50}$>1000 nM), while 1,25-dihydroxyvitamin $D_3$ has $B_{50}$=0.39 nM.

Example 7: Activation of CYP24A1 Transcription by Prodrug Ibii

HPK1a-ras cells were maintained in Dulbecco's Modified Eagle's medium (DMEM) supplemented with 10% Fetal Bovine Serum and plated at $1\times10^5$ cells/well in 24-well plates. The media was exchanged after 24 hours for DMEM containing 1% Bovine Serum Albumin. Cells were treated in duplicate with Ibii and control compounds at various concentrations ($10^{-6}$ to $10^{-9}$M) for 6 or 7 hours. Extraction of cellular RNA was performed using Trizol® (Invitrogen). Aliquots of RNA were reverse-transcribed to cDNA using random hexamers and Thermoscript reverse transcriptase according to the manufacturer's instructions (Invitrogen). Quantitative real-time PCR was performed using an ABI StepOnePlus system using the Taqman Universal PCR Master Mix. PCR reaction volumes of 20 µL were used with 50 cycles of amplification. Each cDNA sample was tested in duplicate using TaqMan® gene expression assays with the following ID numbers: human GAPDH (Hs99999905_m1), human CYP24 (Hs00167999_m1). The real-time PCR results were analyzed using the StepOne system software V2.1. Gene expression levels were calculated using the comparative CT method, and normalized to the GAPDH expression levels.

Prodrug Ibii reproducibly and significantly induces transcription of CYP24 in HPK1aRas cells (FIGS. 2a-2d). Prodrug Ibii induced transcription of CYP24 about 100-fold at 100 nM and about 500-fold at 1 µM, when compared to vehicle. Prodrug Ibii was about ¹⁄₁₀₀ as potent as its 1-hydroxylated analog. Lower concentrations of Prodrug Ibii did not significantly induce the transcription of CYP24A1. Because Prodrug Ibii does not bind to the VDR, transcription upregulation of CYP24 by Prodrug Ibii is likely occurring through its 1-hydroxylated analog, which is expected to result from hydroxylation of Prodrug Ibii at position-1 by CYP27b1.

Example 8: Activation of CYP27b1 Transcription by Prodrug Ibii

HPK1a-ras cells were maintained in Dulbecco's Modified Eagle's medium (DMEM) supplemented with 10% Fetal Bovine Serum and plated at $1\times10^5$ cells/well in 24-well plates. The media was exchanged after 24 hours for DMEM containing 1% Bovine Serum Albumin. Cells were treated in duplicate with Ibii and control compounds at various concentrations ($10^{-6}$ to $10^{-9}$M) for 6 or 7 hours. Extraction of cellular RNA was performed using Trizol® (Invitrogen). Aliquots of RNA were reverse-transcribed to cDNA using random hexamers and Thermoscript reverse transcriptase according to the manufacturer's instructions (Invitrogen). Quantitative real-time PCR was performed using an ABI StepOnePlus system using the Taqman Universal PCR Master Mix. PCR reaction volumes of 20 µL were used with 50 cycles of amplification. Each cDNA sample was tested in duplicate. The real-time PCR results were analyzed using the StepOne system software V2.1. Gene expression levels were calculated using the comparative CT method, and normalized to the GAPDH expression levels.

Figure 3:
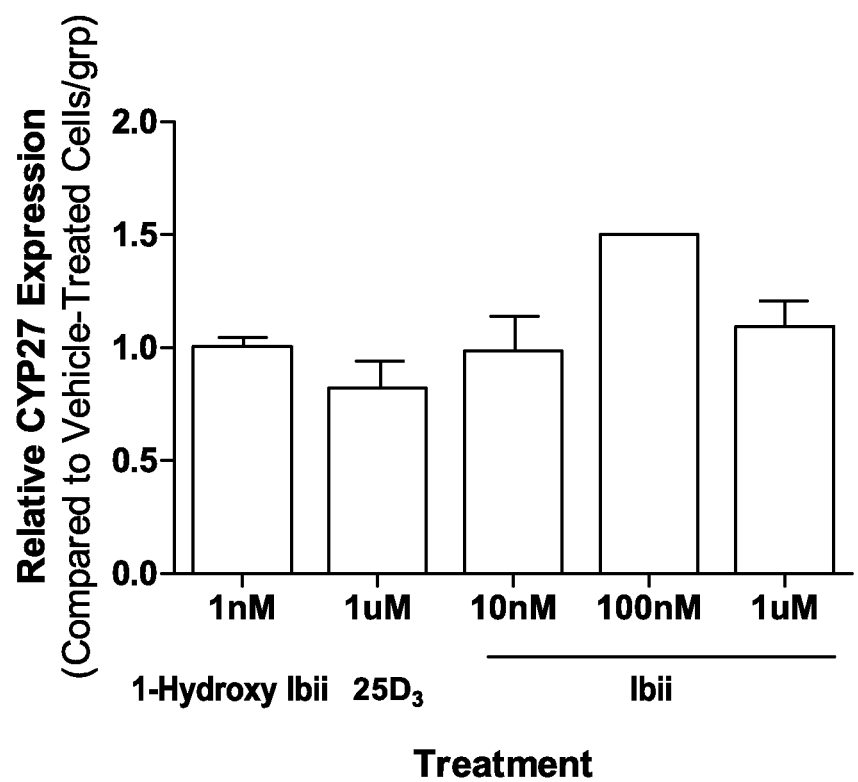
FIG. 3 shows the relative CYP27B1 transcription in HPK1aRas cells treated with Prodrug Ibii compared to 25-hydroxyvitamin $D_3$ and the 1-hydroxy active form of Prodrug Ibii.

The transcription of CYP27b1 was not significantly affected by Prodrug Ibii when compared to vehicle (FIG. 3).

Example 9: Comparison of Prodrug Ibii and its 1-Hydroxy Active Metabolite on PTH, Calcium, and FGF23 Levels in Adenine-Induced Uremic Rats The effect of Prodrug Ibii compared to its 1-hydroxy analog on PTH and calcium levels in 80 male Sprague-Dawley rats is determined as follows. Rats about 6 weeks old, about 175-250 g (with weight variation not exceeding ±15% of the mean weight) were given through oral gavage a solution containing 100 mg of adenine daily for two weeks, and then divided into eight groups of 10 males each. The groups are administered either vehicle, Prodrug Ibii, or the 1-hydroxy analog of Prodrug Ibii three times per week for two weeks, according to the Table below:

| Group | Adenine gavage 100 mg (2 weeks) | Dose (mcg/kg) | Dose Volume for i.v. injection (mL/kg) | No. of Animals |
|---|---|---|---|---|
| 1. Vehicle | Yes | — | 0.8 | 10 |
| 2. Prodrug Ibii | | 0.2 | | |
| 3. Prodrug Ibii | | 1 | | |
| 4. Prodrug Ibii | | 5 | | |
| 5. Prodrug Ibii | | 10 | | |
| 6. 1-Hydroxy active form of Prodrug Ibii | | 0.2 | | |
| 7. 1-Hydroxy active form of Prodrug Ibii | | 1 | | |
| 8. 1-Hydroxy active form of Prodrug Ibii | | 5 | | |

Figure 4:
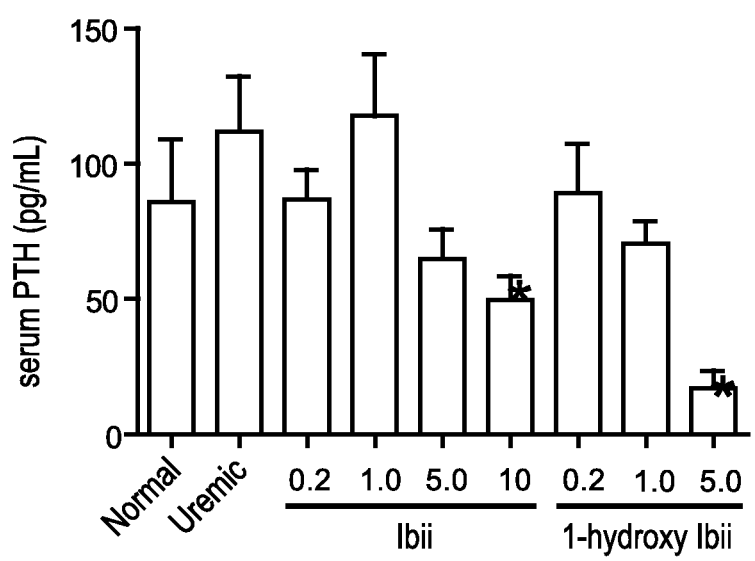
FIG. 4 shows results of serum PTH suppression in uremic rats by Prodrug Ibii and the 1-hydroxy active form of Prodrug IIb, demonstrating that Prodrug Ibii can be transformed in vivo and suppress PTH in uremic rats.
Figure 5:
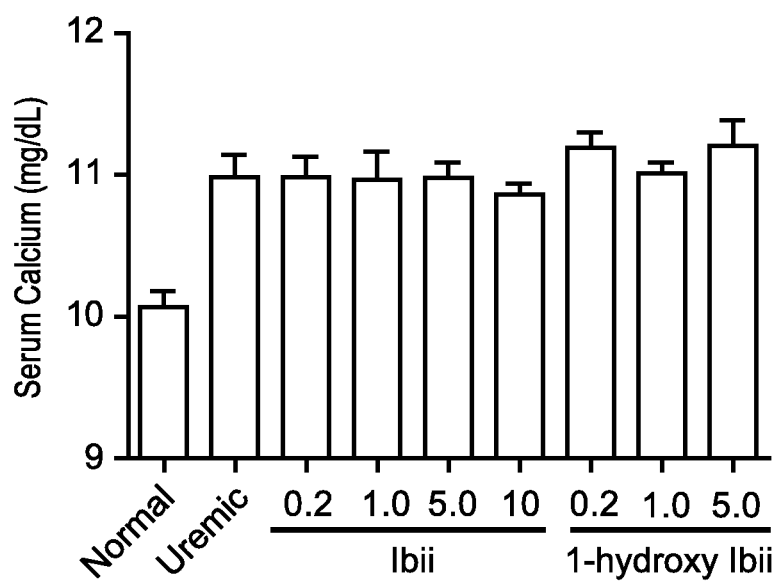
FIG. 5 shows the effect on serum calcium in uremic rats by Prodrug Ibii and the 1-hydroxy active form of Prodrug IIb, demonstrating that Prodrug IIbii is a non-calcemic vitamin D analog prodrug.

The body weight of each animal is determined prior to dosing and every week thereafter. During the study, the animals are fed Labdiet 5002 (see http://www.labdiet.com/pdf/5002.pdf). Day 0 is the first day of dosing. Approximately 1 mL of blood was collected from each animal at day 1 (24 hours), day 7, and day 14 to be used for the preparation of serum. Serum PTH, calcium, FGF23 and phosphate were measured using the blood samples. At the end of the study, the animals were sacrificed and serum was collected. The kidneys, intestine, parathyroid glands, liver and bone from each animal were also collected. The levels of CYP24 and other genes of interest were measured. Data from this study demonstrate that (i) Ibii can lower circulating iPTH levels in the serum of adenine treated rats and that the potency of Ibii that decreases circulating iPTH levels is comparable to but lower than the 1-hydroxy active form of Ibii administered directly (FIG. 4); (ii) Ibii is non-calcemic and displays a comparable or lesser effect on serum calcium compared to the 1-hydroxy active form of Ibii administered directly (FIG.

Figure 6:
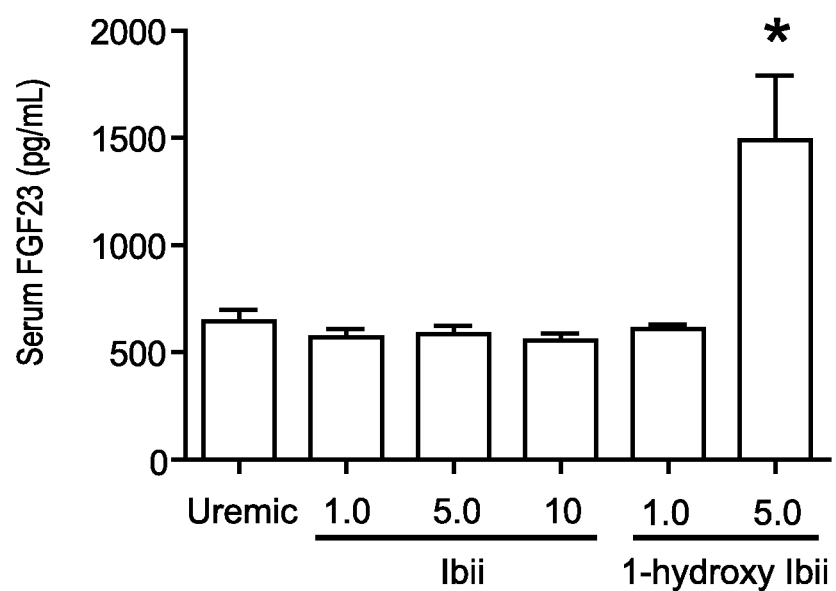
FIG. 6 shows the effect on serum FGF23 levels in uremic rats by Prodrug Ibii and the 1-hydroxy active form of Prodrug IIb, demonstrating that Prodrug IIbii does not increase serum FGF23 levels in uremic rats.

5); (iii) Ibii does not increase serum FGF23 levels, and has less effect on serum FGF23 levels than the 1-hydroxy active form of Ibii administered directly (FIG. 6).

Example 10: Bioavailability and Safety of Prodrug Ibii in Vitamin D-Deficient Rats Vitamin D deficient Sprague Dawley rats were treated with Ibii 3x/week for five days by IV and oral routes, according to the Table below:

| Group | Route | Formulation | Dose (µg/kg) | Dose Volume (mL/kg) | No. of Animals |
|---|---|---|---|---|---|
| Vehicle | Intravenous | Propylene glycol:water:ethanol (30:50:30) | — | 0.8 | 20 |
| Prodrug Ibii | | | 160 | 0.8 | 20 |
| Vehicle | Oral | Corn oil:ethanol (96:4) | — | 8.0 | 20 |
| Prodrug Ibii | | | 160 | 8.0 | 20 |

Figure 7:
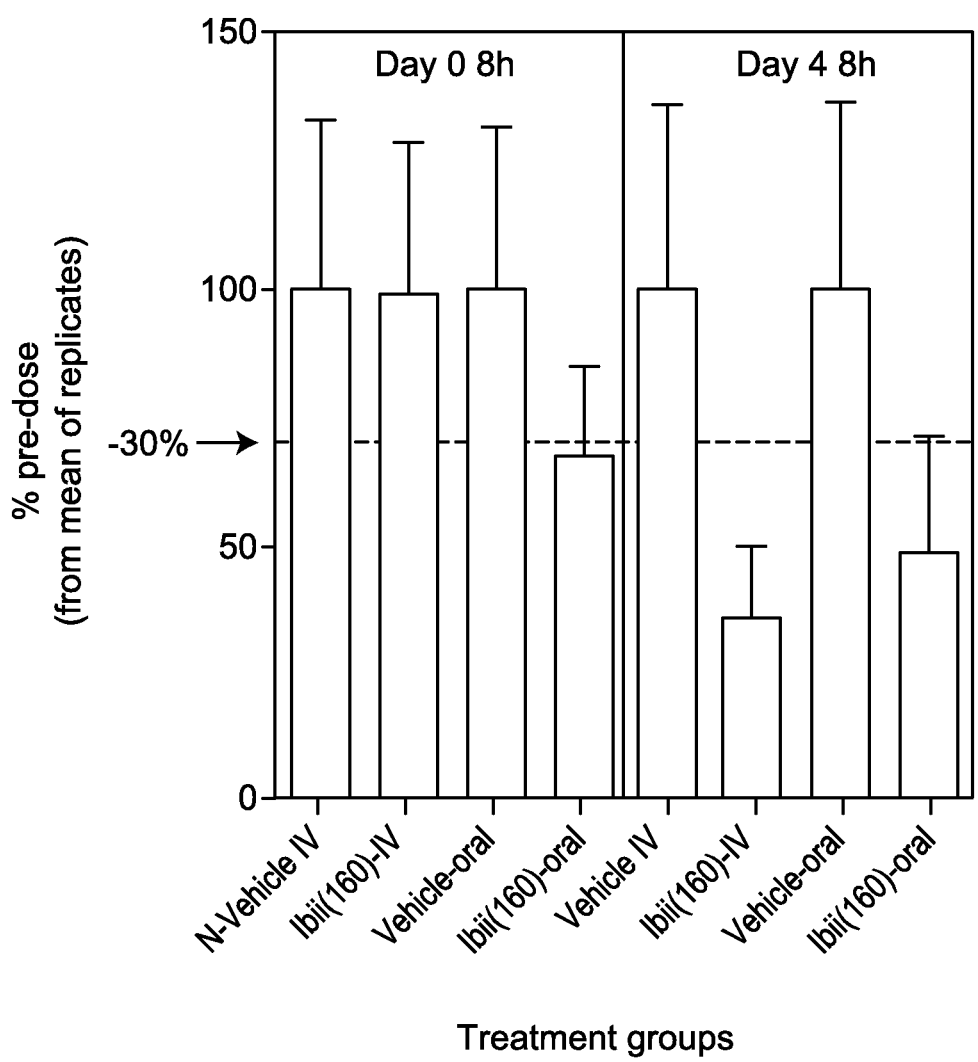
FIG. 7 shows the effect on PTH by Prodrug Ibii in vitamin D deficient animals treated 3×/week for five days via oral and IV dosing, demonstrating that both IV and orally-administered Prodrug Ivii can effectively lower PTH.
Figure 8:
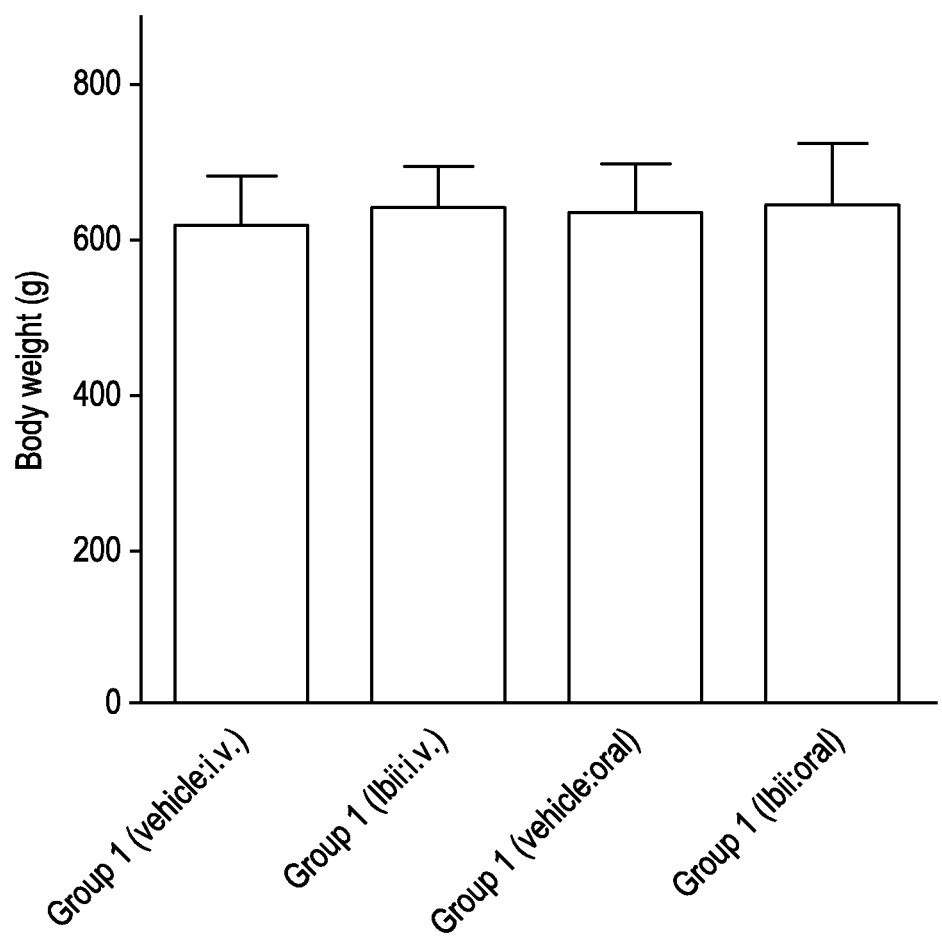
FIG. 8 shows the effect on body weight by Prodrug Ibii in Vitamin D deficient rats, demonstrating that Prodrug Ibii does not exhibit overt toxicity.

The effects of administration of Ibii and vehicle alone on PTH are shown in FIG. 7, and demonstrate that both IV-administered and orally-administered Ibii can effectively lower PTH. The effects on body weight of Ibii by IV and oral administration are shown in FIG. 8, and demonstrate that Ibii does not exhibit overt toxicity.

Example 11: Effect on CYP24 Expression in Cells which do not Substantially Express CYP27B1

Figure 9:
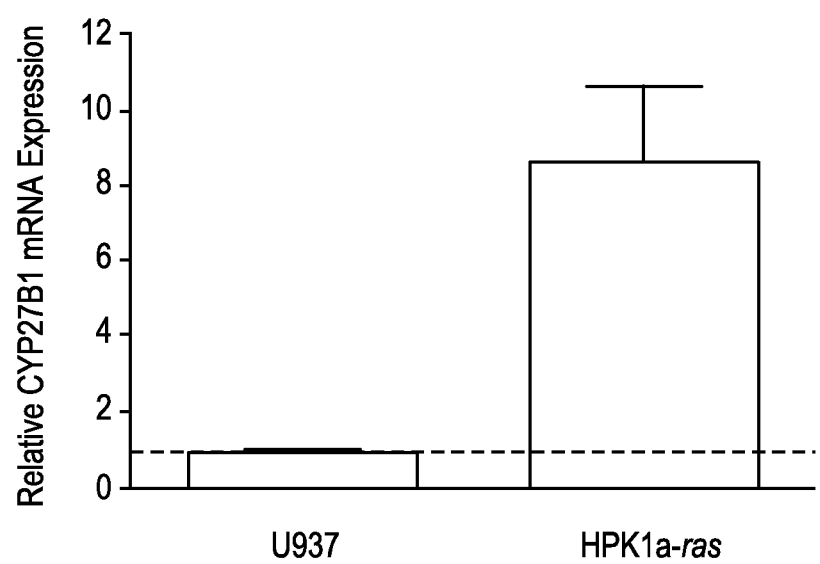
FIG. 9 shows the relative CYP27B1 mRNA expression in U937 and HPK1a-ras cells, demonstrating that HPK1a-ras cells exhibit a higher expression of CYP27B1 mRNA compared to U937 cells.

PMA-stimulated U937 cells were maintained in RPMI media supplemented with 10 mM HEPES, 1 mM sodium pyruvate, 0.1 mM non-essential amino acids and 10% Fetal Bovine Serum at optimal cell density (between $1 \times 10^5$ cells/mL and $2 \times 10^6$ cells/mL). Prior to treatment, cells were pelleted by centrifugation and resuspended to a concentration of $5 \times 10^5$ cells/mL. Cells were then treated with phorbol myristate acetate (PMA) at a final concentration of 20 ng/ml. To each well of a 24-well plate, 1 ml of cell suspension was added, which was incubated overnight at 37° C.+5% CO2. The following day, RPMI media was replaced with fresh media and cells were treated in triplicate with vehicle or compounds at various concentrations ($10^{-7}$ to $10^{-9}$ M) for 6 hr at 37° C. Media was removed and extraction of cellular RNA was performed using Trizol® (Invitrogen). Aliquots of RNA were reverse-transcribed to cDNA using oligo dT primers and Thermoscript reverse transcriptase according to the manufacturer's instructions (Invitrogen). Quantitative real-time PCR was performed using an ABI StepOnePlus system using the Taqman Universal PCR Master Mix. PCR reaction volumes of 20 µl were used with 50 cycles of amplification. Each cDNA sample was tested in duplicate using TaqMan® gene expression assays with the following ID numbers: human GAPDH (Hs99999905_m1), human CYP24 (Hs00167999_m1). The real-time PCR results were analyzed using the StepOne system software V2.1. Gene expression levels were calculated using the comparative CT method, and normalized to the GAPDH expression levels. The U937 cells have a low level of expression of CYP27B1 mRNA, for example compared to HPK1a-ras cells. See FIG. 9. Results of measurements of CYP24 expression are shown in FIGS. 10-12.

Figure 10:
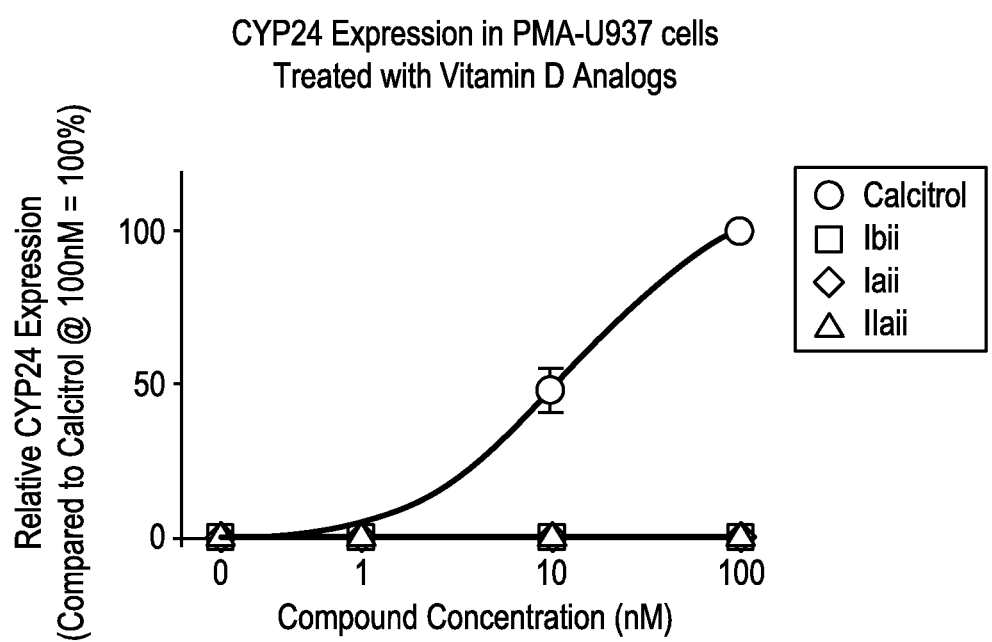
FIGS. 10-12 show relative CYP24 expression (compared to calcitriol) in PMA-U927 cells treated with calcitriol and Prodrugs Ibii, Iaii and IIaii described herein at concentrations up to 100 nM (FIG. 10) and with calcitriol and Prodrugs Ibii, Ieii, Icii, and Idii described herein at concentrations up to 100 nm (FIGS. 11 and 12), demonstrating that in cells which do not substantially express CYP27B1, the Prodrugs are inactive. The y-axis on FIG. 12 has been segmented to show detail at lower levels of relative CYP24 expression for the Prodrugs.
Figure 11:
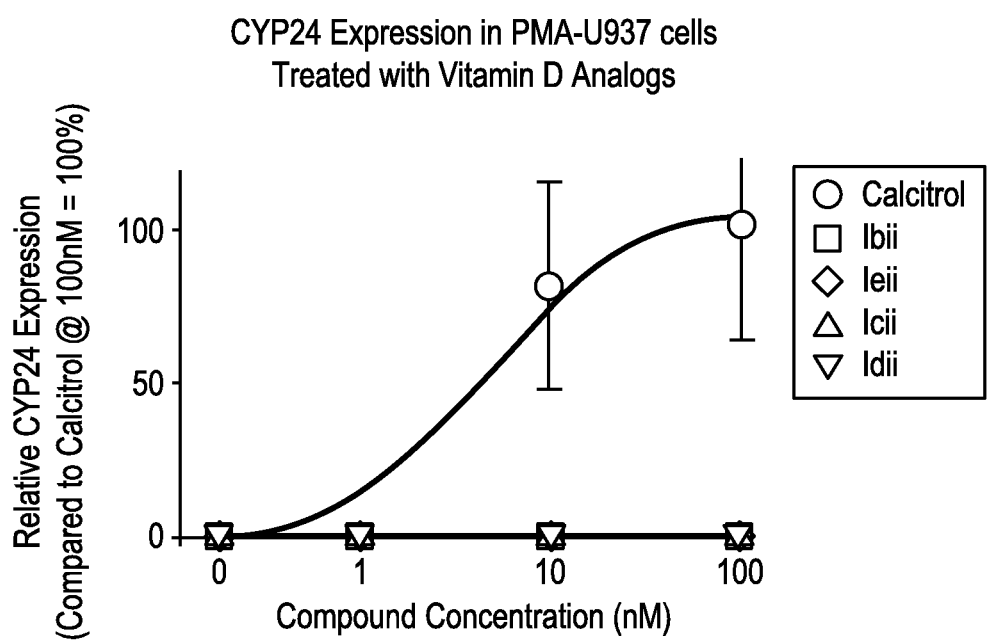
Figure 12:
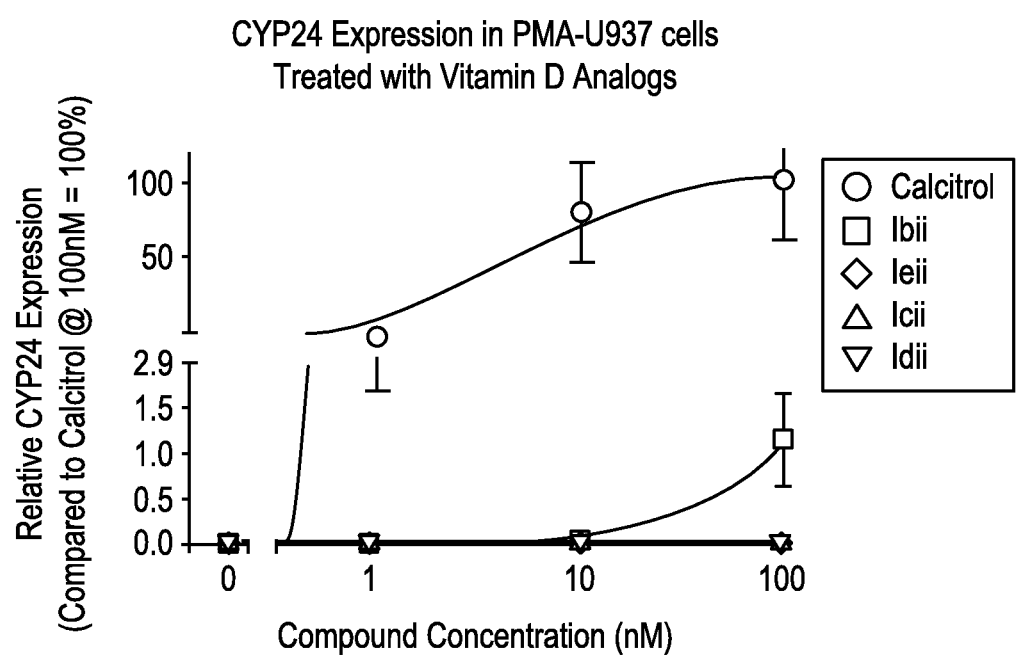

FIGS. 10-12 show relative CYP24 expression (compared to calcitriol) in PMA-U927 cells treated with calcitriol and Prodrugs Ibii, Iaii and IIaii described herein at concentrations up to 100 nM (FIG. 10) and with calcitriol and Prodrugs Ibii, Ieii, Icii, and Idii described herein at concentrations up to 100 nm (FIGS. 11 and 12). The y-axis on FIG. 12 has been segmented to show detail at lower levels of relative CYP24 expression for the Prodrugs. The results demonstrate that in cells which do not substantially express CYP27B1, the Prodrugs are inactive.

Figure 13:
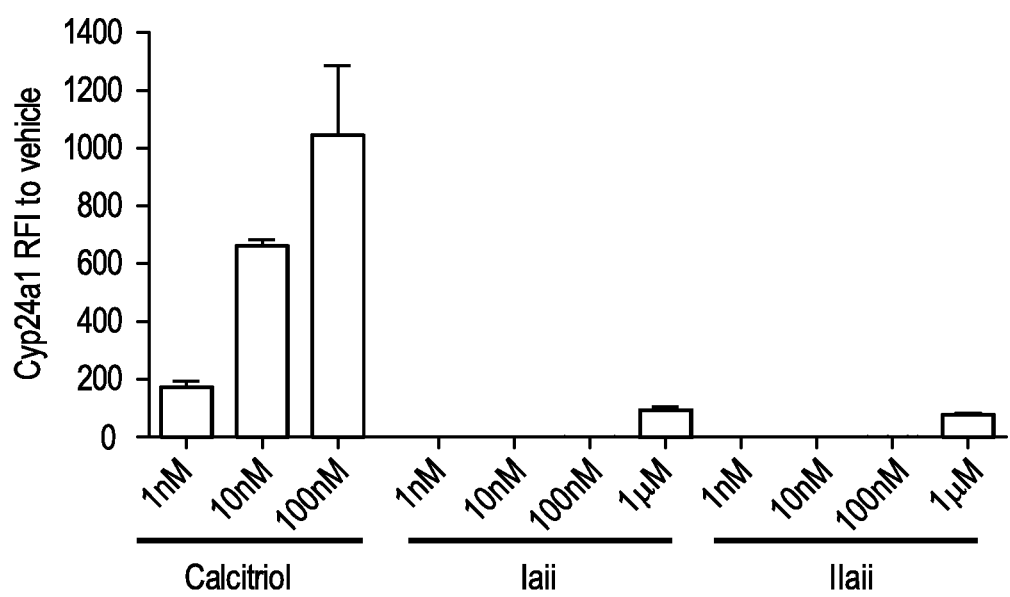
FIG. 13 shows CYP24 transcription activity in HPK1a-ras cells for calcitriol, Prodrug Iaii, and Prodrug IIaii described herein, demonstrating that Prodrug Iaii, and Prodrug IIaii (in cells which express CYP27B1) are active, but less potent than Prodrug Ibii in these cells because they display significant transcriptional activity only when used at 1000 nM compared to at 100 nM for Prodrug Ibii (RFI=relative fold induction).

Example 12: Transcriptional Activity of Prodrugs Iaii and IIaii in HPKA1A-Ras Cells As described above, HPK1a-ras cells exhibit a significantly higher expression of CYP27B1 mRNA compared to U937 cells. See FIG. 9. CYP24a1 transcription activity in HPK1a-ras cells was determined for prodrugs Iaii and IIaii. As with the protocol described in Example 7, HPK1a-ras cells were maintained in Dulbecco's Modified Eagle's medium (DMEM) supplemented with 10% Fetal Bovine Serum and plated at $1 \times 10^5$ cells/well in 24-well plates. Prior to treatment with compounds, cells were washed with PBS and replaced with DMEM containing 1% Bovine Serum Albumin. Cells were treated in duplicate with vehicle or compounds at various concentrations ($10^{-6}$ to $10^{-9}$ M) for 6 hr at 37° C. Media was removed and extraction of cellular RNA was performed using Trizol® (Invitrogen). Aliquots of RNA were reverse-transcribed to cDNA using oligo dT primers and Thermoscript reverse transcriptase according to the manufacturer's instructions (Invitrogen). Quantitative real-time PCR was performed using an ABI StepOnePlus system using the Taqman Universal PCR Master Mix. PCR reaction volumes of 20 µl were used with 50 cycles of amplification. Each cDNA sample was tested in duplicate using TaqMan® gene expression assays with the following ID numbers: human GAPDH (Hs99999905_m1), human CYP24 (Hs00167999_m1). The real-time PCR results were analyzed using the StepOne system software V2.1. Gene expression levels were calculated using the comparative CT method, and normalized to the GAPDH expression levels FIG. 13 shows CYP24 transcription activity in HPK1a-ras cells for calcitriol, Prodrug Iaii, and Prodrug IIaii described herein, demonstrating that Prodrug Iaii, and Prodrug IIaii (in cells which express CYP27B1) are active. These prodrugs are less potent than Prodrug Ibii in these cells because they display significant transcriptional activity only when used at 1000 nM compared to at 100 nM for Prodrug Ibii. Because Prodrugs Iaii and IIaii do not bind to the VDR, transcription upregulation of CYP24 by Prodrugs Iaii and IIaii is likely occurring through its 1-hydroxylated activated form, which is expected to result from hydroxylation of Prodrug Iaii and IIaii at their respective position-1 by CYP27b1.

Example 12: Transcriptional Activity and CYP24 Inhibitory Activity of Prodrugs Icii, Idii, and Ieii in HPK1A-Ras Cells Transcriptional activity of calcitriol and Prodrugs was determined by CYP24a1 relative transcription in HPK1a-ras cells treated for 6 hours with calcitriol, combinations of calcitriol with Prodrugs Icii, Idii, and Ieii, and combinations of calcitriol with 1-hydroxylated active forms of Prodrugs Icii, Idii, and Ieii which are known CYP24 inhibitors. Results are shown in FIGS. 14 and 15.

Figure 14:
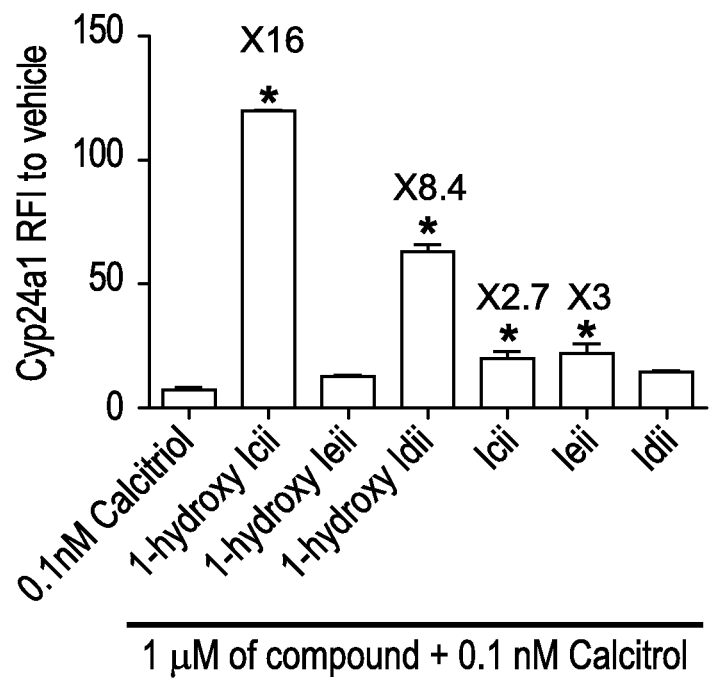
FIGS. 14 and 15 show CYP24 transcription activity in HPK1a-ras cells for calcitriol alone and calcitriol together with each of Prodrug Icii, Prodrug Ieii, Prodrug Idii, and the 1-hydroxy activated forms thereof at 1 μM concentrations of the analogs and 0.1 nM calcitriol (FIG. 14) and 1 nM calcitriol (FIG. 15) (RFI=relative fold induction). The results demonstrate the CYP24 inhibitory effect by administration of all test compounds in these CYP27B1-expressing cells.
Figure 15:
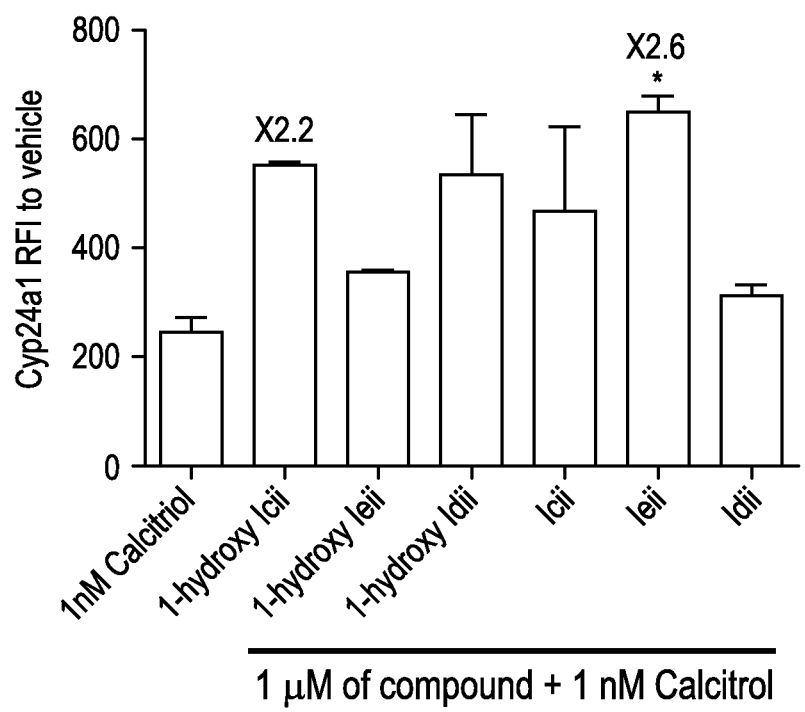

FIGS. 14 and 15 show CYP24 transcription activity in HPK1a-ras cells for calcitriol alone and calcitriol together with each of Prodrug Icii, Prodrug Ieii, Prodrug Idii, and the 1-hydroxy activated forms thereof at 1 µM concentrations of the analogs and 0.1 nM calcitriol (FIG. 14) and 1 nM calcitriol (FIG. 15). The results demonstrate the CYP24 inhibitory effect by administration of all test compounds in these CYP27B1-expressing cells. Increased CYP24a1 transcription activity when the test compounds are administered together with calcitriol is a response to the increased halflife of calcitriol achieved via CYP24 inhibition by the test compounds.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

Throughout the specification, where compositions are described as including components or materials, it is contemplated that the compositions can also consist essentially of, or consist of, any combination of the recited components or materials, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A compound having Formula I, or a pharmaceutically acceptable salt, solvate, or hydrate thereof:

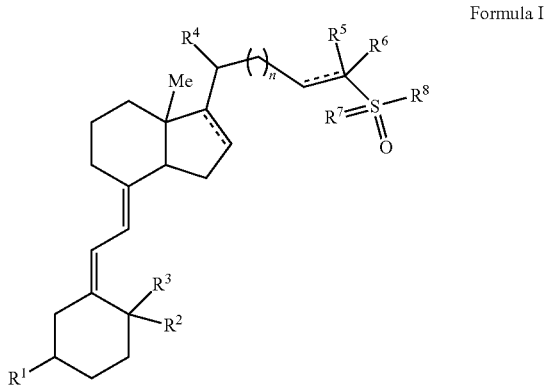

Formula I wherein each --- independently is a single bond or a double bond;
n is 0, 1 or 2;
$R^1$ is selected from the group consisting of OH, $OC_{1-6}$alkyl, and halo;
$R^2$ and $R^3$ are each independently H or halo, or together form $=CH_2$;
$R^4$ is $C_{1-6}$alkyl;
$R^5$ and $R^6$ are each independently H, halo, $C_{1-4}$alkyl, or can be taken, together with the carbon atom to which they are bound, to form a $C_{3-6}$cycloalkyl ring, with the proviso that when --- between carbon-23 and carbon-24 is a double bond, then $R^5$ is absent;
$R^7$ is selected from the group consisting of O, NH, $N(C_{1-6}$alkyl), and $NC(O)R^9$;
$R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo, OH, $OCF_3$, SH, $SC_{1-4}$alkyl, $NH_2$, $NHC_{1-4}$alkyl, $N(C_{1-4}$alkyl)$(C_{1-4}$alkyl), and CN; and
$R^9$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo;
with the proviso that when n is 0, then $R^7$ is O; and
with the proviso that when each --- is a single bond, n is 1, $R^1$ is OH, $R^2$ and $R^3$ together form $=CH_2$, $R^4$ is $C_1$alkyl, $R^5$ and $R^6$ are each H, and $R^8$ is methyl, then $R^7$ is selected from the group consisting of NH, N$(C_{1-6}$alkyl), and $NC(O)R^9$.

2. The compound of claim 1, wherein
n is 0 or 1;
$R^1$ is OH or halo;
$R^2$ and $R^3$ are either both H or together form $=CH_2$;
$R^4$ is $C_{1-4}$alkyl;
$R^5$ and $R^6$ are each independently H, halo, or $C_{1-2}$alkyl, with the proviso that when --- between carbon-23 and carbon-24 is a double bond, then $R^5$ is absent;
$R^7$ is selected from the group consisting of 0, NH, and $N(C_{1-6}$alkyl); and
$R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo.

3. The compound of claim 2, wherein
$R^1$ is OH or F;
$R^2$ and $R^3$ together form $=CH_2$;
$R^4$ is $CH_3$;
$R^5$ and $R^6$ are each independently H, halo, or $CH_3$, with the proviso that when --- between carbon-23 and carbon-24 is a double bond, then $R^5$ is absent;
$R^7$ is O or NH; and
$R^8$ is selected from the group consisting of $C_{1-4}$alkyl, aryl and heteroaryl, wherein each of aryl and heteroaryl are either unsubstituted or substituted with 1 to 5 substituents independently selected from the group consisting of $C_{1-4}$alkyl, $OC_{1-4}$alkyl, $CF_3$, $NO_2$, and halo.

4. The compound of claim 3, wherein
$R^1$ is OH; and,
$R^5$ and $R^6$ are each independently H, $CH_3$, Cl, or F, with the proviso that when --- between carbon-23 and carbon-24 is a double bond, then $R^5$ is absent; and
$R^8$ is selected from the group consisting of $C_{1-4}$alkyl and aryl, wherein aryl is either unsubstituted or substituted with 1 to 5 substituents independently selected from the group consisting of $C_{1-4}$alkyl, $OC_{1-4}$alkyl, $CF_3$, $NO_2$, and halo.
5. The compound of claim 4, selected from the group consisting of:
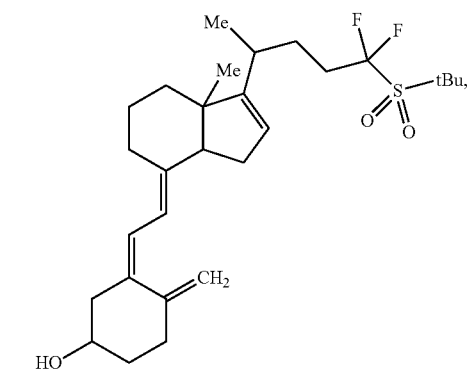
Ia
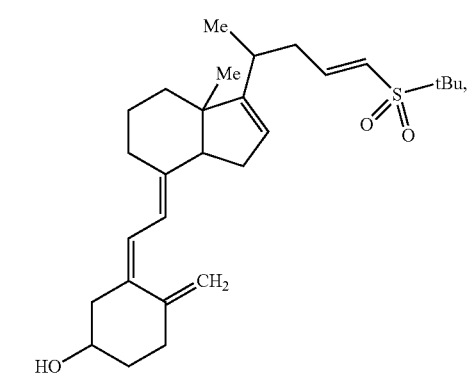
Ib
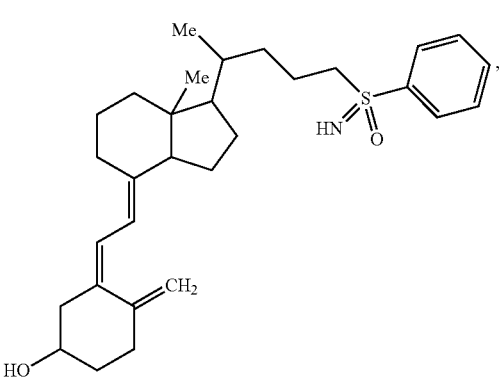
Ic
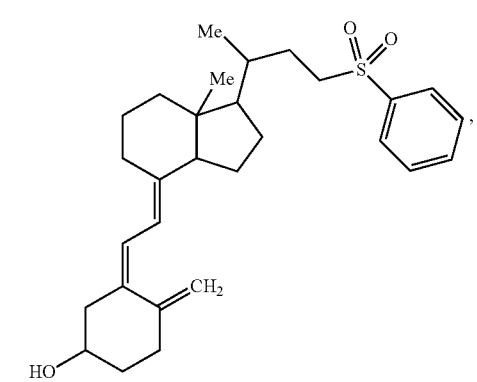
Id
-continued
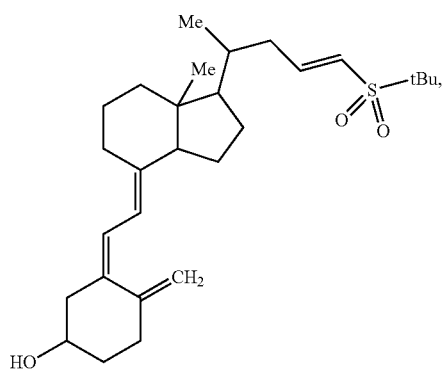
If
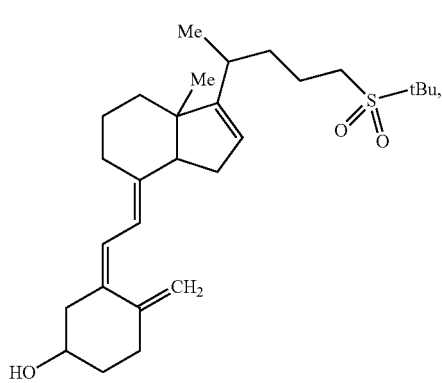
Ig
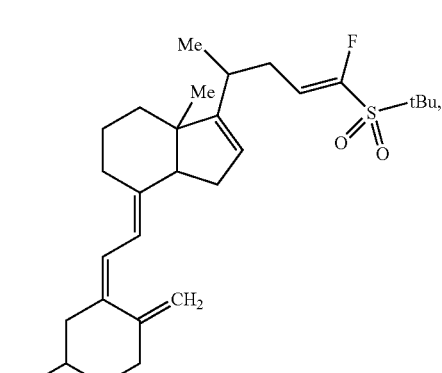
Ih
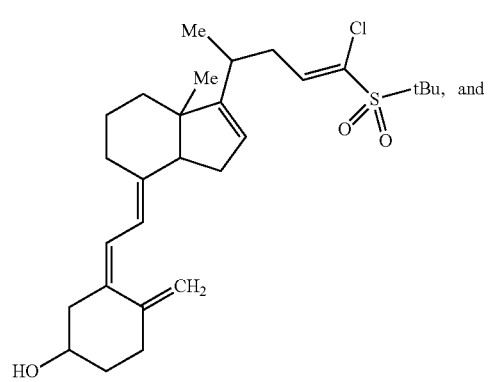
Ij Ik
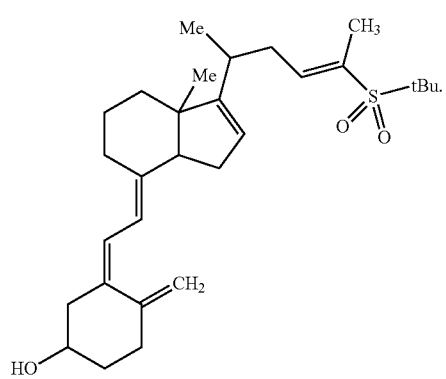
Ibii
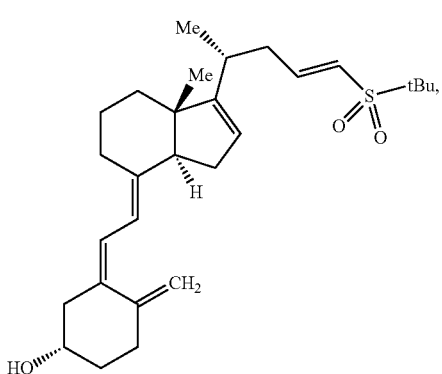
6. The compound of claim 1 having a relative stereochemistry as shown below:
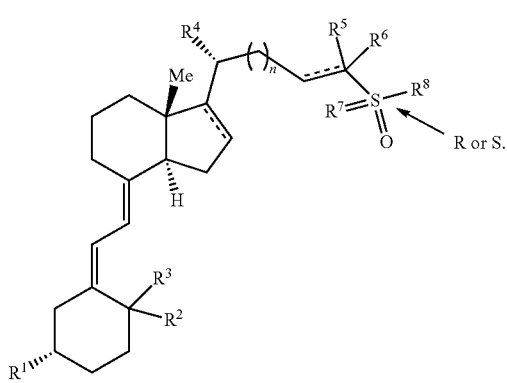
Icii
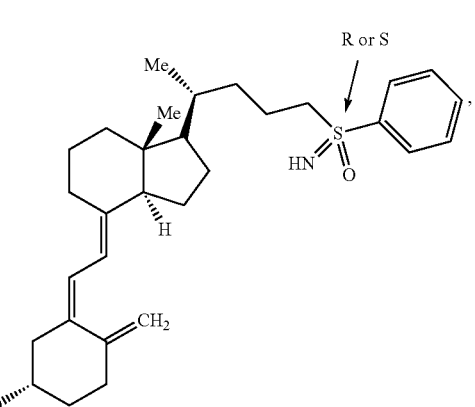
Idii
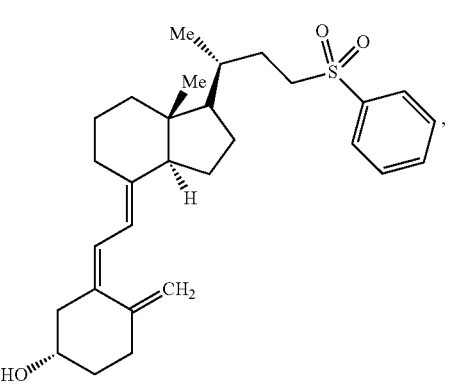
7. The compound of claim 6 selected from the group consisting of:
Iaii
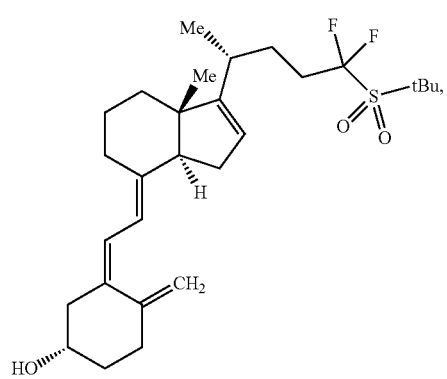
Ifii
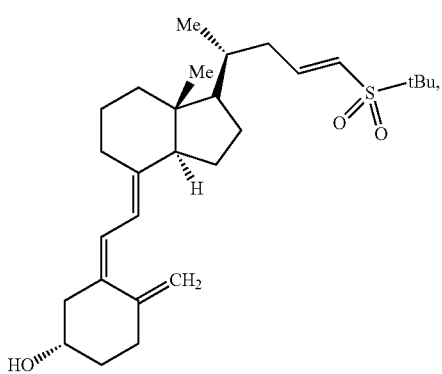

wherein each --- independently is a single bond or a double bond;

n is 0, 1 or 2;

$R^1$ is selected from the group consisting of OH, $OC_{1-6}$alkyl, and halo;

$R^2$ and $R^3$ are each independently H or halo, or together form =$CH_2$;

$R^4$ is $C_{1-6}$alkyl;

$R^5$ and $R^6$ are each independently H, halo, $C_{1-4}$alkyl, or can be taken, together with the carbon atom to which they are bound, to form a $C_{3-6}$cycloalkyl ring, with the proviso that when --- between carbon-23 and carbon-24 is a double bond, then $R^5$ is absent;

$R^7$ is selected from the group consisting of O, NH, N($C_{1-6}$alkyl), and NC(O)$R^9$;

$R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo, OH, $OCF_3$, SH, $SC_{1-4}$alkyl, $NH_2$, $NHC_{1-4}$alkyl, $N(C_{1-4}$alkyl$)(C_{1-4}$alkyl$)$, and CN; and $R^9$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo;

with the proviso that when n is 0, then $R^7$ is O; and with the proviso that when each --- is a single bond, n is 1, $R^1$ is OH, $R^2$ and $R^3$ together form =$CH_2$, $R^4$ is $C_1$alkyl, $R^5$ and $R^6$ are each H, and $R^8$ is methyl, then $R^7$ is selected from the group consisting of NH, N($C_{1-6}$alkyl), and NC(O)$R^9$; or having Formula III, or a pharmaceutically acceptable salt, solvate, or hydrate thereof:

wherein --- is a single bond or a double bond;
R¹ is selected from the group consisting of OH, OC$_{1-6}$alkyl, and halo;
R² and R³ are each independently H or halo, or together form =CH$_2$;
R⁴ is C$_{1-6}$alkyl;
R⁵ and R⁶ are each independently H, halo, C$_{1-4}$alkyl, or can be taken, together with the carbon atom to which they are bound, to form a C$_{3-6}$cycloalkyl ring;
R⁷ is selected from the group consisting of O, NH, N(C$_{1-6}$alkyl), and NC(O)R⁹;
R⁸ is selected from the group consisting of C$_{1-6}$alkyl, C$_{3-6}$cycloalkyl, aryl and heteroaryl, wherein each of C$_{1-6}$alkyl, C$_{3-6}$cycloalkyl, aryl and heteroaryl are either unsubstituted or substituted with 1 to 5 substituents independently selected from the group consisting of C$_{1-4}$alkyl, OC$_{1-4}$alkyl, CF$_3$, NO$_2$, halo, OH, OCF$_3$, SH, SC$_{1-4}$alkyl, NH$_2$, NHC$_{1-4}$alkyl, N(C$_{1-4}$alkyl)(C$_{1-4}$alkyl), and CN; and,
R⁹ is selected from the group consisting of C$_{1-6}$alkyl, C$_{3-6}$cycloalkyl, aryl-C$_{1-4}$alkyl, aryl and heteroaryl, wherein each of C$_{1-6}$alkyl, C$_{3-6}$cycloalkyl, aryl and heteroaryl are either unsubstituted or substituted with 1 to 5 substituents independently selected from the group consisting of C$_{1-4}$alkyl, OC$_{1-4}$alkyl, CF$_3$, NO$_2$, halo.

9. A method for treating diseases which benefit from an increase in the levels of 1α,25-dihydroxyvitamin D$_3$, or for treating diseases which benefit from an inhibition of the catabolism of 1α,25-dihydroxyvitamin D$_3$, or for treating one or more diseases selected from the group consisting of breast cancer, lung cancer, prostate cancer, colon cancer, colorectal cancer, kidney cancer, head and neck cancer, pancreatic cancer, skin cancer, Kaposi's sarcoma, leukemia, and psoriasis, or for inhibiting CYP24 activity in a cell or animal, or for increasing the levels of 1α,25-dihydroxyvitamin D$_3$ in a cell or animal, or for inhibiting the catabolism of 1α,25-dihydroxyvitamin D$_3$ in a cell or animal, comprising administering to a cell or animal in need thereof an effective amount of a compound:
(i) having Formula I, or a pharmaceutically acceptable salt, solvate, or hydrate thereof:

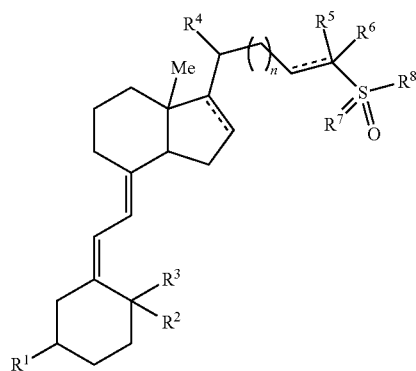

Formula I wherein each --- independently is a single bond or a double bond;
n is 0, 1 or 2;
R¹ is selected from the group consisting of OH, OC$_{1-6}$alkyl, and halo;
R² and R³ are each independently H or halo, or together form =CH$_2$;
R⁴ is C$_{1-6}$alkyl;

R⁵ and R⁶ are each independently H, halo, C$_{1-4}$alkyl, or can be taken, together with the carbon atom to which they are bound, to form a C$_{3-6}$cycloalkyl ring, with the proviso that when --- between carbon-23 and carbon-24 is a double bond, then R⁵ is absent;
R⁷ is selected from the group consisting of O, NH, N(C$_{1-6}$alkyl), and NC(O)R⁹;
R⁸ is selected from the group consisting of C$_{1-6}$alkyl, C$_{3-6}$cycloalkyl, aryl and heteroaryl, wherein each of C$_{1-6}$alkyl, C$_{3-6}$cycloalkyl, aryl and heteroaryl are either unsubstituted or substituted with 1 to 5 substituents independently selected from the group consisting of C$_{1-4}$alkyl, OC$_{1-4}$alkyl, CF$_3$, NO$_2$, halo, OH, OCF$_3$, SH, SC$_{1-4}$alkyl, NH$_2$, NHC$_{1-4}$alkyl, N(C$_{1-4}$alkyl)(C$_{1-4}$alkyl), and CN; and
R⁹ is selected from the group consisting of C$_{1-6}$alkyl, C$_{3-6}$cycloalkyl, aryl-C$_{1-4}$alkyl, aryl and heteroaryl, wherein each of C$_{1-6}$alkyl, C$_{3-6}$cycloalkyl, aryl and heteroaryl are either unsubstituted or substituted with 1 to 5 substituents independently selected from the group consisting of C$_{1-4}$alkyl, OC$_{1-4}$alkyl, CF$_3$, NO$_2$, halo;
with the proviso that when n is 0, then R⁷ is O; and
with the proviso that when each --- is a single bond, n is 1, R¹ is OH, R² and R³ together form =CH$_2$, R⁴ is C$_1$alkyl, R⁵ and R⁶ are each H, and R⁸ is methyl, then R⁷ is selected from the group consisting of NH, N(C$_{1-6}$alkyl), and NC(O)R⁹; or having Formula III, or a pharmaceutically acceptable salt, solvate, or hydrate thereof:

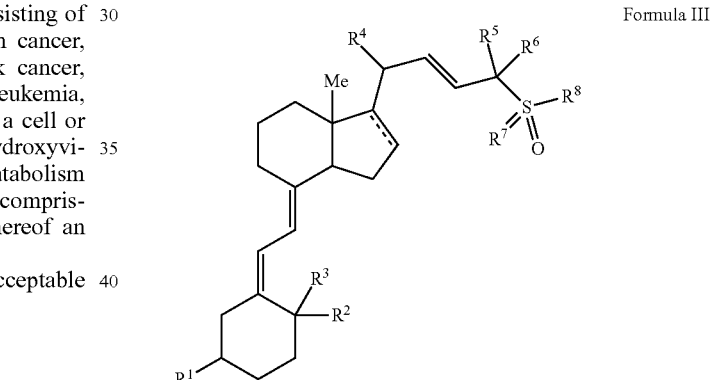

Formula III wherein --- is a single bond or a double bond;
R¹ is selected from the group consisting of OH, OC$_{1-6}$alkyl, and halo;
R² and R³ are each independently H or halo, or together form =CH$_2$;
R⁴ is C$_{1-6}$alkyl;
R⁵ and R⁶ are each independently H, halo, C$_{1-4}$alkyl, or can be taken, together with the carbon atom to which they are bound, to form a C$_{3-6}$cycloalkyl ring;
R⁷ is selected from the group consisting of O, NH, N(C$_{1-6}$alkyl), and NC(O)R⁹;
R⁸ is selected from the group consisting of C$_{1-6}$alkyl, C$_{3-6}$cycloalkyl, aryl and heteroaryl, wherein each of C$_{1-6}$alkyl, C$_{3-6}$cycloalkyl, aryl and heteroaryl are either unsubstituted or substituted with 1 to 5 substituents independently selected from the group consisting of C$_{1-4}$alkyl, OC$_{1-4}$alkyl, CF$_3$, NO$_2$, halo, OH, OCF$_3$, SH, SC$_{1-4}$alkyl, NH$_2$, NHC$_{1-4}$alkyl, N(C$_{1-4}$alkyl)(C$_{1-4}$alkyl), and CN; and,
R⁹ is selected from the group consisting of C$_{1-6}$alkyl, C$_{3-6}$cycloalkyl, aryl-C$_{1-4}$alkyl, aryl and heteroaryl, wherein each of C$_{1-6}$alkyl, C$_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo.

10. A method of increasing the efficacy of a vitamin D receptor agonist comprising co-administering an effective amount of the vitamin D receptor agonist and a compound having Formula I, or a pharmaceutically acceptable salt, solvate, or hydrate thereof:

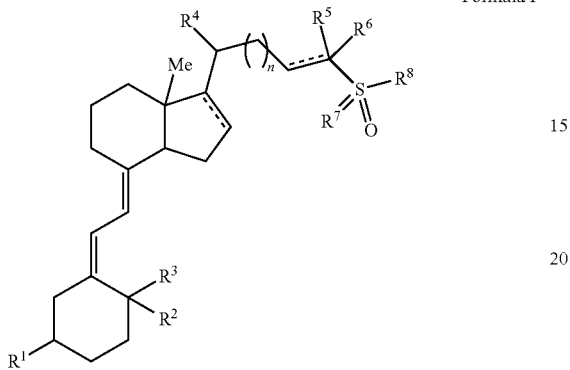

Formula I wherein each --- independently is a single bond or a double bond;
n is 0, 1 or 2;
$R^1$ is selected from the group consisting of OH, $OC_{1-6}$alkyl, and halo;
$R^2$ and $R^3$ are each independently H or halo, or together form $=CH_2$;
$R^4$ is $C_{1-6}$alkyl;
$R^5$ and $R^6$ are each independently H, halo, $C_{1-4}$alkyl, or can be taken, together with the carbon atom to which they are bound, to form a $C_{3-6}$cycloalkyl ring, with the proviso that when --- between carbon-23 and carbon-24 is a double bond, then $R^5$ is absent;
$R^7$ is selected from the group consisting of O, NH, $N(C_{1-6}$alkyl), and $NC(O)R^9$;
$R^8$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo, OH, $OCF_3$, SH, $SC_{1-4}$alkyl, $NH_2$, $NHC_{1-4}$alkyl, $N(C_{1-4}$alkyl)$(C_{1-4}$alkyl), and CN; and
$R^9$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1 to 5 substituents independently selected from the group consisting of $C_{1-4}$alkyl, $OC_{1-4}$alkyl, $CF_3$, $NO_2$, halo;
with the proviso that when n is 0, then $R^7$ is O; and
with the proviso that when each --- is a single bond, n is 1, $R^1$ is OH, $R^2$ and $R^3$ together form $=CH_2$, $R^4$ is $C_1$alkyl, $R^5$ and $R^6$ are each H, and $R^8$ is methyl, then $R^7$ is selected from the group consisting of NH, $N(C_{1-6}$alkyl), and $NC(O)R^9$.

11. The compound of claim 1, wherein:
$R^7$ is O;
with the proviso that when each --- is a single bond, $R^2$ and $R^3$ together form $=CH_2$, $R^4$ is $C_1$alkyl, $R^5$ and $R^6$ are each H, and $R^8$ is methyl, then n is 0 or 2.

12. The method of claim 9, wherein the method comprises treating a disease which benefits from an increase in the levels of 1α,25-dihydroxyvitamin $D_3$.

13. The method of claim 9, wherein the method comprises treating a disease which benefits from an inhibition of the catabolism of 1α,25-dihydroxyvitamin $D_3$.

14. The method of claim 9, wherein the method comprises treating one or more diseases selected from the group consisting of breast cancer, lung cancer, prostate cancer, colon cancer, colorectal cancer, kidney cancer, head and neck cancer, pancreatic cancer, skin cancer, Kaposi's sarcoma, leukemia, and psoriasis.

15. The method of claim 9, wherein the method comprises inhibiting CYP24 activity in a cell or animal.

16. The method of claim 9, wherein the method comprises increasing the levels of 1α,25-dihydroxyvitamin $D_3$ in a cell or animal.

17. The method of claim 9, wherein the method comprises inhibiting the catabolism of 1α,25-dihydroxyvitamin $D_3$ in a cell or animal.

* * * * *

UNITED STATES PATENT AND TRADEMARK OFFICE
CERTIFICATE OF CORRECTION

| | | |
|---|---|---|
| PATENT NO. | : 9,775,903 B2 | Page 1 of 1 |
| APPLICATION NO. | : 13/521980 | |
| DATED | : October 3, 2017 | |
| INVENTOR(S) | : Gary H. Posner et al. | |

It is certified that error appears in the above-identified patent and that said Letters Patent is hereby corrected as shown below:

In the Specification

Column 1, Line 14, (government support statement) please replace with the following:
STATEMENT OF GOVERNMENTAL INTEREST
This invention was made with government support under grant number CA093547, awarded by the National Institutes of Health. The government has certain rights in the invention.

Signed and Sealed this
Twenty-third Day of January, 2018

Joseph Matal
*Performing the Functions and Duties of the
Under Secretary of Commerce for Intellectual Property and
Director of the United States Patent and Trademark Office*